United States Patent
Eissenstat et al.

(10) Patent No.: US 7,507,763 B2
(45) Date of Patent: Mar. 24, 2009

(54) RESISTANCE-REPELLENT RETROVIRAL PROTEASE INHIBITORS

(75) Inventors: Michael Eissenstat, Frederick, MD (US); Andrey Topin, Highland, MD (US); Greg Delahanty, Silver Spring, MD (US); Gnana Ravi Rajendran, Gaithersburg, MD (US)

(73) Assignee: Sequoia Pharmaceuticals, Gaithersburg, MD (US)

( * ) Notice: Subject to any disclaimer, the term of this patent is extended or adjusted under 35 U.S.C. 154(b) by 0 days.

(21) Appl. No.: 11/490,261

(22) Filed: Jul. 21, 2006

(65) Prior Publication Data

US 2006/0258627 A1   Nov. 16, 2006

Related U.S. Application Data

(63) Continuation of application No. 11/124,056, filed on May 9, 2005.

(60) Provisional application No. 60/568,935, filed on May 7, 2004.

(51) Int. Cl.
*A01N 43/08* (2006.01)
*C07D 493/00* (2006.01)

(52) U.S. Cl. ..................... 514/470; 549/464

(58) Field of Classification Search ............. 514/470; 549/464

See application file for complete search history.

(56) References Cited

U.S. PATENT DOCUMENTS 6,534,493 B1   3/2003   Vazquez et al.

FOREIGN PATENT DOCUMENTS

WO    WO 03/049746    *    6/2003

* cited by examiner

*Primary Examiner*—Kamal A Saeed
*Assistant Examiner*—Robert Havlin
(74) *Attorney, Agent, or Firm*—Proskauer Rose LLP

(57) ABSTRACT

Resistance-repellent and multidrug resistant retroviral protease inhibitors are provided. Pharmaceutical composition comprising such compounds, and methods of using such compounds to treat HIV infections in mammals, are also provided.

13 Claims, 7 Drawing Sheets

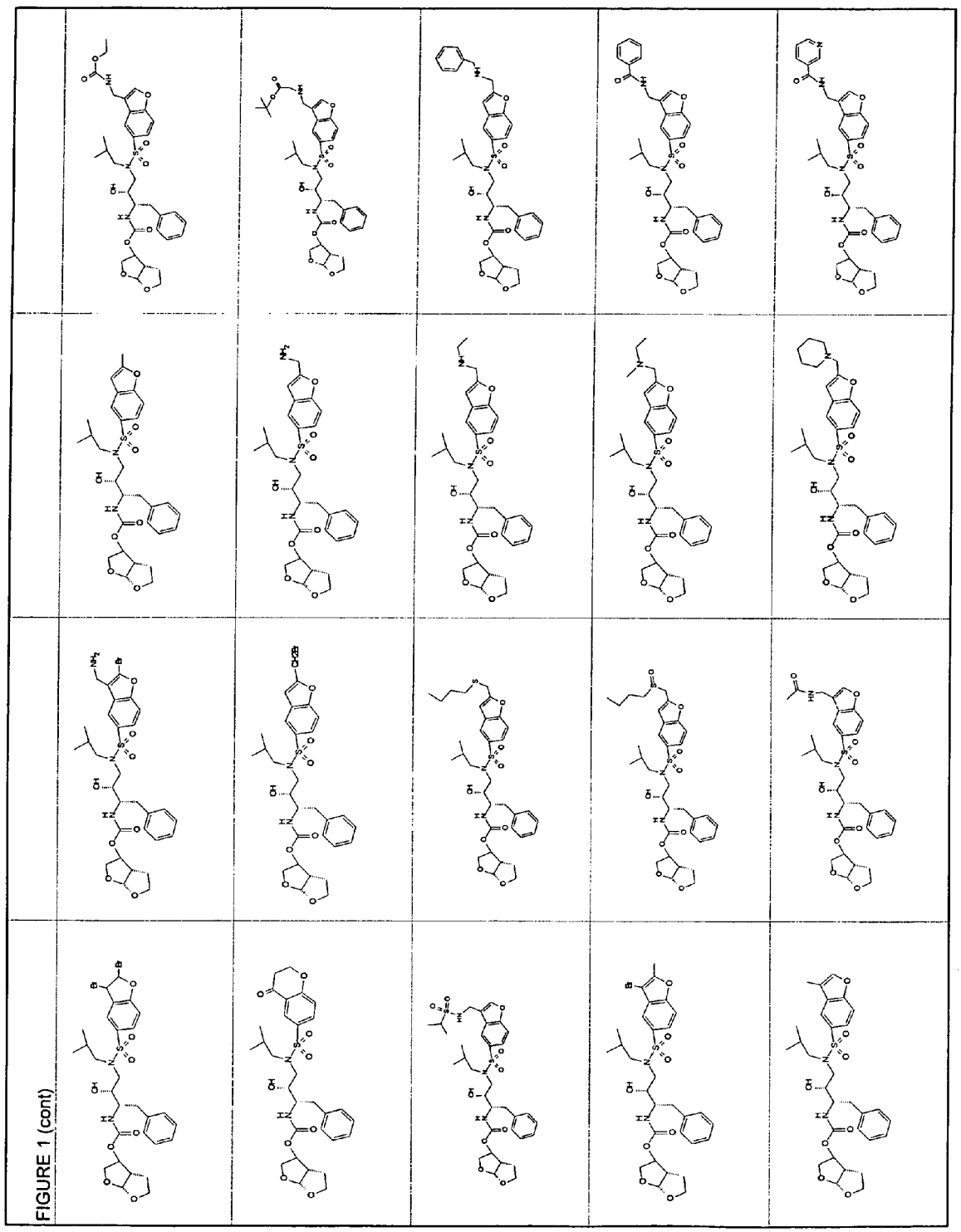

RESISTANCE-REPELLENT RETROVIRAL PROTEASE INHIBITORS

This application is a continuation of application Ser. No. 11/124,056, filed May 9, 2005, and claims priority to Provisional Application Ser. No. 60/568,935, filed May 7, 2004, the contents of both of which are incorporated herein by reference in their entireties.

The present invention relates to retroviral protease inhibitors and, more particularly, relates to novel compounds, compositions and methods for inhibiting retroviral proteases. This invention, in particular, relates to resistance-repellent HIV protease inhibitors, compositions, and uses thereof for treating HIV infections, particularly infections caused by one or more species of drug resistant HIV strains. The invention further provides compounds that are resistant to degradation in vivo and that inhibit degradation of other protease inhibitors.

BACKGROUND OF THE INVENTION

Acquired immune deficiency syndrome (AIDS) is a fatal disease, reported cases of which have increased dramatically within the past several years. Estimates of reported cases in the very near future also continue to rise dramatically. Consequently, there is a great need to develop drugs and vaccines to combat AIDS.

The AIDS virus was first identified in 1983. It has been known by several names and acronyms. It is the third known T-lymphocyte virus (HTLV-III), and it has the capacity to replicate within cells of the immune system, causing profound cell destruction. The AIDS virus is a retrovirus, a virus that uses reverse transcriptase during replication. This particular retrovirus is also known as lymphadenopathy-associated virus (LAV), AIDS-related virus (ARV) and, most recently, as human immunodeficiency virus (HIV). Two distinct families of HIV have been described to date, namely HIV-1 and HIV-2. The acronym HIV is used hereinafter to refer to HIV viruses generically.

Specifically, HIV is known to exert a profound cytopathic effect on CD4+ helper/inducer T-cells, thereby severely compromising the immune system. HIV infection also results in neurological deterioration and, ultimately, in the death of the infected individual.

The field of viral chemotherapeutics has developed in response to the need for agents effective against retroviruses, in particular HIV. Theoretically, there are many ways in which an agent can exhibit anti-retroviral activity. The HIV genome encodes several viral-specific enzymes, such as reverse transcriptase (RT), integrase and protease (PR); viral-specific regulatory proteins, such as tat, rev, nef and vif; and, numerous viral-specific structural proteins, and numerous viral-specific structural proteins, such as capsid, nucleocapsid, matrix, and envelope proteins. Many of these proteins are essential for viral replication. Accordingly, viral replication theoretically could be inhibited through inhibition of any one or all of the proteins involved in viral replication. In practice, however, only inhibitors of RT and PR are currently available for antiviral therapy.

Nucleoside analogues (NRTIs), such as 3'-azido-2',3'-dideoxythymidine (AZT), 2',3'-dideoxycytidine (ddC), and 2',3'-dideoxyinosine (ddI) are known to inhibit HIV RT. There also exist non-nucleoside inhibitors (NNRTIs) specific for HIV-1 RT, such as Nevirapine, and Efavirenz.

Retroviral PR inhibitors (PIs) have also been identified as a class of anti-retroviral agents. The retroviral PR processes polyprotein precursors into viral structural proteins and replicative enzymes. This processing is essential for the assembly and maturation of fully infectious virions. Accordingly, the design of PIs that selectively inhibit PR has been an important therapeutic goal in the treatment of HIV infections and AIDS. Strategies used in the design of HIV PIs include substrate-based, peptidomimetic, transition state-based, and structure-based drug design (Wlodawer & Erickson, *Ann. Rev. Biochem.*, 62, 543-585 (1992)).

Numerous classes of potent peptidic inhibitors of PR have been designed using the natural cleavage site of the precursor polyproteins as a starting point. These inhibitors typically are peptide substrate analogs in which the scissile P1-P1' amide bond has been replaced by a non-hydrolyzable isostere with tetrahedral geometry (Moore et al., *Perspect. Drug Dis. Design*, 1, 85 (1993); Tomaselli et al., *Int. J. Chem. Biotechnology*, 6 (1991); Huff, *J. Med. Chem.*, 34, 2305 (1991); Norbeck et al., *Ann. Reports Med. Chem.*, 26, 141 (1991); Meek, *J. Enzyme Inhibition*, 6, 65 (1992)).

The design of HIV-1 PIs based on the transition-state mimetic concept has led to the generation of a variety of peptide derivatives highly active against viral replication in vitro (Erickson et al., *Science;* 249, 527-533 (1990); Kramer et al., *Science*, 231, 1580-1584 (1986); McQuade et al., *Science*, 247, 454-456 (1990); Meek et al., *Nature (London)*, 343, 90-92 (1990); Roberts et al., *Science*, 248, 358-361 (1990)). These active agents contain a non-hydrolyzable, dipeptide isostere such as hydroxyethylene (McQuade et al., supra; Meek et al., *Nature (London)*, 343, 90-92 (1990); Vacca et al., *J. Med. Chem.*, 34, 1225-1228 (1991)) or hydroxyethylamine (Rich et al., *J. Med. Chem.*, 33, 1285-1288 (1990); Roberts et al., *Science*, 248, 358-361 (1990)) as an active moiety which mimics the putative transition state of the aspartic protease-catalyzed reaction.

Two-fold (C2) symmetric inhibitors of HIV protease represent another class of potent HIV PIs which were created by Erickson et al. on the basis of the three-dimensional symmetry of the enzyme active site (Erickson et al., supra).

Typically, the usefulness of currently available HIV PIs in the treatment of AIDS has been limited by relatively short plasma half-life, poor oral bioavailability, and the technical difficulty of scale-up synthesis (Meek et al. (1992), supra). Although these inhibitors are effective in preventing the retroviral PR from functioning, the inhibitors suffer from some distinct disadvantages. Generally, peptidomimetics make poor drugs due to their potential adverse pharmacological properties, i.e., poor oral absorption, poor stability and rapid metabolism (Plattner et al., Drug Discovery Technologies, Clark et al., eds., Ellish Horwood, Chichester, England (1990)). Furthermore, since the active site of the PR is hindered, i.e., has reduced accessibility as compared to the remainder of the PR, the ability of the inhibitors to access and bind in the active site of the PR is impaired. Those inhibitors that do bind are generally poorly water-soluble, causing distinct problems for formulation and drug delivery.

There are currently six FDA-approved PIs for clinical use—Saquinavir, Ritonavir, Indinavir, Nelfinavir, Amprenavir and Lopinavir. When used alone or in combination with RT inhibitors, PIs dramatically suppress viral replication in HIV-infected individuals. Accordingly, PIs have become "first-line" antiviral agents for the control of HIV-1 (HIV) infections and are widely used in most highly active anti-retroviral therapy (HAART) regimens (Boden & Markowitz, *Antimicrob. Agents Chemo.*, 42, 2775-2783, (1998)). Despite their success, the widespread use of PIs has led to the emergence of several thousands of genetically distinct, drug resistant HIV variants, many of which are cross-resistant to the PIs as a class (Richman, *Adv. Exp. Med. Biol.*, 392, 383-395 (1996); Boden & Markowitz (1998), supra; Shafer et al. *Ann. Intern. Med.*, 128, 906-911(1998)).

The ability of HAART to provide effective long-term antiretroviral therapy for HIV-1 infection has become a complex issue since 40 to 50% of those who initially achieve favorable viral suppression to undetectable levels experience treatment failure (Grabar et al., *AIDS*, 14, 141-149 (1999); Wit et al., *J. Infect. Dis.*, 179, 790-798 (1999)). Moreover, 10 to 40% of antiviral therapy-naive individuals infected with HIV-1 have persistent viral replication (plasma HIV RNA>500 copies/ml) under HAART (Gulick et al., *N. Engl. J. Med.*, 337, 734-739 (1997); Staszewski et al., *N. Engl. J. Med.*, 341, 1865-1873 (1999)), possibly due to transmission of drug-resistant HIV-1 variants (Wainberg and Friedland, *JAMA*, 279, 1977-1983 (1998)). In addition, it is evident that with these anti-HIV drugs only partial immunologic reconstitution is attained in patients with advanced HIV-1 infection.

The clinical manifestations of drug resistance are viral RNA rebound and decreased CD4 cell-counts in the continued presence of drug. The majority of clinical resistance cases are due to viral adaptation through the generation and selection of mutations in the PR and RT genes. Mutant viruses can be generated through errors in reverse transcription of viral RNA, viral RNA synthesis, and recombination events (Coffin, *Retroviruses* pp. 143-144, Cold Spring Harbor Laboratory Press, Plainview (1997)). Mutations within the protease gene that confer clinical drug resistance have emerged for all of the FDA-approved HIV PR inhibitors. The rapid development of drug resistance to PIs, combined with the transmissibility of drug-resistant HIV strains to newly-infected individuals, has resulted in the emergence of a new epidemic of multi-drug resistant AIDS (mdrAIDS). Multi-drug resistant AIDS is caused by a complex spectrum of genetically distinct, infectious new HIV strains that resist most or all forms of currently available treatment.

Accordingly, drug resistant HIV strains represent distinct infectious entities from a therapeutic viewpoint, and pose new challenges for drug design as well as drug treatment of existing infections. Substitutions have been documented in over 45 of the 99 amino acids of the HIV protease monomer in response to protease inhibitor treatment—(Mellors, et al., *International Antiviral News*, 3, 8-13(1995); Eastman, et al., *J. Virol.*, 72, 5154-5164(1998); Kozal, et al., *Nat. Med.*, 2, 753-759(1996)). The particular sequence and pattern of mutations selected by PIs is believed to be somewhat drug-specific and often patient-specific, but high level resistance is typified by multiple mutations in the protease gene which give rise to cross-resistance to all of the PIs.

The challenge of tackling drug resistance is perhaps best illustrated by considering the dynamics of a typical HIV infection. Approximately $10^{12}$ virions are produced in an HIV infected individual every day. The mutation rate of HIV is approximately 1 per genome, which numbers $10^4$ nucleotide bases. Therefore, every nucleotide in the genome is mutated $10^8$ times per round of replication in the patient. This means that all possible single site mutations are present in at least the 0.01% level. Because of this, drugs that can be rendered ineffective with a single mutation from wild type have the shortest effective lifetime in monotherapy settings. The apparently large number of possible mutational pathways, possible mutational combinations, and the danger of generating class-specific cross resistance can make the choice of a subsequent protease inhibitor-containing-combination regimen for "salvage therapy" seem very complicated and risky. Even the choice of protease inhibitor with which to initiate therapy, so-called "first-line" therapy, can be a risky enterprise that may inadvertently select for an undesired resistance pathway. Drug-naïve HIV-infected individuals pose even more of a risk for developing resistance to first-line therapies.

For the reasons outlined above, the development of new anti-HIV-1 therapeutics presents formidable challenges different from those in the design of the first line drugs, particularly in regard to consideration of selection pressure mechanisms in addition to the conventional issues of potency, pharmacology, safety, and mechanism of drug action. Indeed, HIV-1 can apparently develop resistance to any existing anti-HIV-1 therapeutic. In particular, the very features that contribute to the specificity and efficacy of RTIs and PIs provide the virus with a strategy to mount resistance (Erickson and Burt, *Annu. Rev. Pharmacol. Toxicol.*, 36, 545-571 (1996); Mitsuya and Erickson, *Textbook of AIDS Medicine*, pp. 751-780, Williams and Wilkins, Baltimore (1999)), and it seems highly likely that this resistance issue will remain problematic for years to come.

Despite numerous studies of drug resistance to PIs, successful strategies to design inhibitors directly targeted against drug resistant HIV have been lacking. Instead, efforts have been directed at identifying drugs with increased potency to wild type virus, and with longer pharmacological half-lives (exemplified by Amprenavir). Another approach has been to develop PIs that are sensitive to pharmacologic "boosting" using Ritonavir, a PI that is also a potent inhibitor of the cytochrome enzymes. The latter approach is exemplified by Kaletra (a Lopinavir/Ritonavir combination). Several other PIs have been identified based on efforts to improve plasma half-life and bioavailability. For example, PIs incorporating the 2,5-diamino-3,4-disubstituted-1,6-diphenylhexane isostere are described in Ghosh et. al., *Bioorg. Med. Chem. Lett.*, 8, 687-690 (1998) and U.S. Pat. No. 5,728,718 (Randad et al.), both of which are incorporated herein by reference in their entirety. HIV PIs, which incorporate the hydroxyethylamine isostere, are described in U.S. Pat. No. 5,502,060 (Thompson et al.), U.S. Pat. No. 5,703,076 (Talley et al.), and U.S. Pat. No. 5,475,027 (Talley et al.).

Recent studies have revealed the structural and biochemical mechanisms by which mutations in the PR gene of HIV confer drug resistance in the presence of PIs. An important conclusion that emerges from the body of evidence on resistance to PIs is that HIV variants that exhibit cross-resistance to first-line PIs should be considered to be unique infectious agents. New therapeutic agents need to be developed to successfully treat patients infected with these viruses. New strategies for drug discovery need to be explored to develop effective protease inhibitor-based treatments for patients with multidrug resistant virus. HIV protease is one the most intensively studied molecular targets in the history of infectious disease.

More recently, new mutant strains of HIV have emerged that are resistant to multiple, structurally diverse, experimental and chemotherapeutic HIV PIs. Such mdrHIV strains are typically found in infected patients who have undergone treatment with a combination of PIs or with a series of different PIs. The number of reported cases of patients infected with mdrHIV is rising steadily. Tragically for these patients, the available options for AIDS chemotherapy and/or HIV management is severely limited or is, otherwise, completely nonexistent.

A biochemical fitness profiling strategy has recently been used to identify a novel subclass of potent PIs that have broad-based activity against mdrHIV (Gulnik et al., (1995) supra; Erickson et al., WO 99/67254; Erickson et al., WO 99/67417).

In view of the foregoing problems, there exists a need for inhibitors against drug resistant and mdrHIV strains. Further, there exists a need for inhibitors against drug resistant and multi-drug resistant HIV proteases (mdrPR). Further still, there exists a need for inhibitors of HIV that can prevent or slow the emergence of drug resistant and mdrHIV strains in infected individuals. Inhibitors with the ability to inhibit mdrHIV strains, and to slow the emergence of drug resistant strains in wild type HIV infections, are defined as "resistance-repellent" inhibitors. There also exists a need for robust methods that can be used to design "resistance-repellent" inhibitors.

SUMMARY OF THE INVENTION

The present invention provides such resistance-repellent inhibitors of mdrPR, their compositions, methods of design, and uses thereof for treating mdrHIV and wtHIV infections in salvage therapy and first-line therapy modalities.

More particularly, the invention provides HIV protease inhibitors represented by the formula I:

X-A-B-A'-X' 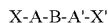 I where X is a moiety that contains two or more hydrogen bond acceptors capable of interacting with the backbone NH atoms of residues 29 and 30 of an HIV protease, A is a 2-6 atom linker that contains at least one hydrogen bond acceptor that interacts with the flap water, and one hydrogen bond donor that interacts with the backbone CO atom of residue 27, B contains 1-3 atoms that can form hydrogen bonds with either or both carboxylate side chain oxygens of Asp25 and Asp125 of said protease, A' is a 2-6 atom linker that contains at least one hydrogen bond acceptor that interacts with the flap water; and X' is a moiety that can form one or more hydrogen bonds with the backbone NH atoms of residues 129 and/or 130, provided that the compound of Formula I is not any of the compounds described in *J. Med. Chem.* 39:3278-3290 (1996), in *Bioorg. Med. Chem. Lett.* 8:687-690 (1998), or *Bioorg. Med. Chem. Lett.* 8:979-982 (1998).

The invention also provides a compound as described above, bound in a complex with wild type or drug resistant mutant forms of HIV-1 protease.

The invention further provides pharmaceutical compositions, comprising an inhibitor as described above, together with a pharmaceutically acceptable additive, excipient, or diluent. The composition may further comprise an additional HIV protease inhibitor and/or an HIV reverse transcriptase inhibitor.

Specifically, the invention provides an HIV protease inhibitor represented by a formula:

X-A-B-A'-X' 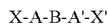

where:

X is a 5-7 membered non-aromatic monocyclic heterocycle, where the heterocycle is optionally fused or bridged with one or more 3-7 membered non-aromatic monocyclic heterocycle to form a polycyclic system, where any of the heterocyclic ring systems contains one or more heteroatoms selected from O, N, S, or P; where any nitrogen forming part of the heterocycles may optionally be substituted by R2, R3, R6, R7 or O; where any sulfur may optionally be substituted by one or two oxygen atoms; where any P may optionally be substituted by one or more of O, NR2, or S, and any of the ring systems optionally contains 1 to 6 substituents selected from the group consisting of R2, R3, R5, and R6;

A is ZCZNH, ZCOCONH, ZS(O)$_2$NH, ZP(O)(V)NH, CONH, COCONH, S(O)$_2$NH, P(O)(V)NH, where Z is NR2, O, S, or C(R2)$_2$, and V is OR2 or NR2;

B is

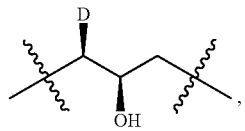

where D is selected from alkyl, alkenyl, alkynyl, aryl, cycloalkyl, or aralkyl optionally substituted with one or more groups selected from alkyl, halo, nitro, cyano, CF$_3$, C3-C7 cycloalkyl, C5-C7 cycloalkenyl, R6, OR2, SR2, NHR2, OR3, SR3, NHR3, OR6, SR6, or NHR6;

A' is N(D')E', where D' is selected from alkyl, alkenyl, alkynyl, aryl, cycloalkyl, or aralkyl optionally substituted by alkyl, halo, nitro, cyano, CF$_3$, O-alkyl, or S-alkyl, and E' is —CO— or —SO$_2$—;

X' is

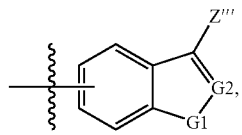

where G1 is NH or O;
where G2 is CZ" or N;
where Z" is selected from the group consisting of halogen, R2, R3, or R6;
where Z''' is selected from the group consisting of H or R2, R3, R6, halo, haloalkyl, C(R2)$_2$OR, C(R2)$_2$COR, C(R2)$_2$OCOR, C(R2)$_2$CO$_2$R, C(R2)$_2$N(R)$_2$, C(R2)$_2$SR, C(R2)$_2$SOR, C(R2)$_2$SO$_2$R, optionally substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR;

where X' is optionally substituted with one or more substituents, each independently selected from (a)-(h) as follows:
(a) OR3, OR6, OR7, OR2;
(b) alkyl substituted by R3, R5, R6;
(c) C2-C6 alkenyl, C2-C6 alkynyl, C3-C8 cycloalkyl, C5-C8 cycloalkenyl, and heterocyclyl, which groups may be optionally substituted with one or more substituents selected from R5;
(d) aryl or heteroaryl, where the aryl or heteroaryl may be optionally substituted with one or more groups selected from the group consisting of aryl, heteroaryl, R2, R3, R4 and R6;
(e) C3-C7 cycloalkyl substituted by R2, R3, R5 or R6;
(f) CO$_2$H or R7;
(g) NR8R8, NR7R8, NR7R7; and
(h) SO$_n$N(R8)$_2$, SO$_n$NR7R8, SR8, S(O)$_n$R8; and n is 1 or 2;

R is H or is selected from the group consisting of alkyl, aryl, alkenyl, alkynyl, cycloalkyl, cycloalkenyl, heterocyclo and heteroaryl; optionally substituted by halo, hydroxy, alkoxy, aryloxy, cycloalkoxy, heteroaryloxy, cyano, nitro, alkylthio, arylthio, cycloalkylthio, amino, or mono- or dialkylamino, mono- or diarylamino, mono- or di-cycloalkylamino, mono- or di-heteroarylamino, alkanoyl, cycloalkanoyl, aroyl, heteroaroyl, carboxamido, mono- or dialkylcarboxamido, mono- or diarylcarboxamido, sulfonamido, mono- or dialkylsulfonamido, mono- or diarylsulfonamido, alkylsulfinyl, alkylsulfonyl, arylsulfinyl, arylsulfonyl, cycloalkylsulfinyl, cycloalkylsulfonyl, heteroarylsulfinyl, heteroarylsulfonyl;

R2 is H or C1-C6 alkyl; optionally substituted by C2-C6 alkenyl, C2-C6 alkynyl, C3-C8 cycloalkyl, C5-C8 cycloalkenyl, heterocyclo; which groups may be optionally substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCO$_n$R, =NNRS(O)$_n$N(R)$_2$, or =NNRS(O)$_n$(R);

or R2 is C1-C6 alkyl; substituted by aryl or heteroaryl; which groups may be optionally substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR;

or R2 is C1-C6 alkyl; optionally substituted by halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCO$_n$R, =NNRS(O)$_n$N(R)$_2$, or =NNRS(O)$_n$(R);

R3 is C2-C6 alkenyl, C2-C6 alkynyl, C3-C8 cycloalkyl, C5-C8 cycloalkenyl, or heterocyclo; which groups may be optionally substituted with one or more substituents selected from the group consisting of halo, OR2, R2-OH, R2-halo, NO$_2$, CN, CO$_n$R2, C(O)N(R2)$_2$, C(O)N(R2)N(R2)$_2$, C(S)R2, C(S)N(R2)$_2$, S(O)$_n$N(R2)$_2$, SR2, SO$_n$R2, N(R)$_2$, N(R2)CO$_n$R2, NR2S(O)$_n$R, NR2C[=N(R2)]N(R2)$_2$, N(R2)N(R2)CO$_n$R2, NR2PO$_n$N(R2)$_2$, NR2PO$_n$OR2, oxo, =N—OR2, =N—N(R2)$_2$, =NR2, =NNRC(O)N(R2)$_2$, =NNR2C(O)$_n$R2, =NNR2S(O)$_n$N(R2)$_2$, or =NNR2S(O)$_n$(R2);

R4 is selected from the group consisiting of halo, OR8, R2-OH, R3-OH, R2-halo, R3-halo, NO$_2$, CN, CO$_n$R8, CO$_n$R8, CON(R8)$_2$, C(O)N(R8)N(R8)$_2$, C(S)R8, C(S)N(R8)$_2$, SO$_n$N(R8)$_2$, SR8, SO$_n$R8, N(R8)$_2$, N(R8)CO$_n$R8, NR8S(O)$_n$R8, NR8C[=N(R8)]N(R8)$_2$, N(R8)N(R8)CO$_n$R8, NR8PO$_n$N(R8)$_2$, NR8PO$_n$OR8, OC(O)R2, OC(S)R8, OC(O)N(R8)$_2$, OC(S)N(R8)$_2$ and OPO$_n$(R8)$_2$;

R5 is selected from the group consisting of OR8, N(R8)$_2$, NHOH, N(R8)COR8, NR8S(O)$_n$R8, NR8C[=N(R8)]N(R8)$_2$, N(R8)N(R8)C(O)R8, NR8PO$_n$N(R8)$_2$, NR8PO$_n$OR8, R2OH, R3-OH, R2-halo, R3-halo, CN, CO$_n$R8; CON(R8)$_2$, C(O)N(R8)N(R8)$_2$, C(S)$_n$R8, C(S)N(R8)$_2$, S(O)$_n$R8, SO$_n$N(R8)$_2$, halo, NO$_2$, SR8, oxo, =N—OH, =N—OR8, =N—N(R8)$_2$, =NR8, =NNR8C(O)N(R8)$_2$, =NNR8C(O)$_n$R8, =NNR8S(O)$_n$N(R8)$_2$, or =NNR8S(O)$_n$(R8) and R3;

R6 is aryl or heteroaryl, where the aryl or heteroaryl may be optionally substituted with one or more groups selected from aryl, heteroaryl, R2, R3, halo, OR2, R2OH, R2-halo, NO$_2$, CN, CO$_n$R2, C(O)N(R2)$_2$, C(O)N(R2)N(R2)$_2$, C(S)R2, C(S)N(R2)$_2$, S(O)$_n$N(R2)$_2$, SR2, SO$_n$R2, N(R)$_2$, N(R2)CO$_n$R2, NR2S(O)$_n$R2, NR2C[=N(R2)]N(R2)$_2$, N(R2)N(R2)CO$_n$R2, NR2PO$_n$N(R2)$_2$, NR2PO$_n$OR2, OC(O)R2, OC(S)R2, OC(O)N(R2)$_2$, OC(S)N(R2)$_2$, OPO$_n$(R2)$_2$, R7 is selected from the group consisting of C(O)$_n$R8; C(S)R8, C(O)N(R8)$_2$, C(S)N(R8)$_2$, S(O)$_n$R8 and S(O)nN(R8)$_2$;

R8 is R2, R3, or R6;

R9 is alkyl optionally substituted by R3, R5, R6; C2-C6 alkenyl, C2-C6 alkynyl, C3-C8 cycloalkyl, C5-C8 cycloalkenyl, and heterocyclo, which groups may be optionally substituted with one or more substituents selected from the group consisting of —OR2, C(O)N(R2)$_2$, S(O)$_n$N(R2)$_2$, CN, SR2, SO$_n$R2, COR2, CO$_2$R2 or NR2C(O)R2, R5, and R7; aryl or heteroaryl, where the aryl or heteroaryl may be optionally substituted with one or more groups selected from the group consisting of aryl, heteroaryl, R2, R3, R4, and R6; C3-C7 cycloalkyl optionally substituted by R2, R3, R5, R6; CO$_2$H or R7; NR3R3, NR6R6, NR7R7, NR3R6, NR6R7, NR3R7, NR2R3, NR2R6, NR2R7, NR2R2; SO$_n$N(R8)$_2$, SO$_n$NR7R8, SR8, S(O)$_n$R8, and n is 1 or 2; SO$_n$N(R2)$_2$, SO$_n$N(R3)$_2$, SO$_n$N(R6)$_2$, SO$_n$N(R7)$_2$, SO$_n$NR2R3, SO$_n$NR2R6, SO$_n$NR2R7, SO$_n$NR3R6, SO$_n$NR3R7, SO$_n$NR6R7; S(O)$_m$R2, S(O)$_m$R3, S(O)$_m$R6; and m is 0, 1 or 2; and each n is independently 1 or 2.

In one embodiment,

X is

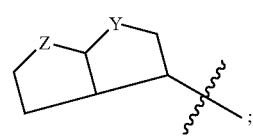

Y is O, NH, or S;

Z is O, NH, or S; and any ring carbon many optionally be substituted by R2, R3, R5, or R6.

In another embodiment, X is

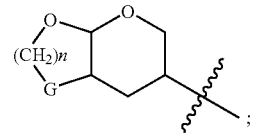

where

G is C, O, NR2,or S;

n is an integer between 1-2; and any ring carbon may optionally be substituted by R2, R3, R5, or R6.

In yet another embodiment, X is

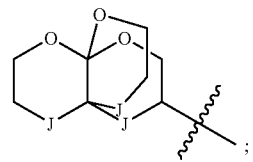

where

J is independently CH$_2$, or O and where any ring carbon may optionally be substituted by R2, R3, R5, or R6.

In still another embodiment, X is

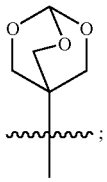

where any ring carbon may optionally be substituted by R2, R3, R5, or R6.

In another embodiment, X is

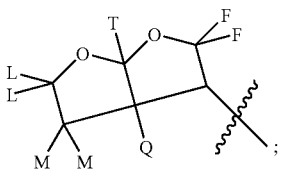

where each L is independently H, lower alkyl, oxo, or L forms a carbocyclic or heterocyclic ring with M;

each M is independently H, OH, chloro, fluoro, or M forms a carbocyclic or heterocyclic ring with Q, provided that if one M is OH, the other M is not OH;

Q is H, OH, amino, lower alkyl, alkylamino, alkoxy, halo, or forms a 3-7-membered carbocyclic or heterocyclic ring together with T;

each F is independently H, OH, lower alkyl, halo, or spirocylopropyl, provided that if one R is OH, the other R is not OH; and T is H or F, or T forms a carbocyclic or heterocyclic ring together with F.

In a particular embodiment, X is tetrahydrofurodihydrofuranyl, tetrahydrofurotetrahydrofuranyl, tetrahydropyranotetrahydrofuranyl or tetrahydropyranodihydrofuranyl;

A is OCONH;

B is

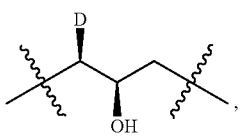

where D is selected from alkyl, alkenyl, alkynyl, aryl, cycloalkyl, or aralkyl optionally substituted with one or more groups selected from alkyl, halo, nitro, cyano, $CF_3$, C3-C7 cycloalkyl, C5-C7 cycloalkenyl, R6, OR2, SR2, NHR2, OR3, SR3, NHR3, OR6, SR6, or NHR6; and A' is N(D')E', where D' is alkyl, alkenyl, alkynyl aryl, cycloalkyl, or aralkyl optionally substituted by alkyl, halo, or $CF_3$, and E' is —$SO_2$—.

In still another embodiment, X is tetrahydrofurotetrahydrofuranyl;

A is OCONH;

B is

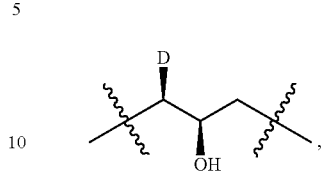

where D is benzyl; and

A' is N(D')E', where D' is isobutyl and E' is —$SO_2$—;

In another embodiment, X is

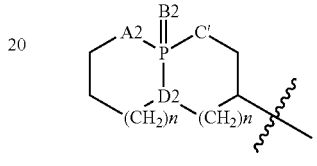

or

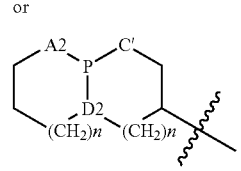

where A2, B2, and C' are each independently O, NR2, or S; D2 is CH or N; and n is an integer between 1 and 2.

Alternatively, X is

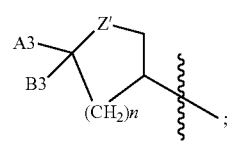

where

A3 is H, F or alkoxy;

B3 is F, alkoxy, lower alkyl, or A3 and B3 can form a 3-7 membered heterocyclic ring;

Z' is O, NR2, or S; and n is an integer between 1-3.

In other embodiments, X' is selected from

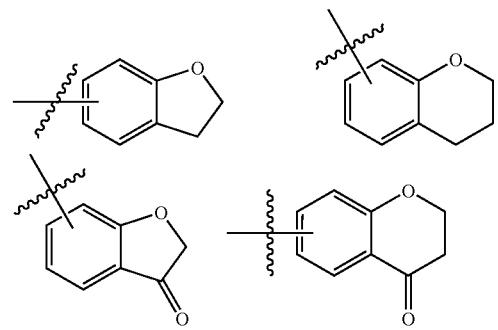

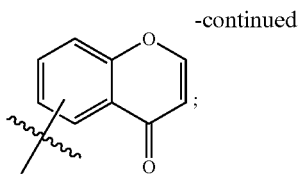
-continued where the groups are optionally substituted with one or more of the following groups:

oxo, halo, OR3, OR6, OR7, OR2 provided R2 is not H or unsubstituted alkyl;

alkyl optionally substituted by R3, R5, R6 provided R5 is not halo;

C2-C6 alkenyl, C2-C6 alkynyl, C3-C8 cycloalkyl, C5-C8 cycloalkenyl, and heterocyclo, which groups may be optionally substituted with one or more substituents selected from R5;

aryl or heteroaryl, where the aryl or heteroaryl may be optionally substituted with one or more groups selected from the group consisting of aryl, heteroaryl, R2, R3, R4, and R6;

C3-C7 cycloalkyl substituted by R2, R3, R5, R6; provided R2 is not H;

$CO_2H$ or R7; provided R8 is not H or unsubstituted alkyl;
NR8R8, NR7R8, NR7R7; provided R8 is not H or unsubstituted alkyl; and $SO_nN(R8)_2$, $SO_nNR7R8$, SR8, $S(O)_nR8$, provided R8 is not H or methyl; and n is 1 or 2.

In the embodiments described above, Z''' may be H and Z'' may be $CH_2Cl$, $CH_2Br$, $CH_2I$, $CH_2OR$, $CH_2NH_2$, $CH_2N(R)_2$, $CH_2N(R)COR$ or $CH_2N(R)CO_2R$. R may be H or $C_1$-$C_6$ alkyl.

In the embodiments described above, Z'' may be H and Z''' may be selected from the group consisting of H, $C(R2)_2$-halo, $C(R2)_2R$, $C(R2)_2OR$, $C(R2)_2COR$, $C(R2)_2OCOR$, $C(R2)_2CO_2R$, $C(R2)_2N(R)_2$, $C(R2)_2SR$, $C(R2)_2SOR$, $C(R2)_2SO_2R$, $C(R2)_2N(R)CO_nR$, $C(R2)_2NRS(O)_nR$, $C(R2)_2NRC[=N(R)]N(R)_2$, $C(R2)_2N(R)N(R)CO_nR$, $C(R2)_2C(S)R$, $C(R2)_2C(S)N(R)_2$, and $C(R2)_2SO_nN(R)_2$.

In specific embodiments, Z''' may be selected from the group consisting of H, Me, CH2OH, CH2OAc, CH2OMe, CH2NHiPr, CH2NH2, CH2S(O)Bu, CH2S-iPr, CH2OCOtBu, CH2NHCH2CH2OMe, CH2NHCOiPr, CH2NHCOPh, CH2NHCO2Pr, CH2NHCOMe, CH2-4-Morpholino, CH2-1-piperidino, CH2NHBoc, CH2NHCO2Et, CH2NHCOEt, CH2NHS02iPr, CH2NHCbz, CH2NH(CH2)2-2-pyridyl, CH2NHCO-3-pyridyl, CH2NHCOCH2SCH2Ph, CH2NHCOCH2S(O)CH2Ph, CH2NHCO-2-furanyl, CH2N(CO2Et)CH2CH2OMe, NHCH(Me)CO2Et, CH2NHSO2Et, CH2NHSO2Me, CH2NMeSO2Me, CH2NMeTs, CH2NHCO2iPr, CH20COiPr, CH2-1-imidazole, CH2NHCH2CH2SEt, CH2N((CH2)2OMe)SO2Et, CH2NHCH2CF2CF3, CH2NHCH2CF2CF3, CH2NHCH2CF3, CH2NHCH2CH2OPh, CH2NHBu, CH2NHCH2Ph, CH2SCH2CF3, CH2NHCOCF3, CH2NHcyclopentyl, CH2NHCH2CH2NHBoc, CH2NH(CH2)3-1-pyrrolidine-2-one, CH2NHCH2cyclohexyl, CH2NHCH2-2-pyridyl, CH2NHCH2-4-(2-methylthiazole), CH2SO2Me, CH2NHCOCF2CF3, CH2OCH2CF3, CH2N(Ac)CH2CF3, and CH2NHCH2-5-benzofuranyl.

The inhibitor may be selected from the group of compounds in FIGS. 1-3.

The invention also provides a compound as described above, bound in a complex with wild type or drug resistant mutant forms of HIV-1 protease.

The invention also provides a pharmaceutical composition comprising an effective amount of an inhibitor as described above and a pharmaceutically acceptable additive, excipient, or diluent. The composition may also comprise another anti-retroviral agent, such as a second HIV inhibitor. The additional HIV inhibitor(s) may be an HIV protease inhibitor and/or an HIV reverse transcriptase inhibitor.

The invention also provides a method of treating a patient suffering from HIV infection, for example multi-drug resistant HIV infection, comprising administering to the patient a compound or composition as described above.

The invention further provides a method of inhibiting metabolic degradation of a retroviral protease inhibitor in a subject being treated with the inhibitor, comprising administering to the subject a degradation-inhibiting amount of a compound as described above. The compound may be administered substantially contemporaneously with the inhibitor and/or prior to administration of the inhibitor.

The invention also provides HIV protease inhibitors having the structure

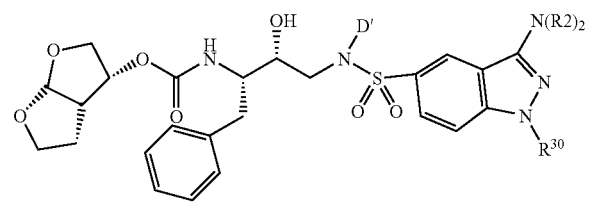

where each R2 may be the same or different, and R2 is H or C1-C6 alkyl; optionally substituted by C2-C6 alkenyl, C2-C6 alkynyl, C3-C8 cycloalkyl, C5-C8 cycloalkenyl, heterocyclo; which groups may be optionally substituted with one or more substituents selected from the group consisting of halo, OR, ROH, R-halo, $NO_2$, CN, $CO_nR$, $CON(R)_2$, $C(S)R$, $C(S)N(R)_2$, $SO_nN(R)_2$, SR, $SO_nR$, $N(R)_2$, $N(R)CO_nR$, $NRS(O)_nR$, $NRC[=N(R)]N(R)_2$, $N(R)N(R)CO_nR$, $NRPO_nN(R)_2$, $NRPO_nOR$, oxo, $=N—OR$, $=N—N(R)_2$, $=NR$, $=NNRC(O)N(R)_2$, $=NNRCO_nR$, $=NNRS(O)_nN(R)_2$, or $=NNRS(O)_n(R)$;

or R2 is C1-C6 alkyl; substituted by aryl or heteroaryl; which groups may be optionally substituted with one or more substituents selected from the group consisting of halo, OR, ROH, R-halo, $NO_2$, CN, $CO_nR$, $CON(R)_2$, $C(S)R$, $C(S)N(R)_2$, $SO_nN(R)_2$, SR, $SO_nR$, $N(R)_2$, $N(R)CO_nR$, $NRS(O)_nR$, $NRC[=N(R)]N(R)_2$, $N(R)N(R)CO_nR$, $NRPO_nN(R)_2$, $NRPO_nOR$;

or R2 is C1-C6 alkyl; optionally substituted by halo, OR, ROH, R-halo, $NO_2$, CN, $CO_nR$, $CON(R)_2$, $C(S)R$, $C(S)N(R)_2$, $SO_nN(R)_2$, SR, $SO_nR$, $N(R)_2$, $N(R)CO_nR$, $NRS(O)_nR$, $NRC[=N(R)]N(R)_2$, $N(R)N(R)CO_nR$, $NRPO_nN(R)_2$, $NRPO_nOR$, oxo, $=N—OR$, $=N—N(R)_2$, $=NR$, $=NNRC(O)N(R)_2$, $=NNRCO_nR$, $=NNRS(O)_nN(R)_2$, or $=NNRS(O)_n(R)$;

and where D' is selected from the group consisting of alkyl, alkenyl, alkynyl, aryl, cycloalkyl and aralkyl, and is optionally substituted by alkyl, halo, nitro, cyano, $CF_3$, halo-C1-C6 alkyl, O-alkyl, or S-alkyl.

DETAILED DESCRIPTION

Figure 1:
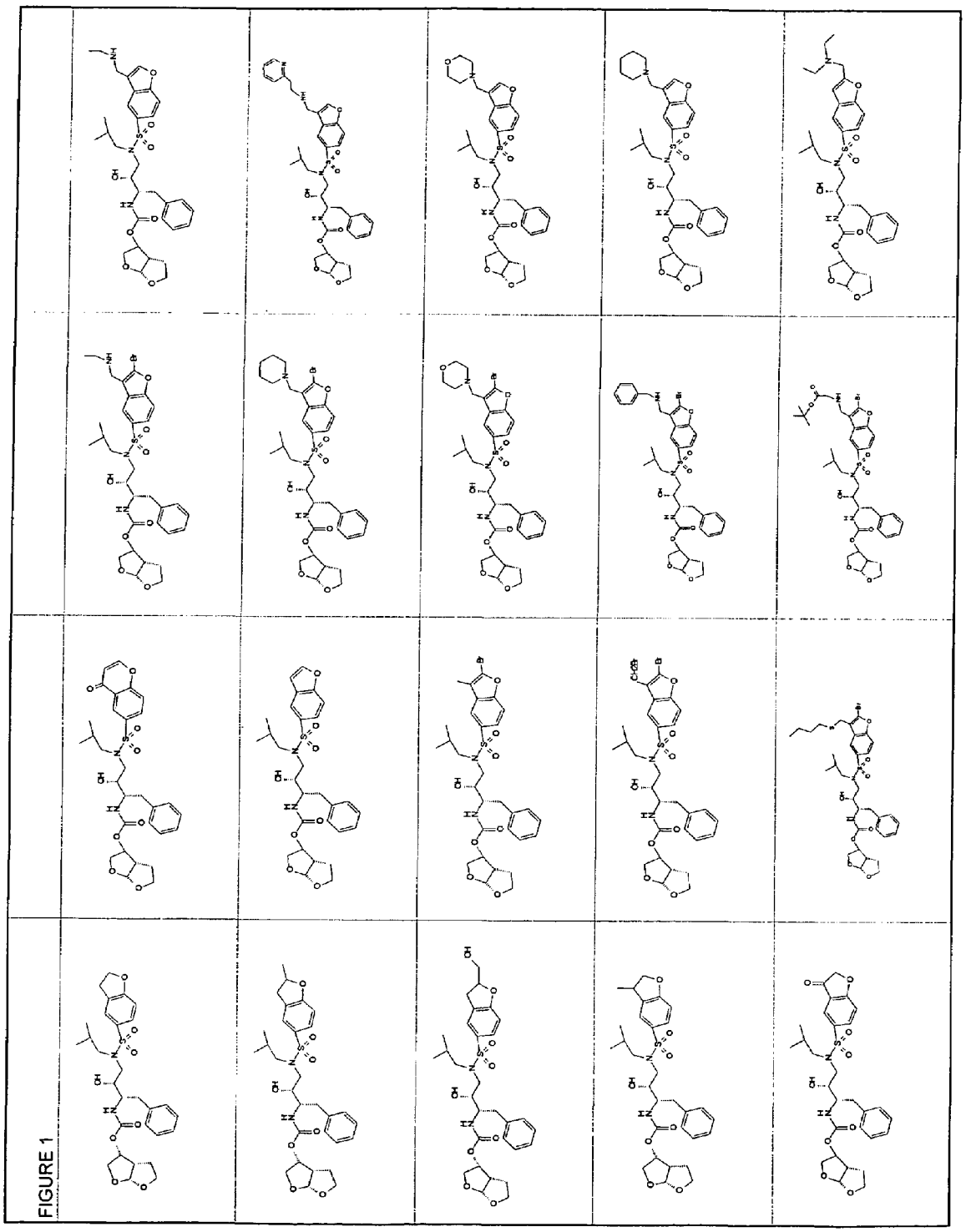
FIG. 1 shows the structures of a selection of benzofuran-containing HIV protease inhibitors.
Figure 1:
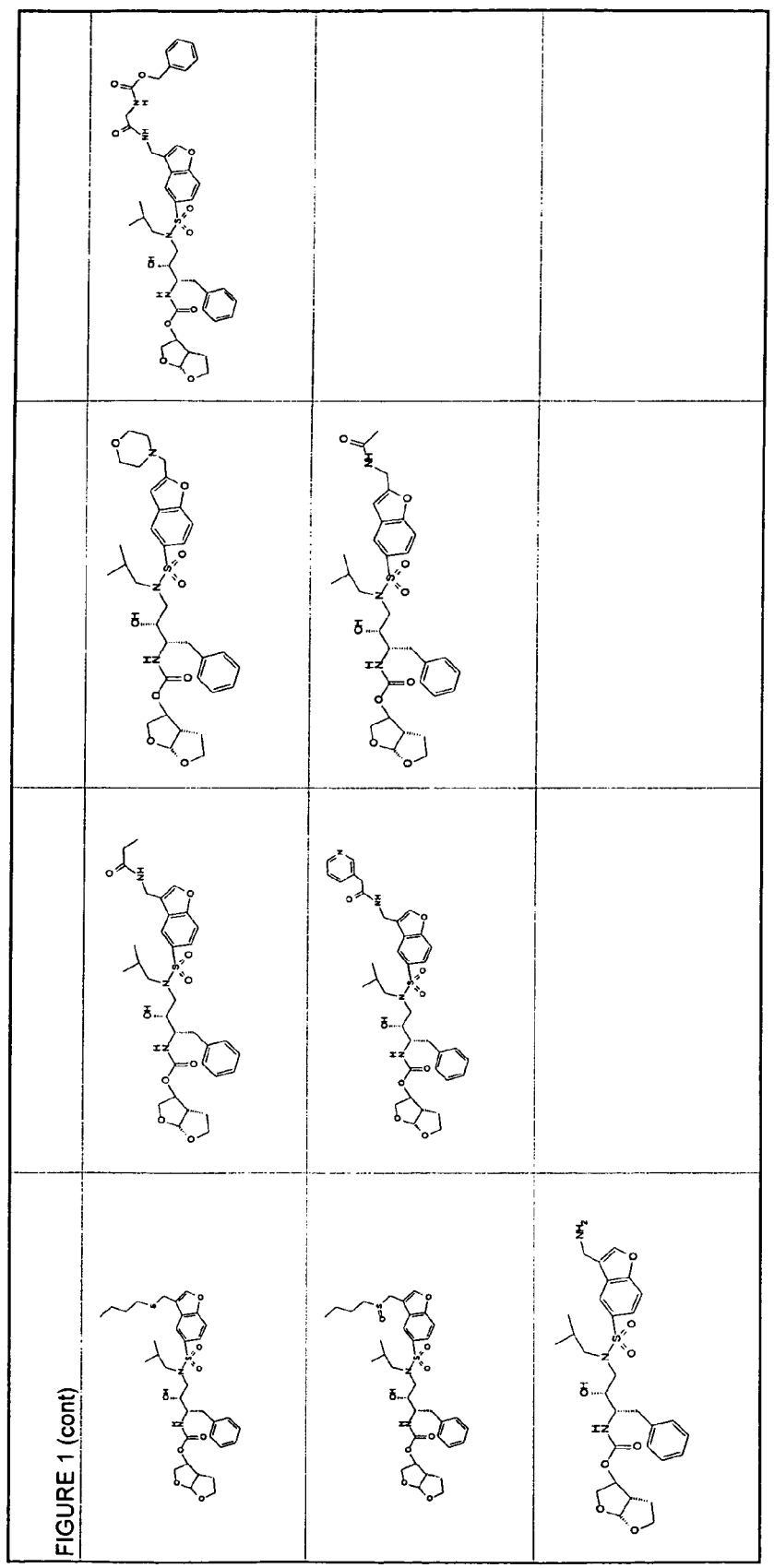

The invention provides novel 'resistance-repellent' retroviral protease inhibitors and compounds that inhibit metabolic degradation of retroviral protease inhibitors. More specifically, the invention provides compounds that are active against a wide cross-section of HIV strains. The invention further provides compounds that not only inhibit HIV protease, but that also inhibit one or more of the metabolic enzymes that degrade protease inhibitors in vivo. These compounds may be used for treating HIV/AIDS either alone, or in combination with other anti-HIV medicaments. In particular, the compounds that inhibit degradation of protease inhibitors may be used either as a sole protease inhibitor or in combination with one or more different protease inhibitors to inhibit degradation of the other inhibitor(s) and thereby maintain intracellular concentrations of the protease inhibitor(s) at a therapeutic level for a sustained period of time. Advantageously, patients treated under such a regimen also receive therapeutic doses of other anti-HIV medicaments such as reverse transcriptase inhibitors, cell fusion inhibitors and the like.

A 'resistance-repellent' protease inhibitor ("PI") is a compound that retains inhibitory activity, or potency, over a broad spectrum of related but non-identical retroviral proteases. Examples of resistance-repellent PIs include, but are not limited to, PIs that inhibit wild type HIV-1 protease derived from any lade B virus and 1) a wild type retroviral protease from one or more different retroviruses, such as HIV-2 protease; or 2) mutant HIV-1 proteases with single active site mutations at residues 30, 82 and 84; or 3) mutant HIV-1 proteases with single active site mutations at residues 47, 48, and 50; or 4) mutant HIV-1 proteases with double active site mutations at residues 82 and 84; or 5) mutant HIV-1 proteases with double active site mutations at residues 47 and 48, 47 and 50, or 48 and 50; or 6) mutant HIV-1 proteases with double active site mutations at residues 48 and 82, 48 and 90, or 82 and 90; or 7) mutant HIV-1 proteases with three or more active site mutations in any combination at residues 32, 47, 48, 50, 82, 84 or 90.

The term "pharmaceutically effective amount" refers to an amount effective in treating a virus infection, for example an HIV infection, in a patient either as monotherapy or in combination with other agents. The term "treating" as used herein refers to the alleviation of symptoms of a particular disorder in a patient or the improvement of an ascertainable measurement associated with a particular disorder. The term "prophylactically effective amount" refers to an amount effective in preventing a virus infection, for example an HIV infection, in a patient. As used herein, the term "patient" refers to a mammal, including a human.

The applicants have found that compounds having the general formula I are effective against a wide variety of PI-resistant HIV strains

X-A-B-A'-X'  I where X is a moiety that contains two or more hydrogen bond acceptors capable of interacting with the backbone NH atoms of residues 29 and 30 of an HIV protease, A is a 2-6 atom linker that contains at least one hydrogen bond acceptor that interacts with the flap water, and one hydrogen bond donor that interacts with the backbone CO atom of residue 27, B contains 1-3 atoms that can form hydrogen bonds with either or both carboxylate side chain oxygens of Asp25 and Asp 125 of said protease, A' is a 2-6 atom linker that contains at least one hydrogen bond acceptor that interacts with the flap water; and X' is a moiety that can form one or more hydrogen bonds with the backbone NH atoms of residues 129 and/or 130. Some compounds conforming to this general formula have been described and the present invention specifically excludes those compounds.

Resistance-repellent PIs should generally also retain inhibitory activity, or potency, over a broad spectrum of related but non-identical retroviruses. In particular, resistance-repellent PIs should inhibit all HIV-1 virus strains that contain a gene sequence of the protease region of the HIV-1 pol gene that is typified by one or more 'wild type' strains derived from clade B and: 1) HIV-1 virus strains that contain a gene sequence of the protease region of the HIV-1 pol gene derived from wild type, non-clade B viruses; or 2) wild type HIV-2 virus strains; or 3) HIV-1 virus strains derived from patients who are infected with HIV-1 that contain mutations in the protease gene.

In a preferred embodiment, the instant invention provides an HIV protease inhibitor represented by a formula:

X-A-B-A'-X' wherein,

X is a moiety that contains two or more hydrogen bond acceptors capable of interacting with the backbone NH atoms of residues 29 and 30 of said protease;

A is a 2-6 atom linker that contains at least one hydrogen bond acceptor that interacts with the flap water, and one hydrogen bond donor that interacts with the backbone CO atom of residue 27 of said protease;

B contains 1-3 atoms that can form hydrogen bonds with either or both carboxylate side chain oxygens of Asp25 and Asp 125 of said protease;

A' is a 2-6 atom linker that contains at least one hydrogen bond acceptor that interacts with a flap water of said protease;

X' is a moiety that can form one or more hydrogen bonds with the backbone NH atoms of residues 129 and/or 130 of said protease. Advantageously, X' comprises a bicyclic moiety which is a substituted or unsubstituted substituted or unsubstituted benzofuran, benzofuranone, benzisoxazole, benzindazole, chroman-4-one, and indazole.

In a particular embodiment the invention provides an HIV protease inhibitor represented by the formula I:

X-A-B-A'-X'  I wherein X is a moiety that contains two or more hydrogen bond acceptors capable of interacting with the backbone NH atoms of residues 29 and 30 of an HIV protease;

A is a 2-6 atom linker that contains at least one hydrogen bond acceptor that interacts with a flap water of said protease, and one hydrogen bond donor that interacts with the backbone CO atom of residue 27 of said protease;

B contains 1-3 atoms that can form hydrogen bonds with either or both carboxylate side chain oxygens of Asp25 and Asp 125 of said protease;

A' is a 2-6 atom linker that contains at least one hydrogen bond acceptor that interacts with the flap water of said protease; and X' is a moiety that can form one or more hydrogen bonds with the backbone NH atoms of residues 129 and/or 130 of said protease. Advantageously, X' comprises a bicyclic moiety which is a substituted or unsubstituted substituted or unsubstituted benzofuran, benzofuranone, benzisoxazole, benzindazole, chroman-4-one, and indazole.

In another embodiment, the invention provides an HIV protease inhibitor represented by a formula:

X-A-B-A'-X' wherein:
X is a 5-7 membered non-aromatic monocyclic heterocycle, wherein said heterocycle is optionally fused or bridged with one or more 3-7 membered non-aromatic monocyclic heterocycle to form a polycyclic system, wherein any of said heterocyclic ring systems contains one or more heteroatoms selected from O, N, S, or P; wherein any nitrogen forming part of the heterocycles may optionally be substituted by R2, R3, R6, R7 or O; wherein any sulfur may be optionally be substituted by one or two oxygen atoms; wherein any P may be optionally be substituted by one or more of O, NR2, or S, and any of said ring systems optionally contains 1 to 6 substituents selected from the group consisting of R2, R3, R5, and R6;

A is ZCZNH, ZCOCONH, ZS(O)$_2$NH, ZP(O)(V)NH, CONH, COCONH, S(O)$_2$NH, P(O)(V)NH, wherein Z is NR2, O, S, or C(R2)$_2$, and V is OR2 or NR2;

B is

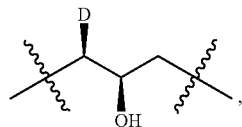

, wherein D is selected from alkyl, alkenyl, alkynyl, aryl, cycloalkyl, or aralkyl optionally substituted with one or more groups selected from alkyl, halo, nitro, cyano, CF$_3$, C3-C7 cycloalkyl, C5-C7 cycloalkenyl, R6, OR2, SR2, NHR2, OR3, SR3, NHR3, OR6, SR6, or NHR6;

A' is N(D')E', wherein D' is selected from alkyl, alkenyl, alkynyl, aryl, cycloalkyl, or aralkyl optionally substituted by alkyl, halo, nitro, cyano, CF$_3$, O-alkyl, or S-alkyl, and E' is —CO— or —SO$_2$—;

X' is selected from the group consisting of aryl and heteroaryl, which are optionally substituted with one or more of the following groups:
oxo, halo, OR3, OR6, OR7, OR2 provided R2 is not H or unsubstituted alkyl;
alkyl optionally substituted by R3, R5, R6 provided R5 is not halo;
C2-C6 alkenyl, C2-C6 alkynyl, C3-C8 cycloalkyl, C5-C8 cycloalkenyl, and heterocyclo, which groups may be optionally substituted with one or more substituents selected from R5;
aryl or heteroaryl, wherein said aryl or heteroaryl may be optionally substituted with one or more groups selected from the group consisting of aryl, heteroaryl, R2, R3, R4, and R6;
C3-C7 cycloalkyl substituted by R2, R3, R5, R6; provided R2 is not H;
CO$_2$H or R7; provided R8 is not H or unsubstituted alkyl;
NR8R8, NR7R8, NR7R7; provided R8 is not H or unsubstituted alkyl;
SO$_n$N(R8)$_2$, SO$_n$NR7R8, SR8, S(O)$_n$R8, provided R8 is not H or methyl;
and n is 1 or 2.
R is H or alkyl, aryl, alkenyl, alkynyl, cycloalkyl, cycloalkenyl, heterocyclo, heterocycloalkyl, heteroaryl; optionally substituted by halo, hydroxy, alkoxy, aryloxy, cycloalkoxy, heteroaryloxy, cyano, nitro, alkylthio, arylthio, cycloalkylthio, amino, or mono- or dialkylamino, mono- or diarylamino, mono- or di-cycloalkylamino, mono- or di-heteroarylamino, alkanoyl, cycloalkanoyl, aroyl, heteroaroyl, carboxamido, mono- or dialkylcarboxamido, mono- or diarylcarboxamido, sulfonamido, mono- or dialkylsulfonamido, mono- or diarylsulfonamido, alkylsulfinyl, alkylsulfonyl, arylsulfinyl, arylsulfonyl, cycloalkylsulfinyl, cycloalkylsulfonyl, heteroarylsulfinyl, heteroarylsulfonyl;

R2 is H or C1-C6 alkyl; optionally substituted by C2-C6 alkenyl, C2-C6 alkynyl, C3-C8 cycloalkyl, C5-C8 cycloalkenyl, heterocyclo; which groups may be optionally substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SONR, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCO$_n$R, =NNRS(O)$_n$N(R)$_2$, =NNRS(O)$_n$(R), or wherein two R groups together are —(CH$_2$)$_{4-6}$— optionally interrupted by one O, S, NH, N-(aryl), N-(aryl(lower alkyl)), N-(carboxy (lower alkyl)) or N-(optionally substituted C$_{1-2}$ alkyl) group;
or R2 is C1-C6 alkyl; substituted by aryl or heteroaryl; which groups may be optionally substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR;
or R2 is C1-C6 alkyl; optionally substituted by halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCOnR, =NNRS(O)nN(R)$_2$, or =NNRS(O)n(R);

R3 is C2-C6 alkenyl, C2-C6 alkynyl, C3-C8 cycloalkyl, C5-C8 cycloalkenyl, or heterocyclo; which groups may be optionally substituted with one or more substituents selected from the group consisting of halo, OR2, R2-OH, R2-halo, NO$_2$, CN, CO$_n$R2, C(O)N(R2)$_2$, C(O)N(R2)N(R2)$_2$, C(S)R2, C(S)N(R2)$_2$, S(O)nN(R2)$_2$, SR2, SO$_n$R2, N(R)$_2$, N(R2)CO$_n$R2, NR2S(O)$_n$R2, NR2C[=N(R2)]N(R2)$_2$, N(R2)N(R2)CO$_n$R2, NR2PO$_n$N(R2)$_2$, NR2PO$_n$OR2, oxo, =N—OR2, =N—N(R2)$_2$, =NR2, =NNRC(O)N(R2)$_2$, =NNR2C(O)$_n$R2, =NNR2S(O)$_n$N(R2)$_2$, or =NNR2S(O)$_n$(R2);

R4 is halo, OR8, R2-OH, R3-OH, R2-halo, R3-halo, NO$_2$, CN, CO$_n$R8, CO$_n$R8, CON(R8)$_2$, C(O)N(R8)N(R8)$_2$, C(S)R8, C(S)N(R8)$_2$, SO$_n$N(R8)$_2$, SR8, SO$_n$R8, N(R8)$_2$, N(R8)CO$_n$R8, NR8S(O)$_n$R8, NR8C[=N(R8)]N(R8)$_2$, N(R8)N(R8)CO$_n$R8, NR8PO$_n$N(R8)$_2$, NR8PO$_n$OR8, OC(O)R2, OC(S)R8, OC(O)N(R8)$_2$, OC(S)N(R8)$_2$, OPO$_n$(R8)$_2$;

R5 is OR8, N(R8)$_2$, NHOH, N(R8)COR8, NR8S(O)$_n$R8, NR8C[=N(R8)]N(R8)$_2$, N(R8)N(R8)C(O)R8, NR8PO$_n$N(R8)$_2$, NR8PO$_n$OR8, R2OH, R3-OH, R2-halo, R3-halo, CN, CO$_n$R8; provided that when n=2, R8 is not H; CON(R8)$_2$, C(O)N(R8)N(R8)$_2$, C(S)$_n$R8, C(S)N(R8)$_2$, S(O)$_n$R8, SO$_n$N(R8)$_2$, halo, NO$_2$, SR8, oxo, =N—OH, =N—OR8, =N—N(R8)$_2$, =NR8, =NNR8C(O)N(R8)$_2$, =NNR8C(O)$_n$R8, =NNR8S(O)$_n$N(R8)$_2$, or =NNR8S(O)$_n$(R8), or R3

R6 is aryl or heteroaryl, wherein said aryl or heteroaryl may be optionally substituted with one or more groups selected from aryl, heteroaryl, R2, R3, halo, OR2, R2OH, R2-halo, $NO_2$, CN, $CO_nR2$, $C(O)N(R2)_2$, $C(O)N(R2)N(R2)_2$, C(S)R2, $C(S)N(R2)_2$, $S(O)_nN(R2)_2$, SR2, $SO_nR2$, $N(R)_2$, $N(R2)CO_nR2$, $NR2S(O)_nR2$, $NR2C[=N(R2)]N(R2)_2$, $N(R2)N(R2)CO_nR$, $NR2PO_nN(R2)_2$, $NR2PO_nOR2$, OC(O)R2, OC(S)R2, $OC(O)N(R2)_2$, $OC(S)N(R2)_2$, $OPO_n(R2)_2$ R7 is $C(O)_nR8$; provided that when n=2; R8 is not H; C(S)R8, $C(O)N(R8)_2$, $C(S)N(R8)_2$, $S(O)_nR8$, $S(O)nN(R8)_2$;

R8 is R2, R3, or R6;

each n is independently 1 or 2;

its stereoisomeric forms; and its pharmacologically acceptable salts.

In one variation, X is

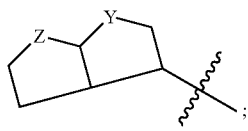

Y is O, NH, or S;

z is O, NH, or S; and wherein any ring carbon is optionally substituted by R2, R3, R5, or R6.

In another variation, X is

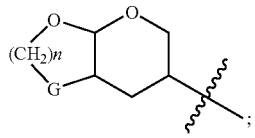

wherein

G is C, O, NR2, or S;

n is an integer between 1-2; and wherein any ring carbon is optionally substituted by R2, R3, R5, or R6.

In another variation, X is

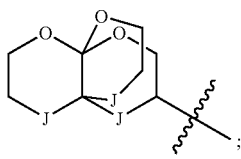

wherein

J is independently $CH_2$, or O, and wherein any ring carbon is optionally substituted by R2, R3, R5, or R6.

In yet another variation, X is

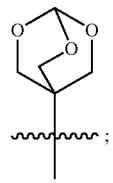

wherein any ring carbon is optionally substituted by R2, R3, R5, or R6.

In another variation, X is

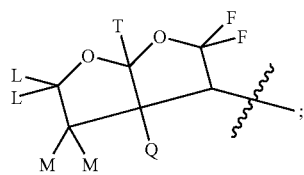

wherein each L is independently H, lower alkyl, oxo, or L forms a carbocyclic or heterocyclic ring with M;

each M is independently H, OH, chloro, fluoro, or M forms a carbocyclic or heterocyclic ring with Q, provided that if one M is OH, the other M is not OH;

Q is H, OH, amino, lower alkyl, alkylamino, alkoxy, halo, or forms a 3-7-membered carbocyclic or heterocyclic ring together with T;

each F is independently H, OH, lower alkyl, halo, or spirocylopropyl, provided that if one R is OH, the other R is not OH;

T is H or F, or T forms a carbocyclic or heterocyclic ring together with F.

In another variation, X is tetrahydrofurodihydrofuranyl, tetrahydrofurotetrahydrofuranyl, tetrahydropyranotetrahydrofuranyl or tetrahydropyranodihydrofuranyl;

A is OCONH;

B is

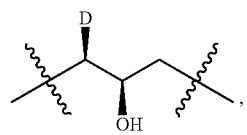

wherein D is selected from alkyl, alkenyl, alkynyl, aryl, cycloalkyl, or aralkyl optionally substituted with one or more groups selected from alkyl, halo, nitro, cyano, $CF_3$, C3-C7 cycloalkyl, C5-C7 cycloalkenyl, R6, OR2, SR2, NHR2, OR3, SR3, NHR3, OR6, SR6, or NHR6; and A' is N(D')E', wherein D' is alkyl, alkenyl, alkynyl aryl, cycloalkyl, or aralkyl optionally substituted by alkyl, halo, or $CF_3$, and E' is $—SO_2—$.

In another ariation, X is tetrahydrofurotetrahydrofuranyl;

A is OCONH;

B is

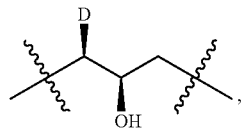

wherein D is benzyl; and

A' is N(D')E', wherein D' is isobutyl and E' is —SO$_2$—;

According to another variation, X is

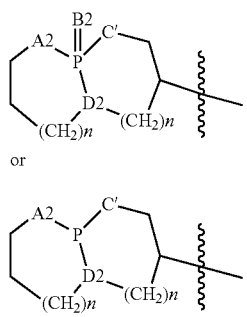

wherein A2, B2, and C' are each independently O, NR2, or S;

D2 is CH or N; and n is an integer between 1 and 2.

According to another variation, X is

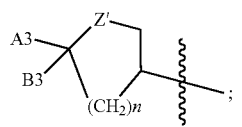

wherein

A3 is H, F or alkoxy;

B3 is F, alkoxy, lower alkyl, or A3 and B3 can form a 3-7 membered heterocyclic ring;

Z' is O, NR2, or S; and n is an integer between 1-3.

In one embodiment, X' is selected from the group that comprises

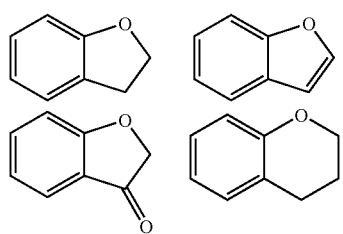

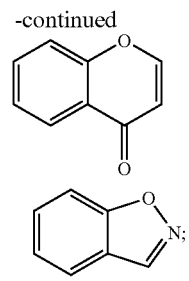

wherein said groups are optionally substituted with one or more of the following groups:

oxo, halo, OR3, OR6, OR7, OR2 provided R2 is not H or unsubstituted alkyl;

alkyl optionally substituted by R3, R5, R6 provided R5 is not halo;

C2-C6 alkenyl, C2-C6 alkynyl, C3-C8 cycloalkyl, C5-C8 cycloalkenyl, and heterocyclo, which groups may be optionally substituted with one or more substituents selected from R5;

aryl or heteroaryl, wherein said aryl or heteroaryl may be optionally substituted with one or more groups selected from the group consisting of aryl, heteroaryl, R2, R3, R4, and R6;

C3-C7 cycloalkyl substituted by R2, R3, R5, R6; provided R2 is not H;

CO$_2$H or R7; provided R8 is not H or unsubstituted alkyl;

NR8R8, NR7R8, NR7R7; provided R8 is not H or unsubstituted alkyl; and

SO$_n$N(R8)$_2$, SO$_n$NR7R8, SR8, S(O)$_n$R8, provided R8 is not H or methyl;

and n is 1 or 2.

In another embodiment, X' is selected from

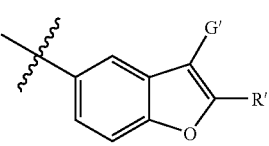

or

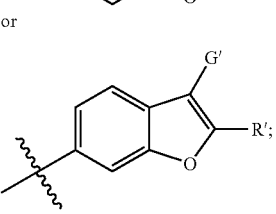

wherein

G' and R' cannot both be H;

G' and R' are each independently:

H or alkyl substituted by R3, R5, R6 provided R5 is not halo;

C2-C6 alkenyl, C2-C6 alkynyl, C3-C8 cycloalkyl, C5-C8 cycloalkenyl, and heterocyclo, which groups may be optionally substituted with one or more substituents selected from the group consisting of —OR2, C(O)N(R2)$_2$, S(O)$_n$N(R2)$_2$, CN, SR2, SO$_n$R2, COR2, CO$_2$R2 or NR2C(O)R2, R5, and R7;

aryl or heteroaryl, wherein said aryl or heteroaryl may be optionally substituted with one or more groups selected from the group consisting of aryl, heteroaryl, R2, R3, R4, and R6;

C3-C7 cycloalkyl substituted by R2, R3, R5, R6; provided R2 is not H;

CO₂H or R7 provided R2 is not H or unsubstituted alkyl; and

SO$_n$N(R8)$_2$, SO$_n$NR7R8, SR8, S(O)$_n$R8, provided R8 is not H or methyl; and n is 1 or 2.

Figure 2:
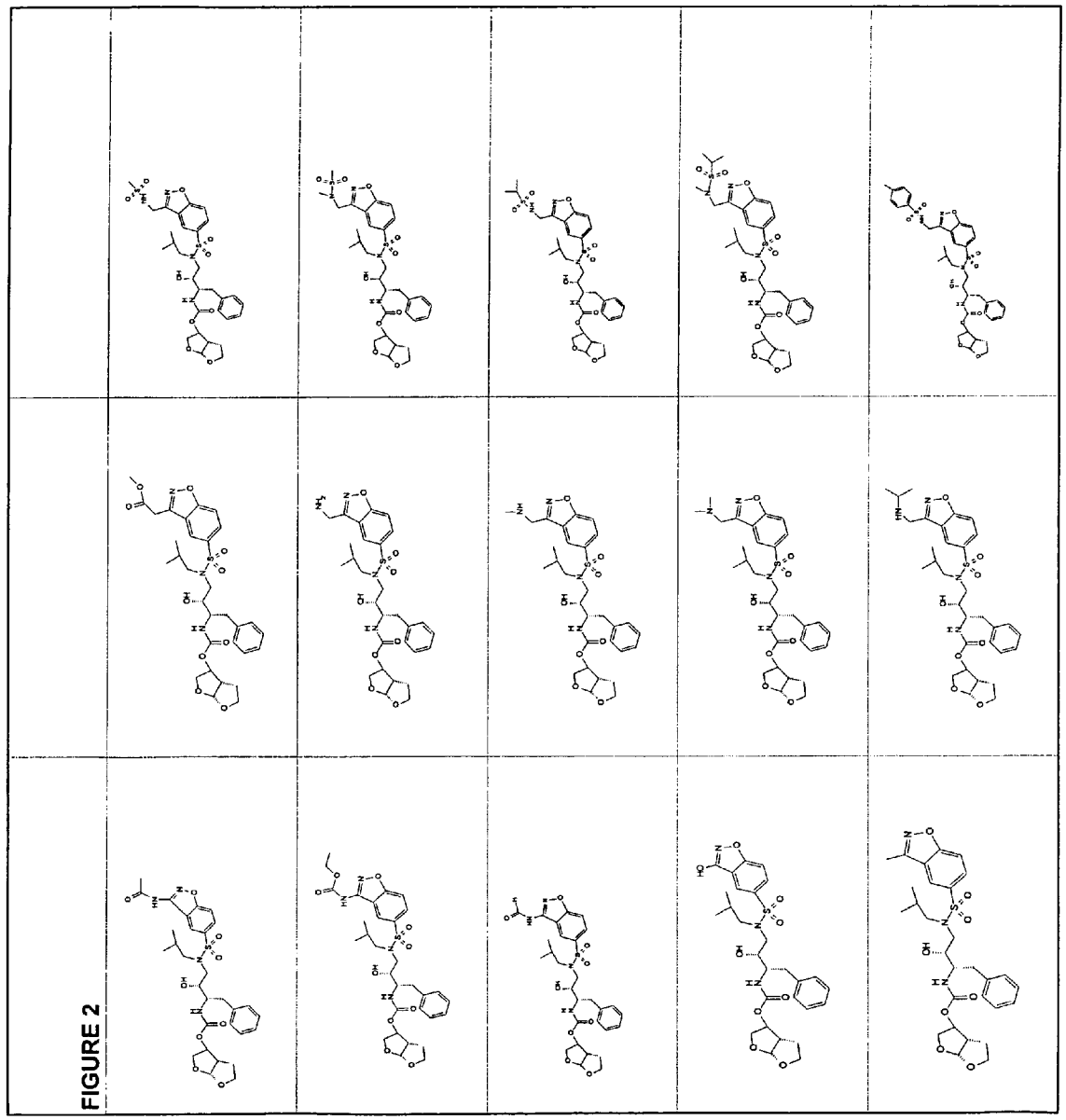
FIG. 2 shows the structures of benzisoxazole containing HIV protease inhibitors.
Figure 2:
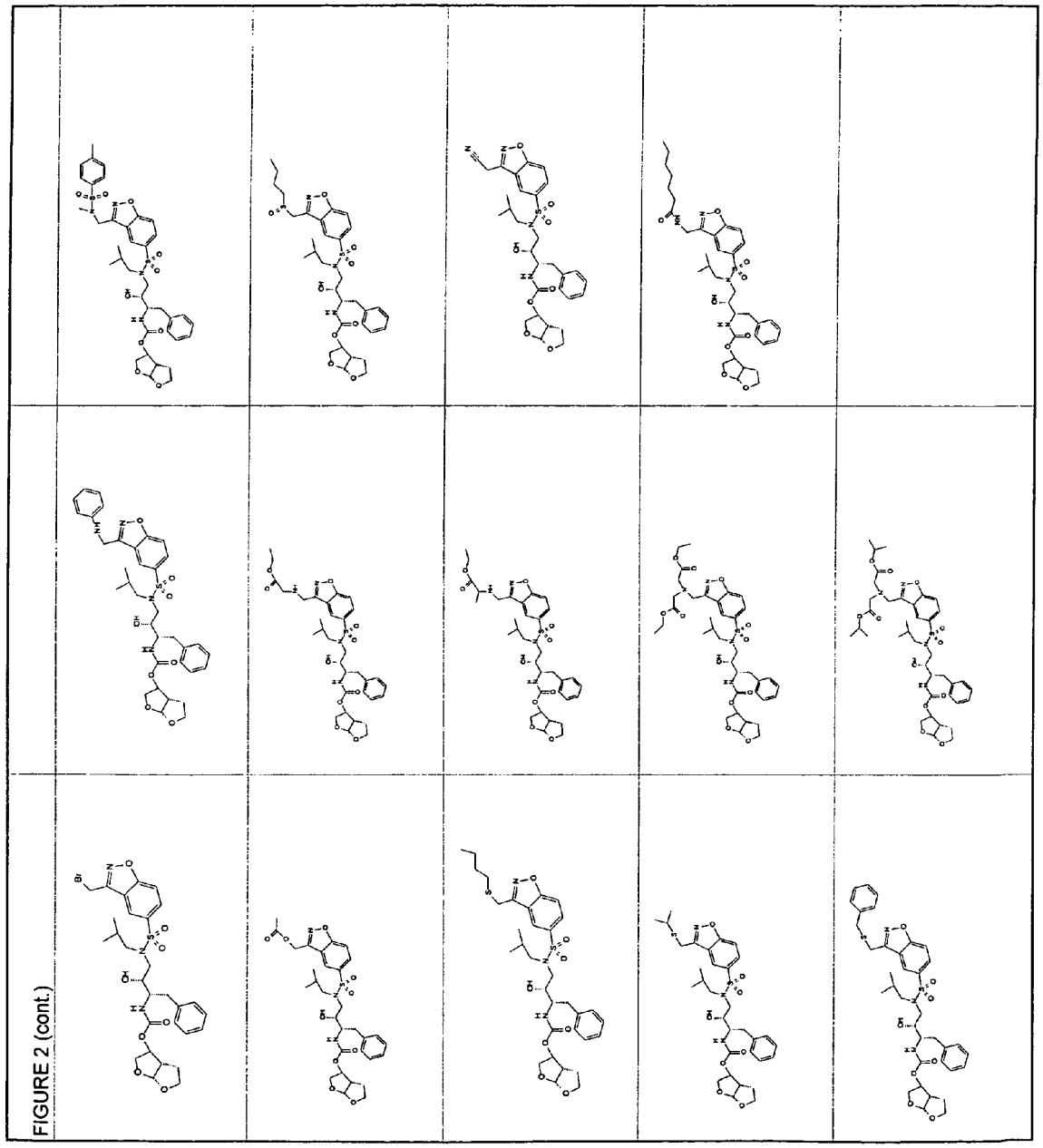
Figure 3:
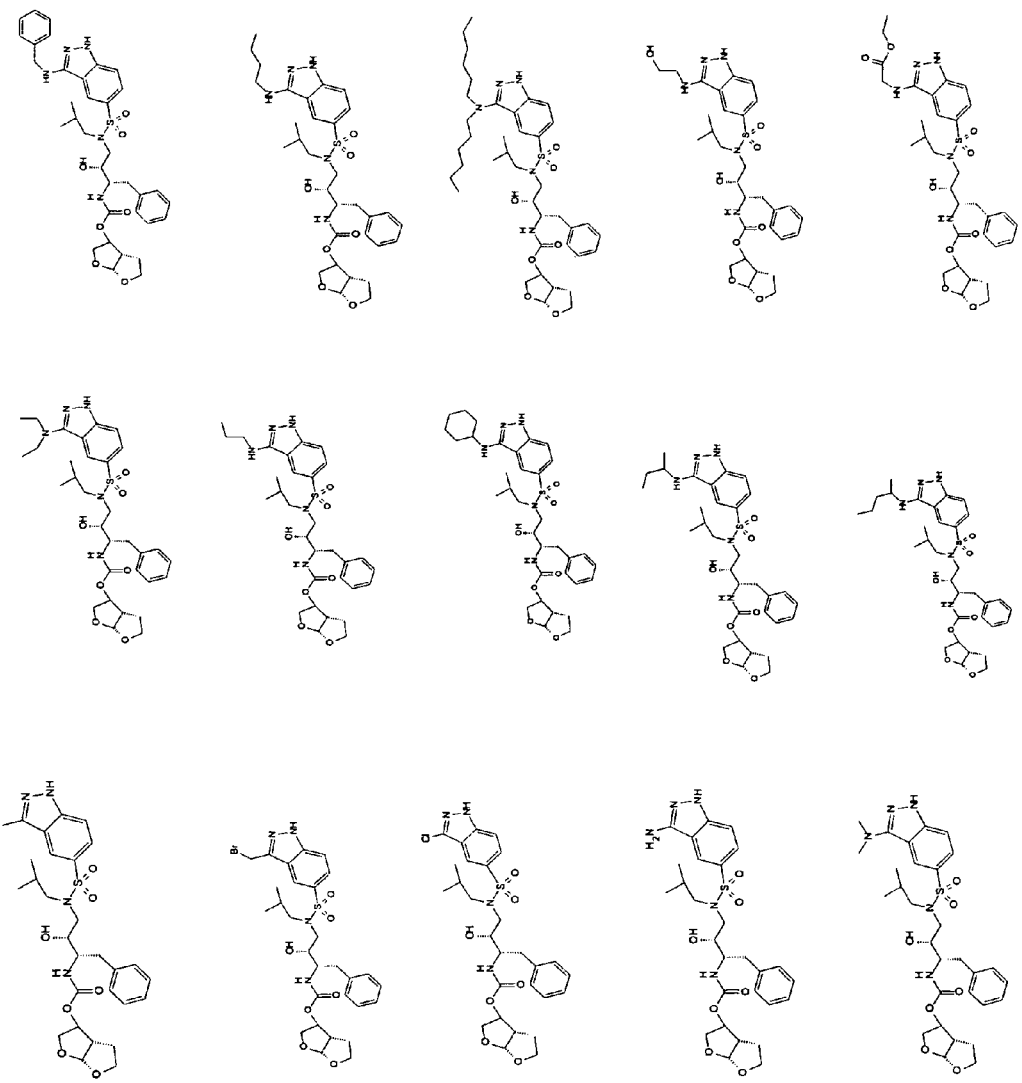
FIG. 3 shows the structures of indazole containing HIV protease inhibitors.
Figure 3:
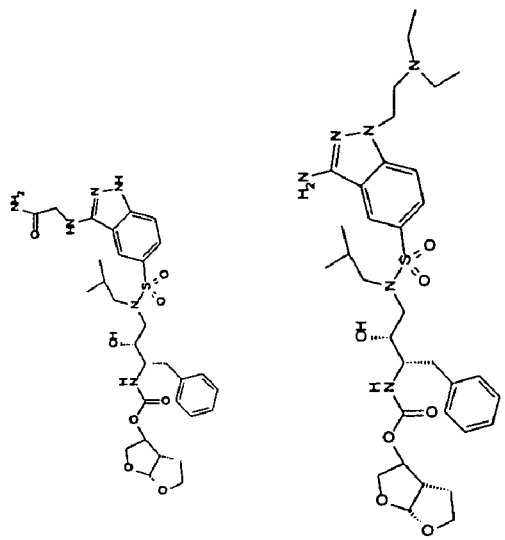
Figure 3:
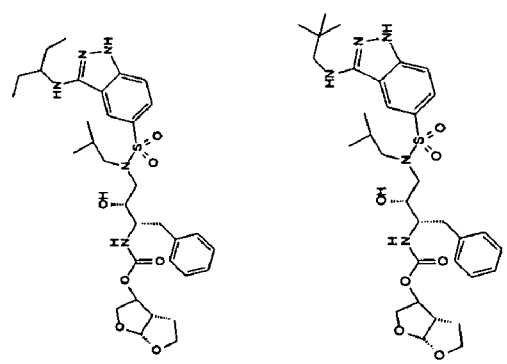
Figure 3:
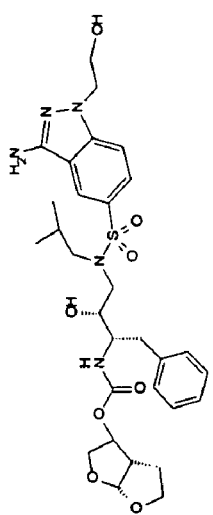

Particular compounds are selected from the group of compounds in FIGS. 1 to 3.

In another variation, preferably, X is

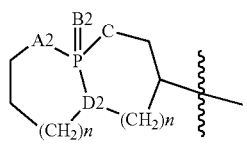

or

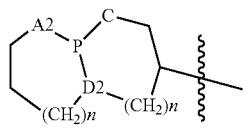

wherein A2, B2, and C are each independently O, NR2, or S;

D2 is CH or N; and wherein any ring carbon is optionally substituted by R2, R3, R5, or R6.

Preferably, X is

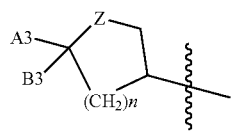

wherein

A3 is H, F or alkoxy;

B3 is F, alkoxy, lower alkyl, or A and B can form a 3-7 membered heterocyclic ring;

z is O, NR2, or S;

n is an integer between 1-3; and wherein any ring carbon is optionally substituted by R2, R3, R5, R6.

With regard to X, X may also be a 5-7 membered non-aromatic monocyclic heterocycle, wherein said heterocycle is optionally fused or bridged with one or more 3-7 membered non-aromatic monocyclic heterocycle to form a polycyclic system, wherein any of said heterocyclic ring systems contains one or more heteroatoms selected from O, N, S, or P; wherein any nitrogen forming part of the heterocycles may optionally be substituted by R2, R3, R6, R7 or O; wherein any sulfur may be optionally be substituted by one or two oxygen atoms; wherein any P may be optionally be substituted by one or more of O NR2, or S, and any of said ring systems optionally contains 1 to 6 substituents selected from the group consisting of R2, R3, R5, and R6.

X may also be

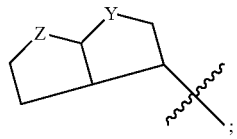

wherein, Y is O, NH, or S; Z is O, NH, or S; and wherein any ring carbon is optionally substituted by R2, R3, R5, or R6.

X may also be

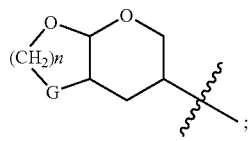

wherein G is C, O, NR2, or S; n is an integer between 1-2; and wherein any ring carbon is optionally substituted by R2, R3, R5, or R6.

X may also be

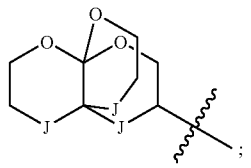

wherein J is independently CH$_2$, or O and wherein any ring carbon is optionally substituted by R2, R3, R5, or R6.

X may also be

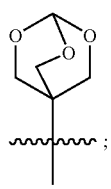

wherein any ring carbon is optionally substituted by R2, R3, R5, or R6.

X may also be

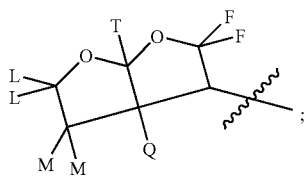

wherein each L is independently H, lower alkyl, oxo, or L forms a carbocyclic or heterocyclic ring with M; each M is independently H, OH, chloro, fluoro, or M forms a carbocyclic or heterocyclic ring with Q, provided that if one M is OH, the other M is not OH; Q is H, OH, amino, lower alkyl, alkylamino, alkoxy, halo, or forms a 3-7-membered carbocyclic or heterocyclic ring together with T; each F is independently H, OH, lower alkyl, halo, or spirocylopropyl, provided that if one R is OH, the other R is not OH; T is H or F, or T forms a carbocyclic or heterocyclic ring together with F.

X may also be

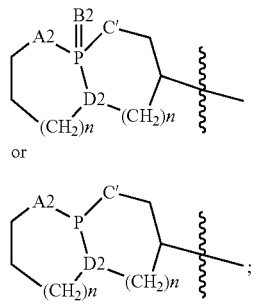

or wherein A2, B2, and C' are each independently O, NR2, or S; D2 is CH or N; and n is an integer between 1 and 2.

X may also be

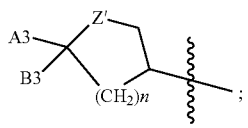

wherein A3 is H, F or alkoxy; B3 is F, alkoxy, lower alkyl, or A3 and B3 can form a 3-7 membered heterocyclic ring; Z' is O, NR2, or S; and n is an integer between 1-3.

X is preferably tetrahydrofurodihydrofuranyl, tetrahydrofuro-tetrahydrofuranyl, tetrahydropyrano-tetrahydrofuranyl or tetrahydropyranodihydrofuranyl. More preferably, X is tetrahydrofurotetrahydro-furanyl.

With regard to A, A may be ZCZNH, ZCOCONH, ZS(O)$_2$NH, ZP(O)(V)NH, CONH, COCONH, S(O)$_2$NH, P(O)(V)NH, wherein Z is NR2, O, S, or C(R2)$_2$, and V is OR2 or NR2. A is preferably OCONH.

With regard to B, B may be

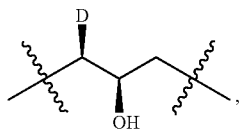

wherein D is selected from alkyl, alkenyl, alkynyl, aryl, cycloalkyl, or aralkyl optionally substituted with one or more groups selected from alkyl, halo, nitro, cyano, CF$_3$, C3-C7 cycloalkyl, C5-C7 cycloalkenyl, R6, OR2, SR2, NHR2, OR3, SR3, NHR3, OR6, SR6, or NHR6.

With regard to A', A' may be N(D')E', wherein D' is selected from alkyl, alkenyl, alkynyl, aryl, cycloalkyl, or aralkyl optionally substituted by alkyl, halo, nitro, cyano, CF$_3$, O-alkyl, or S-alkyl, and E' is —CO— or —SO$_2$—. Preferably, D' is alkyl, alkenyl, alkynyl aryl, cycloalkyl, or aralkyl optionally substituted by alkyl, halo, or CF$_3$, and E' is —SO$_2$—. More preferably, D' is isobutyl and E' is —SO$_2$—.

With regard to X', X' is selected from the group consisting of a substituted or unsubstituted benzofuran, benzofuranone, benzisoxazole, benzindazole, chroman-4-one, and indazole. When substituted, X' may be substituted with -Me, —CH$_2$NH$_2$, —CH$_2$NHCOMe, —CH$_2$-morpholine, —CH$_2$-piperidine, —CH$_2$NHBoc, —CH$_2$SO-Bu, —CH$_2$NHCO$_2$Et, —CH$_2$NHCOPh, —CH$_2$NHCBz, —CH$_2$NH(CH$_2$)$_2$-2-pyridine, —NH$_2$, —CH$_2$NH-ipropyl, —CH$_2$NHSO$_2$-i-propyl, —CH$_2$OAc, —CH$_2$CH(Me)CO$_2$Et, —CH$_2$NSO$_2$Me, —CH$_2$SOBu, —CH$_2$S-i-propyl, —CH$_2$NMeSO$_2$Me, —CH$_2$NMeTs, —NH(2-butyl), —NH(2-amyl), —NH-cyclohexyl, —NH-propyl, —NHCH$_2$Ph, —NH-3-amyl, —NH-butyl, and —NHCH$_2$-t-butyl.

Further, when substituted, X' may be substituted with aryl and heteroaryl, which are substituted with one or more of the following groups: OR3, OR6, OR7, OR2 provided R2 is not H or unsubstituted alkyl; alkyl substituted by R3, R5, R6 provided R5 is not halo; C2-C6 alkenyl, C2-C6 alkynyl, C3-C8 cycloalkyl, C5-C8 cycloalkenyl, and heterocyclo, which groups may be optionally substituted with one or more substituents selected from R5; aryl or heteroaryl, wherein said aryl or heteroaryl may be optionally substituted with one or more groups selected from the group consisting of aryl, heteroaryl, R2, R3, R4, and R6; C3-C7 cycloalkyl substituted by R2, R3, R5, R6; provided R2 is not H; CO$_2$H or R7; provided R8 is not H or unsubstituted alkyl; NR8R8, NR7R8, NR7R7; provided R8 is not H or unsubstituted alkyl; SO$_n$N(R8)$_2$, SO$_n$NR7R8, SR8, S(O)$_n$R8, provided R8 is not H or methyl; and n is 1 or 2.

Preferably, R is H or alkyl, aryl, alkenyl, alkynyl, cycloalkyl, cycloalkenyl, heterocyclo, heteroaryl; optionally substituted by halo, hydroxy, alkoxy, aryloxy, cycloalkoxy, heteroaryloxy, cyano, nitro, alkylthio, arylthio, cycloalkylthio, amino, or mono- or dialkylamino, mono- or diarylamino, mono- or di-cycloalkylamino, mono- or di-heteroarylamino, alkanoyl, cycloalkanoyl, aroyl, heteroaroyl, carboxamido, mono- or dialkylcarboxamido, mono- or diarylcarboxamido, sulfonamido, mono- or dialkylsulfonamido, mono- or diarylsulfonamido, alkylsulfinyl, alkylsulfonyl, arylsulfinyl, arylsulfonyl, cycloalkylsulfinyl, cycloalkylsulfonyl, heteroarylsulfinyl, heteroarylsulfonyl.

Preferably, R2 is H or C1-C6 alkyl; optionally substituted by C2-C6 alkenyl, C2-C6 alkynyl, C3-C8 cycloalkyl, C5-C8 cycloalkenyl, heterocyclo; which groups may be optionally substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCO$_n$R, =NNRS(O)$_n$N(R)$_2$, or =NNRS(O)$_n$(R); or R2 is C1-C6 alkyl; substituted by aryl or heteroaryl; which groups may be optionally substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR; or R2 is C1-C6 alkyl; optionally substituted by halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCOnR, =NNRS(O)nN(R)$_2$, or =NNRS(O)n(R).

Preferably, R3 is C2-C6 alkenyl, C2-C6 alkynyl, C3-C8 cycloalkyl, C5-C8 cycloalkenyl, or heterocyclo; which groups may be optionally substituted with one or more substituents selected from the group consisting of halo, OR2, R2-OH, R2-halo, NO$_2$, CN, CO$_n$R2, C(O)N(R2)$_2$, C(O)N(R2)N(R2)$_2$, C(S)R2, C(S)N(R2)$_2$, S(O)nN(R2)$_2$, SR2, SO$_n$R2, N(R)$_2$, N(R2)CO$_n$R2, NR2S(O)$_n$R2, NR2C[=N (R2)]N(R2)$_2$, N(R2)N(R2)CO$_n$R2, NR2PO$_n$N(R2)$_2$, NR2PO$_n$OR2, oxo, =N—OR2, =N—N(R2)$_2$, =NR2, =NNRC(O)N(R2)$_2$, =NNR2C(O)$_n$R2, =NNR2S(O)$_n$N(R2)$_2$, or =NNR2S(O)$_n$(R2).

Preferably, R4 is halo, OR8, R2-OH, R3-OH, R2-halo, R3-halo, NO$_2$, CN, CO$_n$R8, CO$_n$R8, CON(R8)$_2$, C(O)N(R8)N(R8)$_2$, C(S)R8, C(S)N(R8)$_2$, SOnN(R8)$_2$, SR8, SO$_n$R8, N(R8)$_2$, N(R8)CO$_n$R8, NR8 S(O)$_n$R8, NR8C[=N(R8)]N(R8)$_2$, N(R8)N(R8)CO$_n$R8, NR8PO$_n$N(R8)$_2$, NR8PO$_n$OR8, OC(O)R2, OC(S)R8, OC(O)N(R8)$_2$, OC(S)N(R8)$_2$, OPO$_n$(R8)$_2$.

Preferably, R5 is OR8, N(R8)$_2$, NHOH, N(R8)COR8, NR8S(O)$_n$R8, NR8C[=N(R8)]N(R8)$_2$, N(R8)N(R8)C(O)R8, NR8PO$_n$N(R8)$_2$, NR8PO$_n$OR8, R2OH, R3-OH, R2-halo, R3-halo, CN, CO$_n$R8; provided that when n=2, R8 is not H; CON(R8)$_2$, C(O)N(R8)N(R8)$_2$, C(S)$_n$R8, C(S)N(R8)$_2$, S(O)$_n$R8, SO$_n$N(R8)$_2$, halo, NO$_2$, SR8, oxo, =N—OH, =N—OR8, =N—N(R8)$_2$, =NR8, =NNR8C(O)N(R8)$_2$, =NNR8C(O)$_n$R8, =NNR8S(O)$_n$N(R8)$_2$, or =NNR8S(O)$_n$(R8), or R3.

Preferably, R6 is aryl or heteroaryl, wherein said aryl or heteroaryl may be optionally substituted with one or more groups selected from aryl, heteroaryl, R2, R3, halo, OR2, R2OH, R2-halo, NO$_2$, CN, CO$_n$R2, C(O)N(R2)$_2$, C(O)N(R2)N(R2)$_2$, C(S)R2, C(S)N(R2)$_2$, S(O)$_n$N(R2)$_2$, SR2, SO$_n$R2, N(R)$_2$, N(R2)CO$_n$R2, NR2S(O)$_n$R2, NR2C[=N(R2)]N(R2)$_2$, N(R2)N(R2)CO$_n$R2, NR2PO$_n$N(R2)$_2$, NR2PO$_n$OR2, OC(O)R2, OC(S)R2, OC(O)N(R2)$_2$, OC(S)N(R2)$_2$, OPO$_n$(R2)$_2$.

Preferably, R7 is C(O)$_n$R8; provided that when n=2; R8 is not H; C(S)R8, C(O)N(R8)$_2$, C(S)N(R8)$_2$, S(O)$_n$R8, S(O)nN(R8)$_2$.

Preferably, R8 is R2, R3, or R6; and Z is N, O, or S.

In another embodiment, the invention also provides compounds of the instant invention bound in a complex with wild type or drug resistant mutant forms of HIV-1 protease.

In still another embodiment, the invention also provides a composition comprising an inhibitor according to the instant invention and a pharmaceutically acceptable additive, excipient, or diluent.

In yet another embodiment, the invention also provides an pharmaceutical composition comprising an inhibitor according to the instant invention and another antiretroviral agent.

In a further embodiment, the invention also provides a composition comprising an inhibitor according to the instant invention and a second HIV inhibitor;

In a still further embodiment, the invention also provides an inhibitor according to the instant invention and an additional HIV protease inhibitor.

In yet another embodiment, the invention also provides an inhibitor according to the instant invention and an HIV reverse transcriptase inhibitor.

In still another embodiment, the invention also provides a method of treating a patient suffering from HIV infection, comprising administering to the patient one or more compounds and/or a composition according to the instant invention. The patient may suffer from a multi-drug resistant HIV infection.

In another embodiment, there is provided a method of inhibiting metabolic degradation of a retroviral protease inhibitor in a subject being treated with said inhibitor, comprising administering to said subject a degradation-inhibiting amount of a compound according to the above embodiments and variations.

In other embodiments, X' is

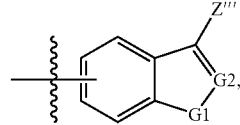

where G1 is NH or O;
where G2 is CZ" or N;
where Z" is selected from the group consisting of halogen, R2, R3, or R6;
where Z''' is selected from the group consisting of H or R2, R3, R6, halo, haloalkyl, C(R2)$_2$OR, C(R2)$_2$COR, C(R2)$_2$OCOR, C(R2)$_2$CO$_2$R, C(R2)$_2$N(R)$_2$, C(R2)$_2$SR, C(R2)$_2$SOR, C(R2)$_2$SO$_2$R, optionally substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR;

where X' is optionally substituted with one or more substituents, each independently selected from (a)-(h) as follows:
(a) OR3, OR6, OR7, OR2;
(b) alkyl substituted by R3, R5, R6;
(c) C2-C6 alkenyl, C2-C6 alkynyl, C3-C8 cycloalkyl, C5-C8 cycloalkenyl, and heterocyclyl, which groups may be optionally substituted with one or more substituents selected from R5;
(d) aryl or heteroaryl, where the aryl or heteroaryl may be optionally substituted with one or more groups selected from the group consisting of aryl, heteroaryl, R2, R3, R4 and R6;
(e) C3-C7 cycloalkyl substituted by R2, R3, R5 or R6;
(f) CO$_2$H or R7;
(g) NR8R8, NR7R8, NR7R7; and
(h) SO$_n$N(R8)$_2$, SO$_n$NR7R8, SR8, S(O)$_n$R8; and n is 1 or 2;

R is H or is selected from the group consisting of alkyl, aryl, alkenyl, alkynyl, cycloalkyl, cycloalkenyl, heterocyclo and heteroaryl; optionally substituted by halo, hydroxy, alkoxy, aryloxy, cycloalkoxy, heteroaryloxy, cyano, nitro, alkylthio, arylthio, cycloalkylthio, amino, or mono- or dialkylamino, mono- or diarylamino, mono- or di-cycloalkylamino, mono- or di-heteroarylamino, alkanoyl, cycloalkanoyl, aroyl, heteroaroyl, carboxamido, mono- or dialkylcarboxamido, mono- or diarylcarboxamido, sulfonamido, mono- or dialkylsulfonamido, mono- or diarylsulfonamido, alkylsulfinyl, alkylsulfonyl, arylsulfinyl, arylsulfonyl, cycloalkylsulfinyl, cycloalkylsulfonyl, heteroarylsulfinyl, heteroarylsulfonyl;

R2 is H or C1-C6 alkyl; optionally substituted by C2-C6 alkenyl, C2-C6 alkynyl, C3-C8 cycloalkyl, C5-C8 cycloalkenyl, heterocyclo; which groups may be optionally substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCO$_n$R, =NNRS(O)$_n$N(R)$_2$, or =NNRS(O)$_n$(R);

or R2 is C1-C6 alkyl; substituted by aryl or heteroaryl; which groups may be optionally substituted with one or more substituents selected from the group consisting of halo, OR, ROH, R-halo, NO$_2$, CN, CO$_n$R, CON(R)$_2$, C(S)R, C(S)N (R)₂, SO_nN(R)₂, SR, SO_nR, N(R)₂, N(R)CO_nR, NRS(O)_nR, NRC[=N(R)]N(R)₂, N(R)N(R)CO_nR, NRPO_nN(R)₂, NRPO_nOR;

or R2 is C1-C6 alkyl; optionally substituted by halo, OR, ROH, R-halo, NO₂, CN, CO_nR, CON(R)₂, C(S)R, C(S)N(R)₂, SO_nN(R)₂, SR, SO_nR, N(R)₂, N(R)CO_nR, NRS(O)_nR, NRC[=N(R)]N(R)₂, N(R)N(R)CO_nR, NRPO_nN(R)₂, NRPO_nOR, oxo, =N—OR, =N—N(R)₂, =NR, =NNRC(O)N(R)₂, =NNRCO_nR, =NNRS(O)_nN(R)₂, or =NNRS(O)_n(R);

R3 is C2-C6 alkenyl, C2-C6 alkynyl, C3-C8 cycloalkyl, C5-C8 cycloalkenyl, or heterocyclo; which groups may be optionally substituted with one or more substituents selected from the group consisting of halo, OR2, R2-OH, R2-halo, NO₂, CN, CO_nR2, C(O)N(R2)₂, C(O)N(R2)N(R2)₂, C(S)R2, C(S)N(R2)₂, S(O)_nN(R2)₂, SR2, SO_nR2, N(R)₂, N(R2)CO_nR2, NR2S(O)_nR2, NR2C[=N(R2)]N(R2)₂, N(R2)N(R2)CO_nR2, NR2PO_nN(R2)₂, NR2PO_nOR2, oxo, =N—OR2, =N—N(R2)₂, =NR2, =NNRC(O)N(R2)₂, =NNR2C(O)_nR2, =NNR2S(O)_nN(R2)₂, or =NNR2S(O)_n(R2);

R4 is selected from the group consisiting of halo, OR8, R2-OH, R3-OH, R2-halo, R3-halo, NO₂, CN, CO_nR8, CO_nR8, CON(R8)₂, C(O)N(R8)N(R8)₂, C(S)R8, C(S)N(R8)₂, SO₁N(R8)₂, SR8, SO_nR8, N(R8)₂, N(R8)CO_nR8, NR8S(O)_nR8, NR8C[=N(R8)]N(R8)₂, N(R8)N(R8)CO_nR8, NR8PO_nN(R8)₂, NR8PO_nOR8, OC(O)R2, OC(S)R8, OC(O)N(R8)₂, OC(S)N(R8)₂ and OPO_n(R8)₂;

R5 is selected from the group consisting of OR8, N(R8)₂, NHOH, N(R8)COR8, NR8S(O)_nR8, NR8C[=N(R8)]N(R8)₂, N(R8)N(R8)C(O)R8, NR8PO_nN(R8)₂, NR8PO_nOR8, R2OH, R3-OH, R2-halo, R3-halo, CN, CO_nR8; CON(R8)₂, C(O)N(R8)N(R8)₂, C(S)_nR8, C(S)N(R8)₂, S(O)_nR8, SO_nN(R8)₂, halo, NO₂, SR8, oxo, =N—OH, =N—OR8, =N—N(R8)₂, =NR8, =NNR8C(O)N(R8)₂, =NNR8C(O)_nR8, =NNR8S(O)_nN(R8)₂, or =NNR8S(O)_n(R8) and R3;

R6 is aryl or heteroaryl, where the aryl or heteroaryl may be optionally substituted with one or more groups selected from aryl, heteroaryl, R2, R3, halo, OR2, R2OH, R2-halo, NO₂, CN, CO_nR2, C(O)N(R2)₂, C(O)N(R2)N(R2)₂, C(S)R2, C(S)N(R2)₂, S(O)_nN(R2)₂, SR2, SO_nR2, N(R)₂, N(R2)CO_nR, NRS(O)_nR2, NR2C[=N(R2)]N(R2)₂, N(R2)N(R2)CO_nR2, NR2PO_nN(R2)₂, NR2PO_nOR2, OC(O)R2, OC(S)R2, OC(O)N(R2)₂, OC(S)N(R2)₂, OPO_n(R2)₂;

R7 is selected from the group consisting of C(O)_nR8; C(S)R8, C(O)N(R8)₂, C(S)N(R8)₂, S(O)_nR8 and S(O)nN(R8)₂;

R8 is R2, R3, or R6;

R9 is alkyl optionally substituted by R3, R5, R6; C2-C6 alkenyl, C2-C6 alkynyl, C3-C8 cycloalkyl, C5-C8 cycloalkenyl, and heterocyclo, which groups may be optionally substituted with one or more substituents selected from the group consisting of —OR2, C(O)N(R2)₂, S(O)_nN(R2)₂, CN, SR2, SO_nR2, COR2, CO₂R2 or NR2C(O)R2, R5, and R7; aryl or heteroaryl, where the aryl or heteroaryl may be optionally substituted with one or more groups selected from the group consisting of aryl, heteroaryl, R2, R3, R4, and R6; C3-C7 cycloalkyl optionally substituted by R2, R3, R5, R6; CO₂H or R7; NR3R3, NR6R6, NR7R7, NR3R6, NR6R7, NR3R7, NR2R3, NR2R6, NR2R7, NR2R2; SO_nN(R8)₂, SO_nNR7R8, SR8, S(O)_nR8; and n is 1 or 2; SO_nN(R2)₂, SO_nN(R3)₂, SO_nN(R6)₂, SO_nN(R7)₂, SO_nNR2R3, SO_nNR2R6, SO_nNR2R7, SO_nNR3R6, SO_nNR3R7, SO_nNR6R7; S(O)_mR2, S(O)_mR3, S(O)_mR6; and m is 0, 1 or 2; and each n is independently 1 or 2.

In other embodiments, X' is selected from

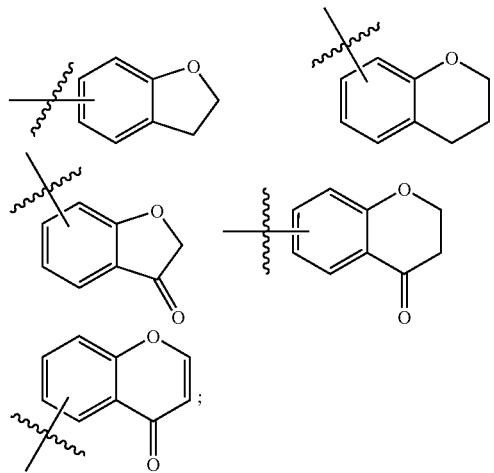

where the groups are optionally substituted with one or more of the following groups:

oxo, halo, OR3, OR6, OR7, OR2 provided R2 is not H or unsubstituted alkyl;

alkyl optionally substituted by R3, R5, R6 provided R5 is not halo;

C2-C6 alkenyl, C2-C6 alkynyl, C3-C8 cycloalkyl, C5-C8 cycloalkenyl, and heterocyclo, which groups may be optionally substituted with one or more substituents selected from R5;

aryl or heteroaryl, where the aryl or heteroaryl may be optionally substituted with one or more groups selected from the group consisting of aryl, heteroaryl, R2, R3, R4, and R6;

C3-C7 cycloalkyl substituted by R2, R3, R5, R6; provided 2 is not H;

CO₂H or R7; provided R8 is not H or unsubstituted alkyl;

NR8R8, NR7R8, NR7R7; provided R8 is not H or unsubstituted alkyl; and

SO_nN(R8)₂, SO_nNR7R8, SR8, S(O)_nR8, provided R8 is not H or methyl; and n is 1 or 2.

In the embodiments described above, Z''' may be H and Z'' may be CH₂Cl, CH₂Br, CH₂I, CH₂OR, CH₂NH₂, CH₂N(R)₂, CH₂N(R)COR or CH₂N(R)CO₂R. R may be H or C₁-C₆ alkyl.

In the embodiments described above, Z'' may be H and Z''' may be selected from the group consisting of H, C(R2)₂-halo, C(R2)₂R, C(R2)₂OR, C(R2)₂COR, C(R2)₂OCOR, C(R2)₂CO₂R, C(R2)₂N(R)₂, C(R2)₂SR, C(R2)₂SOR, C(R2)₂SO₂R, C(R2)₂N(R)CO_nR, C(R2)₂NRS(O)_nR, C(R2)₂NRC[=N(R)]N(R)₂, C(R2)₂N(R)N(R)CO_nR, C(R2)₂C(S)R, C(R2)₂C(S)N(R)₂, and C(R2)₂SO_nN(R)₂.

In specific embodiments, Z''' may be selected from the group consisting of H, Me, CH2OH, CH2OAc, CH2OMe, CH2NHiPr, CH2NH2, CH2S(O)Bu, CH2S-iPr, CH2OCOtBu, CH2NHCH2CH2OMe, CH2NHCOiPr, CH2NHCOPh, CH2NHCO2Pr, CH2NHCOMe, CH2-4-Morpholino, CH2-1-piperidino, CH2NHBoc, CH2NHCO2Et, CH2NHCOEt, CH2NHSO2iPr, CH2NHCbz, CH2NH(CH2)2-2-pyridyl, CH2NHCO-3-pyridyl, CH2NHCOCH2SCH2Ph, CH2NHCOCH2S(O)CH2Ph, CH2NHCO-2-furanyl, CH2N(CO2Et)CH2CH2OMe, NHCH(Me)CO2Et, CH2NHSO2Et, CH2NHSO2Me, CH2NMeSO2Me, CH2NMeTs, CH2NHCO2iPr, CH2OCOiPr, CH2-1-imidazole, CH2NHCH2CH2SEt, CH2N((CH2)2OMe)SO2Et, CH2NHCH2CF2CF3, CH2NHCH2CF3, CH2NHCH2CH2OPh, CH2NHBu, CH2NHCH2Ph, CH2SCH2CF3, CH2NHCOCF3, CH2NHcyclopentyl, CH2NHCH2CH2NHBoc, CH2NH(CH2)3-1-pyrrolidine-2-one, CH2NHCH2cyclohexyl, CH2NHCH2-2-pyridyl, CH2NHCH2-4-(2-methylthiazole), CH2SO2Me, CH2NHCOCF2CF3, CH2OCH2CF3, CH2N(Ac)CH2CF3, and CH2NHCH2-5-benzofuranyl.

The inhibitor may be selected from the group of compounds in FIGS. 1-3.

The invention also provides a compound as described above, bound in a complex with wild type or drug resistant mutant forms of HIV-1 protease.

The invention also provides a pharmaceutical composition comprising an effective amount of an inhibitor as described above and a pharmaceutically acceptable additive, excipient, or diluent. The composition may also comprise another antiretroviral agent, such as a second HIV inhibitor. The additional HIV inhibitor(s) may be an HIV protease inhibitor and/or an HIV reverse transcriptase inhibitor.

The invention also provides a method of treating a patient suffering from HIV infection, for example multi-drug resistant HIV infection, comprising administering to the patient a compound or composition as described above. 25. A method of treatment according to claim 24 where the patient is suffering from a.

The invention further provides a method of inhibiting metabolic degradation of a retroviral protease inhibitor in a subject being treated with the inhibitor, comprising administering to the subject a degradation-inhibiting amount of a compound as described above. The compound may be administered substantially contemporaneously with the inhibitor and/or prior to administration of the inhibitor.

The invention also provides HIV protease inhibitors having the structure

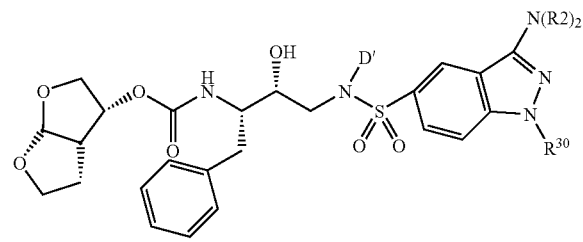

where each R2 may be the same or different, and R2 is H or C1-C6 alkyl; optionally substituted by C2-C6 alkenyl, C2-C6 alkynyl, C3-C8 cycloalkyl, C5-C8 cycloalkenyl, heterocyclo; which groups may be optionally substituted with one or more substituents selected from the group consisting of halo, OR, ROH, R-halo, $NO_2$, CN, $CO_nR$, $CON(R)_2$, C(S)R, C(S)N(R)$_2$, $SO_nN(R)_2$, SR, $SO_NR$, $N(R)_2$, $N(R)CO_nR$, $NRS(O)_nR$, $NRC[=N(R)]N(R)_2$, $N(R)N(R)CO_nR$, $NRPO_nN(R)_2$, $NRPO_nOR$, oxo, $=N—OR$, $=N—N(R)_2$, $=NR$, $=NNRC(O)N(R)_2$, $=NNRCO_nR$, $=NNRS(O)_nN(R)_2$, or $=NNRS(O)_n(R)$;

or R2 is C1-C6 alkyl; substituted by aryl or heteroaryl; which groups may be optionally substituted with one or more substituents selected from the group consisting of halo, OR, ROH, R-halo, $NO_2$, CN, $CO_nR$, $CON(R)_2$, C(S)R, C(S)N(R)$_2$, $SO_nN(R)_2$, SR, $SO_nR$, $N(R)_2$, $N(R)CO_nR$, $NRS(O)_nR$, $NRC[=N(R)]N(R)_2$, $N(R)N(R)CO_nR$, $NRPO_nN(R)_2$, $NRPO_nOR$;

or R2 is C1-C6 alkyl; optionally substituted by halo, OR, ROH, R-halo, $NO_2$, CN, $CO_nR$, $CON(R)_2$, C(S)R, C(S)N(R)$_2$, $SO_nN(R)_2$, SR, $SO_nR$, $N(R)_2$, $N(R)CO_nR$, $NRS(O)_nR$, $NRC[=N(R)]N(R)_2$, $N(R)N(R)CO_nR$, $NRPO_nN(R)_2$, $NRPO_nOR$, oxo, $=N—OR$, $=N—N(R)_2$, $=NR$, $=NNRC(O)N(R)_2$, $=NNRCO_nR$, $=NNRS(O)_nN(R)_2$, or $=NNRS(O)_n(R)$;

and where D' is selected from the group consisting of alkyl, alkenyl, alkynyl, aryl, cycloalkyl and aralkyl, and is optionally substituted by alkyl, halo, nitro, cyano, $CF_3$, halo-C1-C6 alkyl, O-alkyl, or S-alkyl.

As used herein, pharmaceutically acceptable derivatives of a compound include salts, esters, enol ethers, enol esters, acetals, ketals, orthoesters, hemiacetals, hemiketals, solvates, hydrates, tautomers or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug.

By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392). As used herein, prodrugs include phosphonates.

Also included in the present application are one or more of the various polymorphs of the compounds. A crystalline compound disclosed in the present application may have a single or may have multiple polymorphs, and these polymorphs are intended to be included as compounds of the present application. Also, where a single polymorph is noted, the polymorph may change or interconvert to one or more different polymorphs, and such polymorph or polymorph mixtures are included in the present application.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to a-amino acids which are racemic or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

It is also to be understood that the compounds provided herein may have tautomeric forms. All such tautomeric forms are included within the scope of the instant disclosure. For example, a 3-enamino-2-oxindole where the amino group of the enamine has a hydrogen substituent has the tautomeric form of a 3-imino-2-hydroxyindole.

The term "alkyl", alone or in combination with any other term, refers to a straight-chain or branch-chain saturated aliphatic hydrocarbon radical containing the specified number of carbon atoms, or where no number is specified, preferably from 1 to about 15 and more preferably from 1 to about 10 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, preferably from 2-10 carbon atoms and more preferably, from 2-6 carbon atoms. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like.

The term "alkynyl," alone or in combination with any other term, refers to a straight-chain or branched-chain hydrocarbon radical having one or more triple bonds containing the specified number of carbon atoms, or where no number is specified, preferably from 2 to about 10 carbon atoms. Examples of alkynyl radicals include, but are not limited to, ethynyl, propynyl, propargyl, butynyl, pentynyl and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl," alone or in combination with any other term, refers to a carbocyclic aromatic radical (such as phenyl or naphthyl) containing the specified number of carbon atoms, preferably from 6-15 carbon atoms, and more preferably from 6-10 carbon atoms, optionally substituted with one or more substituents selected from alkyl, alkoxy, (for example methoxy), nitro, halogen, (for example chloro), amino, carboxylate and hydroxy. Examples of aryl radicals include, but are not limited to phenyl, p-tolyl, 4-hydroxyphenyl, 1-naphthyl, 2-naphthyl, indenyl, indanyl, azulenyl, fluorenyl, anthracenyl and the like.

The term "aralkyl", alone or in combination, means an alkyl radical as defined above in which one hydrogen atom is phenyl, benzyl, 2-phenylethyl and the like.

The term "aralkoxy carbonyl", alone or in combination, means a radical of the formula —C(O)—O-aralkyl in which the term "aralkyl" has the significance given above. An example of an aralkoxycarbonyl radical is benzyloxycarbonyl.

The term "aryloxy", alone or in combination, means a radical of the formula aryl-O— in which the term "aryl" has the significance given above.

The term "alkanoyl", alone or in combination, means an acyl radical derived from an alkanecarboxylic acid, examples of which include acetyl, propionyl, butyryl, valeryl, 4-methylvaleryl, and the like.

The term "aryloxyalkanoyl" means an acyl radical of the formula aryl-O-alkanoyl wherein aryl and alkanoyl have the significance given above.

The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-phenylbutyryl, (1-naphthyl)acetyl, 4-chlorohydrocinnamoyl, 4-aminohydrocinnamoyl, 4-methoxyhydrocinnamoyl, and the like.

The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "aminocarbonyl" alone or in combination, means an amino-substituted carbonyl(carbamoyl) group derived from an amino-substituted carboxylic acid wherein the amino group can be a primary, secondary or tertiary amino group continuing substituents selected from hydrogen, alkyl, aryl, aralkyl, cycloalkyl, cycloalkylalkyl radicals and the like.

The term "aminoalkanoyl" means an acyl radical derived from an amino substituted alkanecarboxylic acid wherein the amino group can be a primary, secondary or tertiary amino group containing substituents selected from the group consisting of hydrogen, cycloalkyl, cycloalkylalkyl radicals and the like, examples of which include N,N-dimethylaminoacetyl and N-benzylaminoacetyl.

The term "carbocycle" refers to a non-aromatic stable 3- to 8-membered carbon ring which may be saturated, monounsaturated or poly-unsaturated. The carbocycle may be attached at any endocyclic carbon atom which results in a stable structure. Preferred carbocycles have 5-7 carbons.

The term "cycloalkyl", alone or in combination, means an alkyl radical which contains from about 3 to about 8 carbon atoms and is cyclic. Examples of such cycloalkyl radicals include cyclopropyl, cyclobutyl, cyclopentyl, cyclohexyl and the like.

The term "cycloalkylalkyl" means an alkyl radical as defined above which is substituted by a cycloalkyl radical containing from about 3 to about 8, preferably from about 3 to about 6, carbon atoms.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl, 2-acetamido-1,2,3,4-tetrahydro-2-naphthoyl.

The term "cycloalkylalkoxycarbonyl" means an acyl group derived from a cycloalkylalkoxycarboxylic acid of the formula cycloalkylalkyl-O—COOH wherein cycloalkylalkyl has the significance given above.

The term "heterocyclyl" or "heterocycle" refers to a stable 3-7 membered monocyclic heterocyclic ring or 8-11 membered bicyclic heterocyclic ring which is either saturated or partially unsaturated, and which may be optionally benzo-fused if monocyclic and which is optionally substituted on one or more carbon atoms by halogen alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e., +N—) by oxido and which is attached via a carbon atom. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocyclyl radical may be attached at any endocyclic carbon or heteroatom which results in the creation of a stable structure. Preferred heterocycles include 5-7 membered monocyclic heterocycles and 8-10 membered bicyclic heterocycles. Examples of such groups imidazolinoyl, imidazolidinyl, indazolinolyl, perhydropyridazyl, pyrrolinyl, pyrrolidinyl, piperidinyl, pyrazolinyl, piperazinyl, morpholinyl, thiamorpholinyl, thiazolidinyl, thiamorpholinyl sulfone, oxopiperidinyl, oxopyrrolidinyl, oxoazepinyl, tetrahydropyranyl, tetrahydrofuranyl, dioxolyl, dioxinyl, benzodioxolyl, dithiolyl, tetrahydrothienyl, sulfolanyl, dioxanyl, dioxolanyl, tetahydrofurodihydrofuranyl, tetrahydropyranodihydrofuranyl, dihydropyranyl, tetradyrofurofuranyl and tetrahydropyranofuranyl.

The term heteroaryl refers to a stable 5-6 membered monocyclic or 8-11 membered bicyclic aromatic heterocycles where heterocycles is as defined above. Non-limiting examples of such groups include imidazolyl, quinolyl, isoquinolyl, indolyl, indazolyl, pyridazyl, pyridyl, pyrrolyl, pyrazolyl, pyrazinyl, quinoxolyl, pyranyl, pyrimidinyl, furyl, thienyl, triazolyl, thiazolyl, carbolinyl, tetrazolyl, benzofuranoyl, thiamorpholinyl sulfone, oxazolyl, benzoxazolyl, benzimidazolyl, benzthiazolyl, oxopiperidinyl, oxopyrrolidinyl, oxoazepinyl, azepinyl, isoxazolyl, isothiazolyl, furazanyl, thiazolyl, thiadiazolyl, oxathiolyl.

The term "heterocyclylalkanoyl" is an acyl radical derived from a heterocyclyl-substituted alkane carboxylic acid wherein heterocyclyl has the significance given above.

The term "heterocyclyloxycarbonyl" means an acyl group derived from heterocyclyl-O—COOH wherein heterocyclyl is as defined above.

The term "heterocyclylalkoxycarbonyl" means an acyl radical derived from heterocyclyl-substituted alkane-O—COOH wherein heterocyclyl has the significance given above.

The term "heteroaryloxycarbonyl" means an acyl radical derived from a carboxylic acid represented by heteroaryl-O—COOH wherein heteroaryl has the significance given above.

The term "halogen" means fluorine, chlorine, bromine or iodine.

The term haloalkyl means an alkyl with one or more of its hydrogens replaced by halogens. Haloalkyl also include per-haloalkyl groups or partially halogenated alkyl groups, including for example, halo-C1-C6 alkyl groups. Non-exclusive examples of haloalkyls include —CF3, —CF2CF3, —CH2CF3, and the like.

The term "thioalkyl" means an alkyl radical having at least one sulfur atom, wherein alkyl has the significance given above. An example of a thioalkyl is $CH_3SCH_3$. The corresponding sulfoxide and sulfone of this thioalkyl $CH_3S(O)CH_3$ and $CH_3S(O)_2CH_3$ respectively. Unless expressly stated to the contrary, the terms "—$SO_2$—" and "—$S(O)_2$—" as used herein refer to a sulfone or sulfone derivative (i.e., both appended groups linked to the S), and not a sulfinate ester.

The term "substituted", whether preceded by the term "optionally" or not, and substitutions contained in formulas of this invention, refer to the replacement of one or more hydrogen radicals in a given structure with the radical of a specified substituent. Examples of substituents include, but are not limited to, aldehydes, aliphatic, (C1-10)alkyl, (C1-10) alkylene, amino, amide, aryl, bicycloalkyl, carboxyl, carbonyl group, ester group, halo, oxo, hydroxy, nitro, and the like. Also, each of the substituents may be further substituted. When more than one position in a given structure may be substituted with more than one substituent selected from a specified group, the substituents may be either the same or different at every position (for example, the moiety —N(R2) (R2)). Typically, when a structure may be optionally substituted, 0-3 substitutions are preferred, and 0-1 substitutions are more preferred. Most preferred substituents are those which enhance protease inhibitory activity or intracellular antiviral activity in permissive mammalian cells or immortalized mammalian cell lines, or which enhance deliverability by enhancing solubility characteristics or enhancing pharmacokinetic or pharmacodynamic profiles as compared to the unsubstituted compound. Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

This invention also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

As used herein, the compounds of this invention, including the compounds of formula I are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Salts derived from appropriate bases include alkali metal (e.g., sodium), alkaline earth metal (e.g., magnesium), ammonium and N—($C_{1-4}$alkyl)$_4^+$ salts.

The compounds of this invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

The instant compounds may be prepared according to synthetic methods set forth, for example, in U.S. Pat. No. 6,319,946 to Hale et al., and in *J. Med. Chem.* 36, 288-291 (93), the disclosures of which are incorporated herein by reference in their entireties, together with procedures of the type described below.

A representative synthesis can be used when preparing variations of X'. Here instead of being sulfonylated, amino alcohol 2 can be N-protected by a group that is not removed by removing P, for example P is Boc and P' is Carbobenzyloxy. The di-protected 7 is then deprotected to give 8 which is reacted as above to give 9. Following deprotection of 9 various X' groups may be introduced via the activated sulfonyl derivatives in a similar fashion as described above.

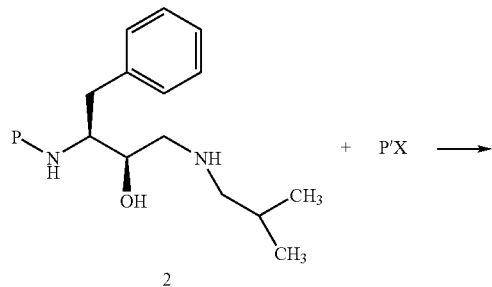

2

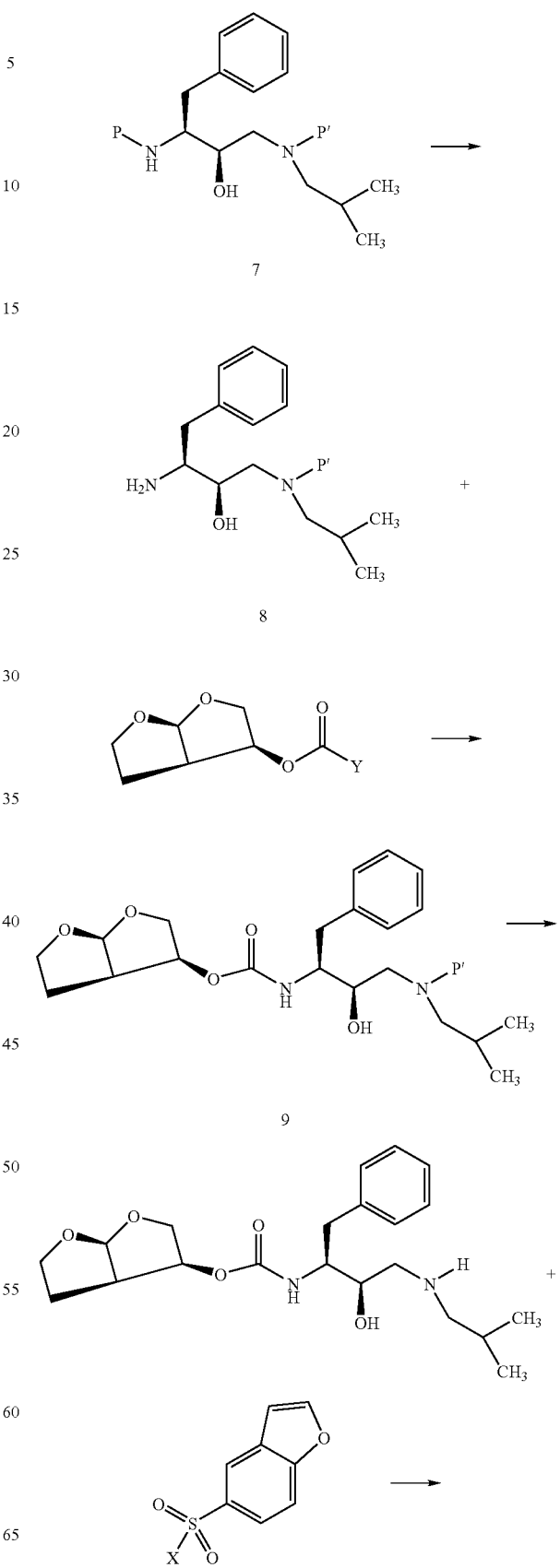

-continued

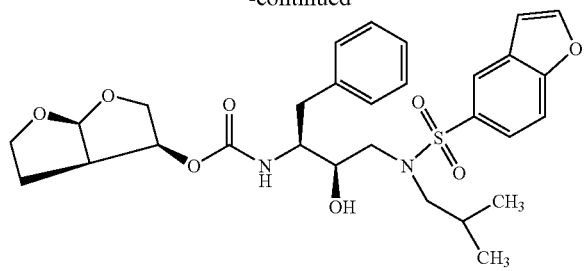

An example of a synthesis of X with a third fused ring is shown below. This olefinic tricyclic system has already been described by McElvain, et al. *JACS* 77, 5601 (1955). Anti-Markownikov addition of water across the double bond using standard conditions can provide the target alcohol. It is noteworthy that these authors showed that the unsubstituted tricyclic system had unusual acid stability, which may help prolong the activity of our target compounds.

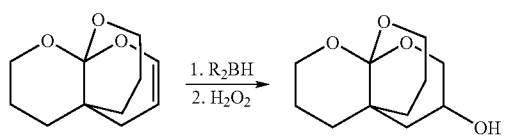

The synthesis of a bicyclo[2.2.0] system can proceed in a similar fashion as has been described Padias, et al. *J.O.C.* 52, 5305 (1987) for a homologous analog. R can either be H or a protecting group such as benzyl that can subsequently be removed under standard conditions. Protic (e.g. toluenesulfonic) or Lewis (e.g. scandium triflate) acids can be used for the condensation.

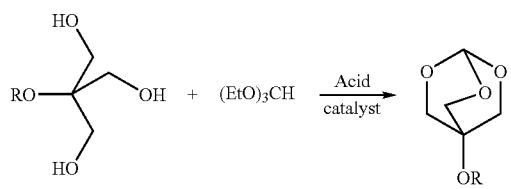

The synthesis of a representative phosphorus containing bicycle described herein. Similar chemistry has been described by Arnold, et al. *In Ang. Chem.* 70, 539 (1958) and Dankiewicz, et al. in *JACS* 101, 7712 (1979). The R group in the target shown may either be H

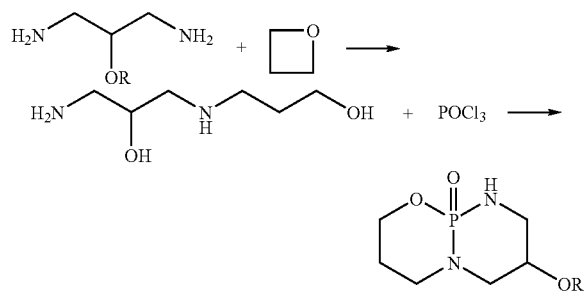

or a protecting group such as benzyl that can subsequently be removed.

Additional synthetic methods for preparing the compounds of the invention are provided below.

Pharmaceutical Compositions

The compounds of the present invention may be used in the form of pharmaceutically acceptable salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

Other pharmaceutically acceptable salts include a salt with an inorganic base, organic base, inorganic acid, organic acid, or basic or acidic amino acid. Inorganic bases which form the instant pharmaceutically acceptable salts include alkali metals such as sodium or potassium, alkali earth metals such as calcium and magnesium or aluminum, and ammonia. Organic bases which form the instant pharmaceutically acceptable salts include trimethylamine, triethylamine, pyridine, picoline, ethanolamine, diethanolamine, triethanolamine, dicyclohexylamine. Inorganic acids which form the instant pharmaceutically acceptable salts include hydrochloric acid, hydroboric acid, nitric acid, sulfuric acid, and phosphoric acid. Organic acids appropriate to form the salt include formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Basic amino acids to form the salt include arginine, lysine and ornithine. Acidic amino acids to form the salt include aspartic acid and glutamic acid.

The instant invention also contemplates compositions which can be administered orally or non-orally in the form of, for example, granules, powders, tablets, capsules, syrup, suppositories, injections, emulsions, elixir, suspensions or solutions, by mixing these effective components, individually or simultaneously, with pharmaceutically acceptable carriers, excipients, binders, diluents or the like.

The compounds of the present invention-are useful in the treatment of individuals infected by HIV and for the prophylaxis of these individuals. The present invention may be useful in the treatment of mammals infected with viruses whose existence is mediated by, or depends upon, the protease enzyme. Conditions which may be prevented or treated with the compounds of the present invention, especially conditions associated with HIV and other pathogenic retroviruses, include AIDS, AIDS-related complex (ARC), progressive generalized lymphadenopathy (POL), as well as chronic CNS diseases caused by retroviruses, such as, for example HIV-mediated dementia and multiple sclerosis.

As a solid formulation for oral administration, the instant composition may be in the form of powders, granules, tablets, pills and capsules. In these cases, the instant compounds can be mixed with at least one additive, for example, sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. These formulations can contain, as in conventional cases, further additives, for example, an inactive diluent, a lubricant such as magnesium stearate, a preservative such as paraben or sorbic acid, an anti-oxidant such as ascorbic acid, tocopherol or cysteine, a disintegrator, a binder, a thickening agent, a buffer, a sweetener, a flavoring agent and a perfuming agent. Tablets and pills can further be prepared with enteric coating.

As used herein, "non-orally" includes subcutaneous injection, intravenous injection, intramuscular injections, intraperitoneal injection or instillation. Injectable preparations, for example, sterile injectable aqueous suspensions or oil suspensions can be prepared by known procedures in the fields concerned, using a suitable dispersant or wetting agent and suspending agent. The sterile injections may be, for example, a solution or a suspension, which is prepared with a non-toxic diluent administrable non-orally, such as an aqueous solution, or with a solvent employable for sterile injection. Examples of usable vehicles or acceptable solvents include water, Ringer's solution and an isotonic aqueous saline solution. Further, a sterile non-volatile oil can usually be employed as solvent or suspending agent. A non-volatile oil and a fatty acid can be used for this purpose, including natural or synthetic or semi-synthetic fatty acid oil or fatty acid, and natural or synthetic mono- or di- or tri-glycerides.

The instant pharmaceutical compositions may be formulated for nasal aerosol or inhalation and may be prepared as solutions in saline, and benzyl alcohol or other suitable preservatives, absorption promoters, fluorocarbons, or solubilizing or dispersing agents.

Rectal suppositories can be prepared by mixing the drug with a suitable vehicle, for example, cocoa butter and polyethylene glycol, which is in the solid state at ordinary temperatures, in the liquid state at temperatures in intestinal tubes and melts to release the drug.

Examples of liquid preparations for oral administration include pharmaceutically acceptable emulsions, syrups, elixirs, suspensions and solutions, which may contain an inactive diluent, for example, water.

The pharmaceutical composition may be easily formulated for topical administration with a suitable ointment containing one or more of the instant compounds suspended or dissolved in a carrier, which include mineral oil, liquid petroleum, white petroleum, propylene glycol, polyoxyethylene polyoxypropylene compound, emulsifying wax and water. In addition, topical formulations can be formulated with a lotion or cream containing the active compound suspended or dissolved in a carrier. Suitable carriers include mineral oil, sorbitan monostearate, polysorbate 60, cetyl esters wax, cetearyl alcohol, 2-octyldodecanol, benzyl alcohol and water.

Dosages of the instant compounds are dependent on age, body weight, general health conditions, sex, diet, dose interval, administration routes, excretion rate, combinations of drugs and conditions of the diseases treated, while taking these and other necessary factors into consideration. Generally, dosage levels of between about 10 μg per day to about 5000 mg per day, preferably between about 100 mg per day to about 1000 mg per day of the compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy.

The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

While these dosage ranges can be adjusted by a necessary unit base for dividing a daily dose, as described above, such doses are decided depending on the diseases to be treated, conditions of such diseases, the age, body weight, general health conditions, sex, diet of the patient then treated, dose intervals, administration routes, excretion rate, and combinations of drugs, while taking these and other necessary factors into consideration. For example, a typical preparation will contain from about 0.05% to about 95% active compound (w/w). Preferably, such preparations contain from about 10% to about 80% active compound. The desired unit dose of the composition of this invention is administered once or multiple times daily.

Accordingly, a preferred embodiment the instant invention also contemplates compositions and formulations comprising one or more of the instant compounds in combination with one or more other HIV protease inhibitors, reverse transcriptase inhibitors, or non-nucleoside reverse transcriptase inhibitors.

The compounds of this invention may be administered to an uninfected or HIV-infected patient either as a single agent or in combination therapy with other anti-viral agents which interfere with the replication cycle of HIV in order to increase the therapeutic effect of these compounds. Thus, the present invention also relates to compositions comprising a compound of the present invention, and another antiretroviral compound as a combined preparation for simultaneous, separate or sequential use in treatment of retroviral infections, in particular, in the treatment of infections with multi-drug resistant retroviruses. Thus, to combat or treat HIV infections, or the infection and disease associated with HIV infections, such as Acquired Immunodeficiency Syndrome (ADS) or AIDS Related Complex (ARC), the compounds of this invention may be co-administered in combination with for instance, binding inhibitors, such as, for example, dextran sulfate, suramine, polyanions, soluble CD4, PRO-542, BMS-806; fusion inhibitors, such as, for example, T20, T1249, 5-helix, D-peptide ADS-Ji; co-receptor binding inhibitors, such as, for example, AMD 3100, AMD-3465, AMD7049, AMD3451 (Bicyclams), TAK 779; SHC-C (SCH351125), SHC-D, PRO-140RT inhibitors, such as, for example, foscamet and prodrugs; nucleoside RTIs, such as, for example, AZT, 3TC, DDC, DDI, D4T, Abacavir, FTC, DAPD, dOTC, DPC 817; nucleotide RTIs, such as, for example, PMEA, PMPA (tenofovir); NNRTIs, such as, for example, nevirapine, delavirdine, efavirenz, 8 and 9-Cl TIBO (tivirapine), loviride, TMC-125, dapivirine, MKC-442, UC 781, UC 782, Capravirine, DPC 961, DPC963, DPC082, DPC083, calanolide A, SJ-1366, TSAO, 4"-deaminated TSAO, MV150, MV026048; RNAse H inhibitors, such as, for example, SPI093V, PD126338; TAT inhibitors, such as, for example, RO-5-3335, K12, K37; integrase inhibitors, such as, for example, L 708906, L 731988, S-1360; protease inhibitors, such as, for example, amprenavir and prodrug GW908, ritonavir, nelfinavir, saquinavir, indinavir, lopinavir, palinavir, .BMS 186316, atazanavir, DPC 681, DPC 684, tipranavir, AG1776, mozenavir, GS3333, KNI-413, KNI-272, L754394, L756425, LG-71350, PD161374, PD173606, PD177298, PD178390, PD178392, PNU 140135, TMC114, maslinic acid, U-140690; glycosylation inhibitors, such as, for example, castanospermine, deoxynojirimycine.

The combination may in some cases provide a synergistic effect, whereby viral infectivity and its associated symptoms may be prevented, substantially reduced, or eliminated completely.

The compounds of the present invention may also be administered in combination with immunomodulators (e.g., bropirimine, anti-human alpha interferon antibody, IL-2, methionine enkephalin, interferon alpha, HE-2000 and naltrexone) with antibiotics (e.g., pentamidine isothiorate) cytokines (e.g. Th2), modulators of cytokines, chemokines or the receptors thereof (e.g. CCR5) or hormones (e.g. growth hormone) to ameliorate, combat, or eliminate HIM infection and its symptoms.

Such combination therapy in different formulations may be administered simultaneously, separately or sequentially. Alternatively, such combination may be administered as a single formulation, whereby the active ingredients are released from the formulation simultaneously or separately.

The compounds of the present invention may also be administered in combination with modulators of the metabolism following application of the drug to an individual. These modulators include compounds that interfere with the metabolism at cytochromes, such as cytochrome P450. Some modulators inhibit cytochrome P450. It is known that several isoenzymes exist of cytochrome P450, one of which is cytochrome P450 3A4. Ritonavir is an example of a modulator of metabolism via cytochrome P450. Such combination therapy in different formulations, may be administered simultaneously, separately or sequentially. Alternatively, such combination maybe administered as a single formulation, whereby the active ingredients are released from the formulation simultaneously or separately. Such modulator may be administered at the same or different ratio as the compound of the present invention. Preferably, the weight ratio of such modulator vs. a compound of the present invention (modulator:compound of the present invention) is 1:1 or lower, more preferably the ratio is 1:3 or lower, suitably the ratio is 1:10 or lower, more suitably the ratio is 1:30 or lower.

In order to enhance the solubility and/or the stability of the compounds of formula I in pharmaceutical compositions, α, β, or γ cyclodextrins or their derivatives may be employed. Also co-solvents such as alcohols may improve the solubility and/or the stability of the compounds of formula I in pharmaceutical compositions. In the preparation of aqueous compositions, addition salts of the subject compounds may be more suitable due to their increased water solubility.

Appropriate cyclodextrins are α, β, or γ-cyclodextrins (CDs) or ethers and mixed ethers thereof wherein one or more of the hydroxy groups of the anhydroglucose units of the cyclodextrin are substituted with C1-C6alkyl, such as methyl, ethyl or isopropyl, e.g. randomly methylated β-CD; hydroxy C16 alkyl, particularly hydroxyethyl, hydroxypropyl or hydroxybutyl; carboxy C1-C6alkyl, particularly carboxymethyl or carboxyethyl; C1-C6alkyl-carbonyl, particularly acetyl; C1-C6 alkyloxycarbonylC1-C6alkyl or carboxyC16alkyloxyC1-C6alkyl, particularly carboxymethoxypropyl or carboxyethoxypropyl; C1-C6alkylcarbonyloxyC1-C6alkyl, particularly 2-acetyloxypropyl. Especially noteworthy as complexants and/or solubilizers are β-CD, randomly methylated β-CD, 2,6-dimethyl-β-CD, 2.-hydroxyethyl-β-CD, 2-hydroxyethyl-γ-CD, hydroxy-propyl-γ-CD and (2-carboxymethoxy)propyl-β-CD, and in particular 2-hydroxy-propyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The present compounds may be formulated in combination with a cyclodextrin or a derivative thereof as described in EP-A-721,331. Although the formulations described therein are with antifungal active ingredients, they are equally relevant for formulating compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. The formulations may also be rendered more palatable by adding pharmaceutically acceptable sweeteners and/or flavors.

Other convenient ways to enhance the solubility of the compounds of the present invention in pharmaceutical compositions are described in WO 94/05263, WO 98/42318, EP-A-499,299 and WO 97/44014, all incorporated herein by reference.

More in particular, the present compounds may be formulated in a pharmaceutical composition comprising a therapeutically effective amount of particles consisting of a solid dispersion comprising a compound of formula I, and one or more pharmaceutically acceptable water-soluble polymers.

The term "a solid dispersion" defines a system in a solid state comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C.

Preferred water-soluble polymers are hydroxypropyl methylcelluloses (HPMC). HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxypropyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation.

It may further be convenient to formulate the present compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

The present compounds may also be incorporated in hydrophilic polymers and applied as a film over many small beads, thus yielding a composition with good bioavailability which can conveniently be manufactured and which is suitable for preparing pharmaceutical dosage forms for oral administration. The beads comprise a central, rounded or spherical core, a coating film of a hydrophilic polymer and an antiretroviral agent and a seal-coating polymer layer. Materials suitable for use as cores are pharmaceutically acceptable and have appropriate dimensions and firmness. Examples of such materials are polymers, inorganic substances, organic substances, saccharides and derivatives thereof. The route of administration may depend on the condition of the subject, co-medication and the like.

The instant compounds and compositions retain inhibitory activity, or potency, over a broad spectrum of related but non-identical retroviral proteases. Accordingly, in another preferred embodiment, the instant invention includes methods for treating or preventing viral infections. Treating or preventing refers to alleviating or hindering symptoms or effects of a viral infection in an infected animal, such as a mammal, particularly a human. Treating includes prophylaxis as well as the treatment of viral infections or symptoms of viral infections. The instant methods comprise treating an animal with a therapeutically effective amount of a compound or composition according to the instant invention. According to a preferred embodiment, the viral infection is an HIV infection, preferably an mdrHIV infection.

Moreover, the instant compounds and compositions are particularly effective as inhibitors against drug resistant and mdrHIV strains and multi-drug resistant HIV proteases (mdrPR). Accordingly, in another preferred embodiment, the instant invention provides methods for inhibiting HIV protease, particularly drug resistant and multi-drug resistant HIV proteases (mdrPR), with a therapeutically effective amount of a compound or composition according to the instant invention.

In relation to the above, the instant compounds may be used in vaccines for protecting individuals against viral, specifically, mdrHIV infections. As such, the instant compounds may be employed as protease inhibitors as conventionally used in vaccines. In this regard, one or more of the instant compounds may be combined with a pharmaceutically acceptable adjuvant conventionally employed in vaccines and administered in prophylactically effective amounts to protect individuals over an extended period time against HIV infection.

The present invention also relates to novel compositions and a method for improving the pharmacokinetics of drugs which are metabolized by cytochrome P450 monooxygenase. In addition, the present invention relates to a novel composition and a method for inhibiting retroviral proteases and in particular for inhibiting human immunodeficiency virus (HIV) protease and a composition and a method for inhibiting a retroviral infection, in particular an HIV infection.

Use of Compounds of the Invention for "Boosting"

Surprisingly, it has been found that certain compounds of the invention are not only potent inhibitors of HIV proteases, but also potently inhibit the cytochrome P450 isozyme (CYP3A4) that is mainly responsible for oxidative degradation of HIV protease inhibitors. In particular, compounds having a benzofuran moiety are potent inhibitors of CYP3A4.

In light of this activity, these compounds are degraded only slowly and have extended durations of action in vivo. Moreover, these compounds are useful for "boosting" the activities of other HIV protease inhibitors by inhibiting CYP3A4-mediated degradation of those inhibitors.

In this connection, the present invention provides a method of improving the pharmacokinetics of a drug (or a pharmaceutically acceptable salt thereof) which is metabolized by cytochrome P450 monooxygenase comprising coadministering a compound of the instant invention or a pharmaceutically acceptable salt thereof. When administered in combination, the two therapeutic agents can be formulated as separate compositions which are administered at the same time or different times, or the two therapeutic agents can be administered as a single composition. In one aspect, when therapeutic agents are administered in combination, the dosage used may be at the therapeutic dosage or at sub-therapeutic dosages.

Drugs which are metabolized by cytochrome P450 monooxygenase and which benefit from coadministration with a compound of the instant invention include, but are not limited to, ritonavir, the immunosuppressants cyclosporine, FK-506 and rapamycin, the chemotherapeutic agents taxol and taxotere, the antibiotic clarithromycin and the HIV protease inhibitors A-77003, A-80987, MK-639, saquinavir, VX-478, AG1343, DMP-323, XM-450, BILA 2011 BS, BILA 1096 BS, BILA 2185 BS, BMS 186,318, LB71262, SC-52151, SC-629 (N,N-dimethylglycyl-N-(2-hyrdoxy-3-(((4-methoxyphenyl)sulphonyl)(2-methyl-propyl)amino)-1-(phenylmethyl)propyl)-3-methyl-L-valinamide), KNI-272, CGP 53437, CGP 57813 and U-103017.

In a preferred embodiment of the present invention, there is disclosed a method for improving the pharmacokinetics of an HIV protease inhibitor (or a pharmaceutically acceptable salt thereof) which is metabolized by cytochrome P450 monooxygenase comprising coadministering a compound of the instant invention or a pharmaceutically acceptable salt thereof. Such a combination of a compound of the instant invention or a pharmaceutically acceptable salt thereof and an HIV protease inhibitor or a pharmaceutically acceptable salt thereof which is metabolized by cytochrome P450 monooxygenase is useful for inhibiting HIV protease in humans and is also useful for inhibition, treatment or prophylaxis of an HIV infection or AIDS (acquired immune deficiency syndrome) in humans. When administered in combination, the two therapeutic agents can be formulated as separate compositions which are administered at the same time or different times, or the two therapeutic agents can be administered as a single composition.

Preparation of Sulfonyl Chlorides

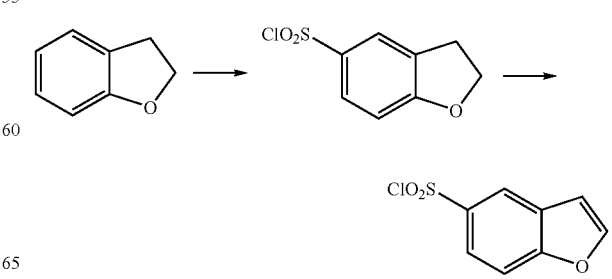

2,3-Dihydrobenzofuran-5-sulfonyl chloride

Prepared from commercially available 2,3-dihydrobenzofuran as described in the patent EP 0583960A2.

3.56 g (29.6 mmol) 2,3-dihydrobenzofuran was added to a slurry of 5.44 g (35.5 mmol) sulfur trioxide-N,N-dimethylformamide complex in 12 mL 1,2-dichloroethane under argon. The reaction was heated to 85° C. for 1 hour and then cooled to room temperature. Thionyl chloride (2.6 mL, 35.5 mmol, 1.2 eq) was added dropwise and the reaction was slowly heated over the course of one hour, by which time it had reached 75° C. The mixture was allowed to cool to room temperature and 100 mL of methylene chloride and 100 mL water were added. The organic extract was separated, dried over magnesium sulfate, filtered and evaporated to afford 6.56 g (100%) of 2,3-dihydrobenzofuran-5-sulfonyl chloride as a tan oil. (TLC Rf chloroform/hexanes=1/1)

Benzofuran-5-sulfonyl chloride 2,3-Dihydrobenzofuran-5-sulfonyl chloride 300 mg (1.37 mmol) was dissolved in 2 mL of benzene. N-bromosuccinimide 244 mg (1.37 mmol) and AIBN 3 mg were added to the solution and the reaction was heated at 80° C. for 1 hour. The reaction was allowed to come to room temperature, filtered and the benzene removed under vacuum. The residue was purified by chromatography on silica gel with hexanes/methylene chloride=2/1 to afford 237 mg (80%) of the pure material (TLC). The final product can be recrystallized from ether/hexanes to provide colorless crystals with m.p. 48.5-50.6° C.

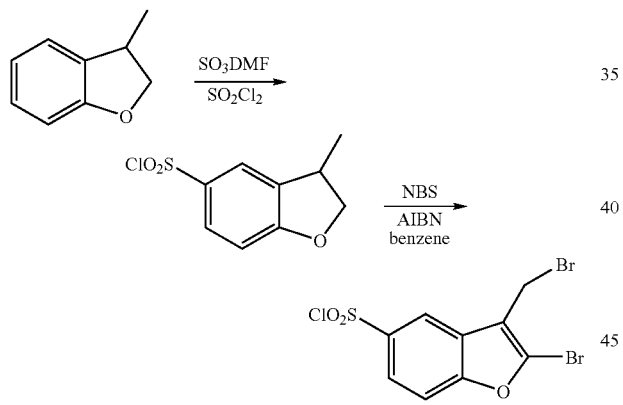

3-Methyl-2,3-dihydrobenzofuran was synthesized as described in the literature starting from 2-iodophenol (Organic Synthesis, CV3, 418; L. W. Menapace and H. G. Kuivila, J. Amer. Chem. Soc., 86, 3047 (1964), and references cited therein).

3-Methyl-2,3-dihydrobenzofuran-5-sulfonyl chloride

Prepared from 3-methyl-2,3-dihydrobenzofuran as Described in the Patent EP 0583960A2.

12.03 g (90.4 mmol) 3-methyl-2,3-dihydrobenzofuran was added to the slurry of 15.22 g (99.5 mmol) sulfur trioxide-N,N-dimethylformamide complex in 25 mL 1,2-dichloroethane under argon. The reaction was heated to 85° C. for 1 hour and cooled to room temperature. Thionyl chloride (7.9 mL, 108.5 mmol) was added dropwise and the reaction was slowly heated over the course of one hour, by which time it had reached 75° C. The mixture was allowed to cool to room temperature and 150 mL of methylene chloride and 150 mL water were added. The water layer was extracted with methylene chloride (2×30 mL). The organic extracts were combined, washed by 100 mL water, dried over magnesium sulfate, filtered and evaporated to afford 20.4 g (97%) of tan oil pure by TLC (chloroform/hexanes=1/1).

2-bromo-3-bromomethyl-benzofuran-5-sulfonyl chloride

3-Methyl-2,3-dihydrobenzofuran-5-sulfonyl chloride (5.0 g, 21.5 mmol) was dissolved in 1,2-dichloroethane (75 mL). To this was added N-bromosuccinimide (NBS) (11.5 g, 64.5 mmol) followed by azoisobutyronitrile (106 mg, 0.6 mmol). The reaction mixture was heated at 40° C. After 1.5 h another 3.8 g of NBS was added. After an additional 3 h at 40° C. the reaction mixture was 75 mL of cold water. The aqueous layer was extracted with dichloromethane (2×10 mL), the combined organic extract washed with 5% sodium thiosulfate, water and brine. Concentrating the organic layer followed by crystallization from ethyl acetate/hexane provided 6.0 g (73%) of product as a white crystalline solid, m.p. 128.6-129.8° C. TLC (chloroform/hexanes=1/1)

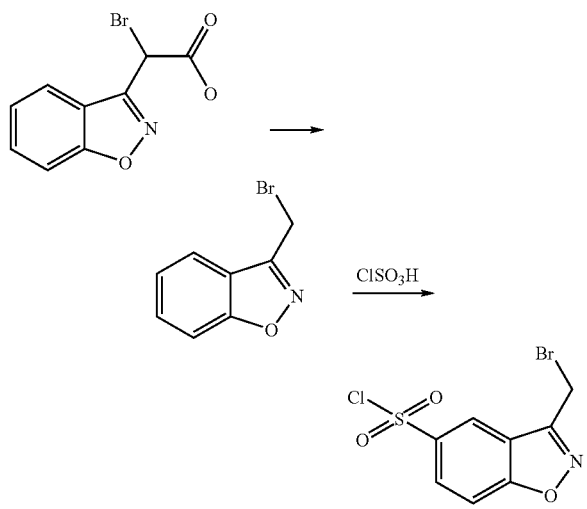

3-Bromomethyl-benzo[d]isoxazole (Mohareb et al., Z.Naturforsch.B 1067 (1990); Henke, et al., J. Med. Chem. 2706 (1997) Benzo[d]isoxazol-3-yl-bromo-acetic acid [(J. Med. Chem. 5428 (2003), Chem. Pharm. Bull, 3498 (1978)] was slowly heated under argon with stirring to 130° C. and held there for 30 minutes. Copious gas evolution was observed during this time. The reaction was cooled to room temperature and the resulting brown crystals were filtered off and purified via column chromatography (hexanes), (2.3 g, 70% yield).

3-Bromomethyl-benzo[d]isoxazole-5-sulfonyl chloride

Chlorosulfonic acid (1.5 ml, 22 mmol) was slowly added to 3-Bromomethyl-benzo[d]isoxazole (1.0 g, 4.7 mmol) at RT under argon. The reaction was heated at 90° C. for 12 h and then left at RT for 6 h. The resulting viscous oil was quenched over ice, extracted with EtOAc, dried over MgSO4 and concentrated in vacuo to a brown oil (1.17 g, 80% yield).

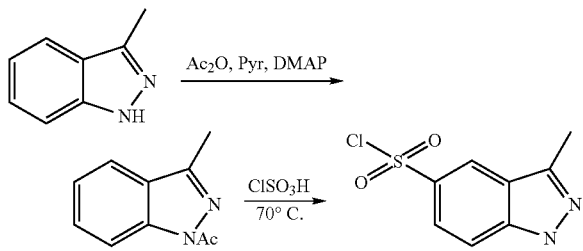

1-(3-methyl-indazol-1-yl)-ethanone [Chem. Ber. 53; 1204 (1920)]

3-Methylindazole (1.00 g, 7.6 mmol) (J. Med. Chem. 2706 (1997)] was dissolved in 10 ml THF and stirred at room temperature under a blanket of argon. Pyridine (0.64 ml, 7.9 mmol) was added, followed by Ac₂O (0.79 ml, 8.3 mmol) and catalytic DMAP (90 mg, 0.7 mmol). The reaction proceeded for 2 h and was then partitioned between 1N HCl and dichloromethane. The organic phase was dried over MgSO4 and concentrated under vacuum to a tan solid (1.2 g, 91% yield).

3-Methyl-1H-indazole-5-sulfonyl chloride

To chlorosulfonic acid (0.38 ml, 5.7 mmol) under a blanket of argon in an ice bath was added 1-(3-methyl-indazol-1-yl)-ethanone (200 mg, 1.1 mmol). The reaction was allowed to warm to room temperature and then was heated at 70° C. for 45 min. The reaction was cooled to room temperature, slowly quenched over ice and extracted with dichloromethane. The organic phase was dried over MgSO₄ and concentrated in vacuo to a tan solid (160 mg, 0.7 mmol, 61% yield). TLC: $R_f$ 0.2 (1:4 ethyl acetate: hexane). MS 229 MH⁺.

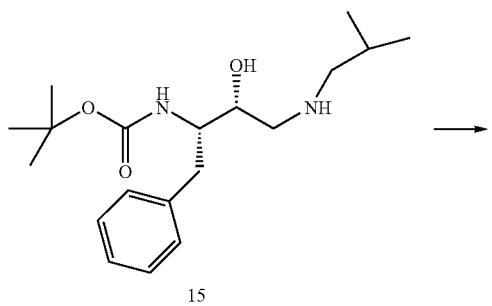

15

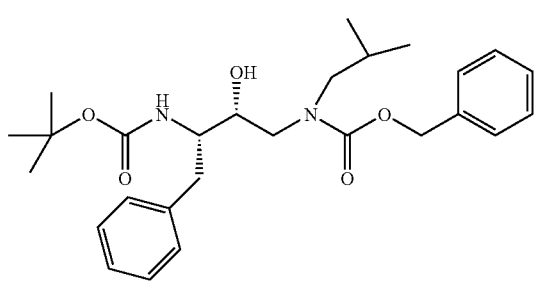

16

3-tert-Butoxycarbonylamino-2-hydroxy-4-phenyl-butyl)-isobutyl-carbamic acid benzyl ester 16

To (1-Benzyl-2-hydroxy-3-isobutylamino-propyl)-carbamic acid tert-butyl ester[2] 15 (94 g, 0.279 mol) in 600 ml THF was added a solution of Na₂CO₃ (32.5 g, 0.307 mol) in 200 ml H₂O. Cbz-chloride (52.4 g, 0.307 mol, 1.1 eq) dissolved in THF (100 mL) was added dropwise to the above mixture at 5-10° C. (ice bath) over the course of 1 h, after which time the mixture was stirred for additional 2 h at 10° C. Ethyl acetate (1000 ml) was then added to the reaction mixture, the organic layer was separated, washed sequentially by aqueous NaHCO₃, KHSO₄ and brine, dried over Na₂SO₄, filtered and concentrated in vacuo. The oily residue crystallized from EtOAc/hexane to give 3-tert-butoxycarbonylamino-2-hydroxy-4-phenyl-butyl)-isobutyl-carbamic acid benzyl ester 16 (101 g, 77%) as a white solid, m.p. 79-81° C.

2. Ghosh, et al. J. Org. Chem. 63; 18; 6146-6152 (1998).

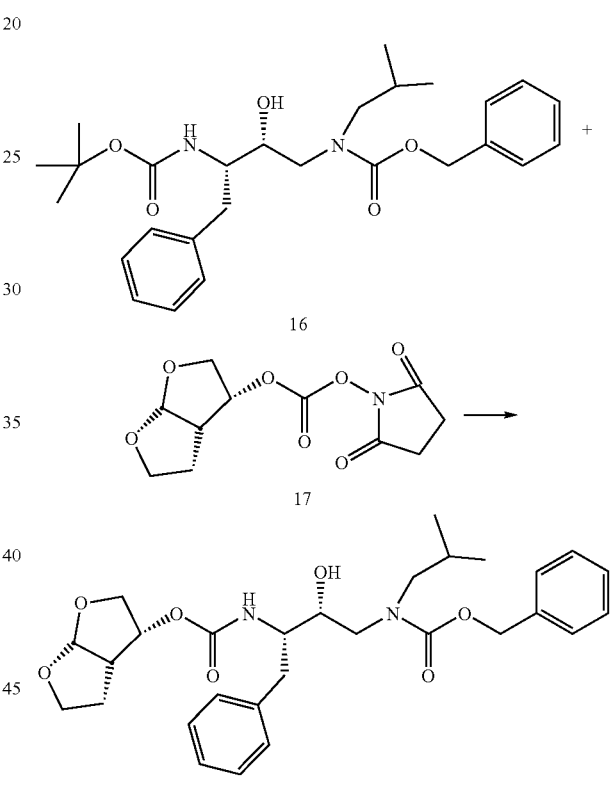

[3-(Hexahydro-furo[2,3-b]furan-3-yloxycarbonylamino)-2-hydroxy-4-phenyl-butyl]-isobutyl-carbamic acid benzyl ester 18

(3-tert-Butoxycarbonylamino-2-hydroxy-4-phenyl-butyl)-isobutyl-carbamic acid benzyl ester 16 (7.54 g, 15 mmol) and 35 ml of 4M HCl in dioxane were stirred 30 min under an argon atmosphere. The mixture was concentrated in vacuo, and co-evaporated twice with dichloromethane. The residue was dissolved in dichloromethane (50ml) and N,N-diisopropylethylamine (6.1 ml, 35 mmol), and carbonic acid 2,5-dioxo-pyrrolidin-1-yl ester hexahydro-furo[2,3-b]furan-3-yl ester 17 (4.88g, 18 mmol) was added. The reaction mixture was stirred overnight, and then concentrated in vacuo. The residue was diluted with dichloromethane, and sequentially washed with brine, 10% KHSO$_4$, brine, saturated NaHCO$_3$, and brine, then dried over MgSO$_4$, and concentrated in vacuo. The oily residue was purified by flash chromatography using 70:30 ethyl acetate hexane as eluant, to give [3-(Hexahydro-furo[2,3-b]furan-3-yloxycarbonylamino)-2-hydroxy-4-phenyl-butyl]-isobutyl-carbamic acid benzyl ester 18 (5.8 g, 73%) as a white solid. TLC: R$_f$ 0.56 (7:3 ethyl acetate: hexane). MS 527 (MH)$^+$.

Related procedure: Ghosh, et al. BMCL 687 (1998).

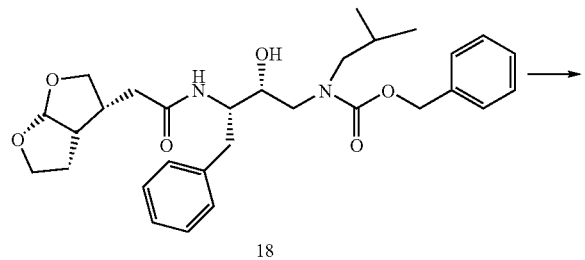

18

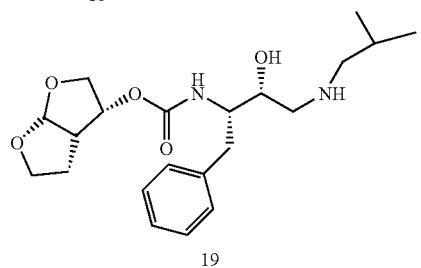

19

(1-Benzyl-2-hydroxy-3-isobutylamino-propyl)-carbamic acid hexahydro-furo[2,3-b]furan-3-yl ester 19

A mixture of [3-(hexahydro-furo[2,3-b]furan-3-yloxycarbonylamino)-2-hydroxy-4-phenyl-butyl]-isobutyl-carbamic acid benzyl ester 18 (5.5 g, 10.4 mmol) and 550 mg of 10% Pd/C in 130 ml of ethanol was stirred under a hydrogen atmosphere overnight. The catalyst was removed by filtration through Celite®, and the solution was evaporated to dryness to yield (1-benzyl-2-hydroxy-3-isobutylamino-propyl)-carbamic acid hexahydro-furo[2,3-b]furan-3-yl ester 19 (4.0 g, 97%) as a white solid. TLC: R$_f$ 0.36 (5:15:85 triethylamine: methanol:ethyl acetate). MS 393 (MH)$^+$.

Preparation of Target Compounds

Method 1

The sulfonyl chloride is reacted with(1-benzyl-2-hydroxy-3-isobutylamino-propyl)-carbamic acid hexahydro-furo[2,3-b]furan-3-yl ester 19 in methylene chloride and aqueous NAHCO3 and stirred at room temperature until reaction complete.

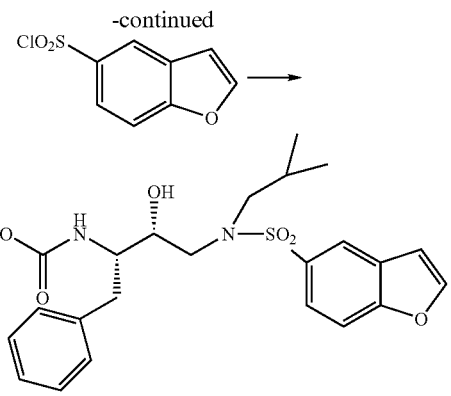

{3-[(Benzofuran-5-sulfonyl)-isobutyl-amino]-1-benzyl-2-hydroxy-propyl}-carbamic acid hexahydro-furo[2,3-b]furan-3-yl ester Benzofuran-5-sulfonyl chloride 148 mg (0.68 mmol) was dissolved in 5 mL of methylene chloride. (1-Benzyl-2-hydroxy-3-isobutylamino-propyl)-carbamic acid hexahydro-furo[2,3-b]furan-3-yl ester 19 (244 mg, 0.62 mmol) was added followed by 0.63 mL 10% NaHCO3 solution (0.75 mmol). The reaction was stirred at room temperature for 16 hours. The organic phase was separated and loaded onto silica gel in methylene chloride. The excess of benzofuran-5-sulfonyl chloride was washed out by several portions of methylene chloride. The final product was obtained by eluting with 3/1 ethyl acetate/methylene chloride. Concentration in vacuo afforded 350 mg (98.5% yield) of the final product with HPLC purity of >97% (220 nm). The product can be recrystallized from ethyl acetate/hexanes to get colorless crystals m.p. 122-124° C. MS 573 (MH)$^+$.

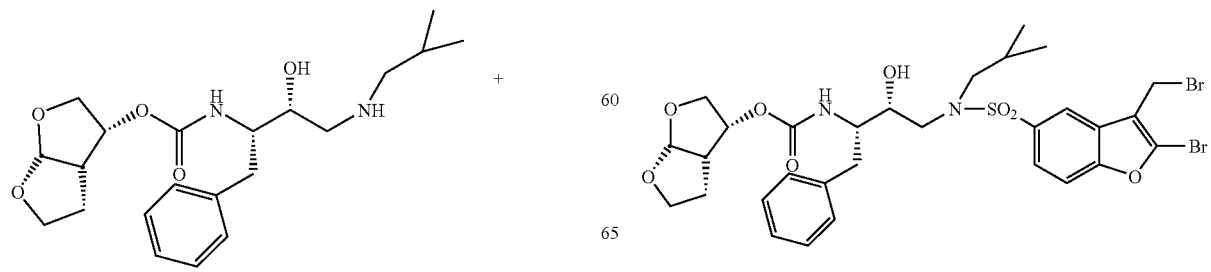

{1-Benzyl-3-[(2-bromo-3-bromomethyl-benzofuran-5-sulfonyl)-isobutyl-amino]-2-hydroxy-propyl}-carbamic acid hexahydro-furo [2,3-b]furan-3-yl ester 2-Bromo-3-bromomethyl-benzofuran-5-sulfonyl chloride (5) (1.75 g, 4.5 mmol) was dissolved in 50 mL of methylene chloride. (1-benzyl-2-hydroxy-3-isobutylamino-propyl)-carbamic acid hexahydro-furo[2,3-b]furan-3-yl ester 19 (1.75 g, 4.5 mmol) was added followed by 4.5 mL 10% NaHCO3 solution (5.4 mmol). The reaction was stirred at room temperature for 16 hours. The organic phase was partitioned between methylene chloride (150 mL) and water (100 mL), the organic phase separated, dried over magnesium sulfate, filtered and concentrated under vacuum. The final product was chromatographed on silica using 1/1 ethyl acetate/methylene chloride eluent to yield 2.79 g of the product (83%) as white crystals. (>95% HPLC). MS 663, 665 (M-H)

Method 2

The haloalkyl aromatic compound is reacted with excess amine or another nucleophile in the presence of excess base such as triethylamine.

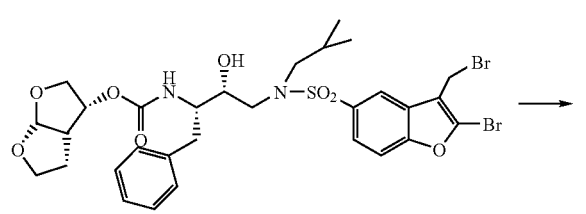

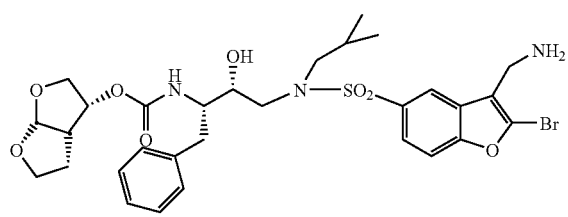

{3-[(3-Aminomethyl-2-bromo-benzofuran-5-sulfonyl)-isobutyl-amino]-1-benzyl-2-hydroxy-propyl}-carbamic acid hexahydro-furo[2,3-b]furan-3-yl ester Bis-THF-core-2-bromo-3-bromomethyl-benzofuran-5-sulfonyl (6) (2.02 g, 2.71 mmol) was dissolved in 100 mL methylene chloride and added dropwise to 100 mL of 7N ammonia in methanol at 4° C. was added. After addition was complete, the reaction was stirred at room temperature for 16 hours. HPLC analysis indicated no remaining starting material. The volatile components were removed under vacuum and the residue was used in the next step without further purification. A sample from a separate run was purified by prep HPLC. MS 680, 682 (MH+)

Method 3

The bromo substituent on the heteroaromatic ring is removed by hydrogenation over 10% Pd/C in the presence of triethylamine.

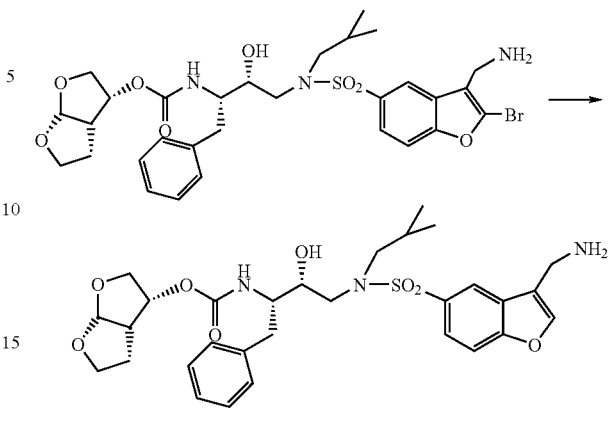

{3-[(3-Aminomethyl-benzofuran-5-sulfonyl)-isobutyl-amino]-1-benzyl-2-hydroxy-propyl}-carbamic acid hexahydro-furo [2,3-b]furan-3-yl ester Bis-THF-core-2-bromo-3-aminomethyl-benzofuran-5-sulfonyl (7) from the previous reaction was dissolved in 150 mL tetrahydrofuran. 10% Pd/C (100 mg) and triethylamine 0.76 mL were added. The reaction was stirred under hydrogen at room temperature. Once there was no starting 7 left in the reaction (HPLC), the reaction mixture was filtered and concentrated in vacuo. The final product can be used directly in the next step. A sample from a separate run was purified by prep HPLC. MS 602 (MH+).

Method 4

Aminoalkyl substituted compounds are acylated or sulfonylated using a suitable activated carboxylic or sulfonic acid derivative in the presence of a base such as triethylamine. They can be alkylated using an activated alcohol derivative or halide or by reductive amination with an aldehyde or ketone.

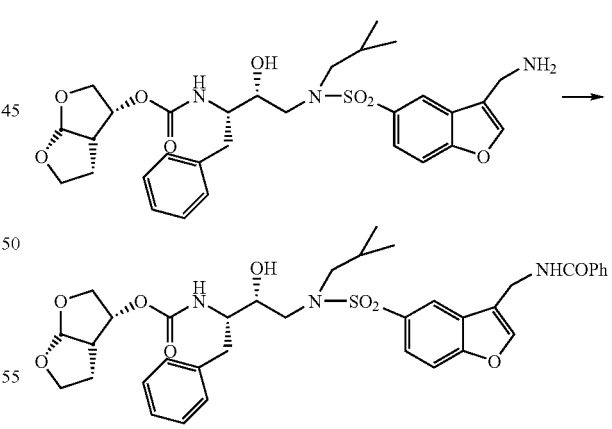

(3-{[3-(Benzoylamino-methyl)-benzofuran-5-sulfonyl]-isobutyl-amino}-1-benzyl-2-hydroxy-propyl)-carbamic acid hexahydro-furo [2,3-b]furan-3-yl ester {3-[(3-Aminomethyl-benzofuran-5-sulfonyl)-isobutyl-amino]-1-benzyl-2-hydroxy-propyl}-carbamic acid hexahydro-furo[2,3-b]furan-3-yl ester from the previous step (20 mg, 33 umol) was dissolved in 0.5 mL THF. 5.8 uL (50 umol)

benzoyl chloride and 7 uL (50 umol) triethylamine were added and the reaction was stirred at room temperature for 1 h. The reaction mixture was purified by prep TLC on the silica gel plate with ethyl acetate/hexanes=2/1 to afford 12 mg (17 umol, 52%) of product. MS 706 (MH+).

Method 5

The heterocyclic ring is built up from a condensation reaction of a suitably substituted aromatic ring with a bidentate nucleophile such as hydrazine or hydroxylamine.

Step 1

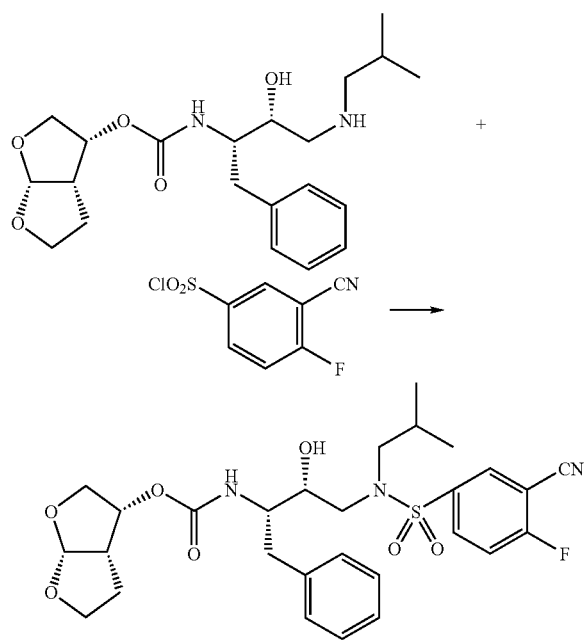

{1-Benzyl-3-[(3-cyano-4-fluoro-benzenesulfonyl)-isobutyl-amino]-2-hydroxy-propyl}-carbamic acid hexahydro-furo[2,3-b]furan-3-yl ester To a solution of (1-benzyl-2-hydroxy-3-isobutylamino-propyl)-carbamic acid hexahydro-furo[2,3-b]furan-3-yl ester 19 in CH2Cl2 (4 mL) was added 4-fluoro-3-cyanobenzenesulfonyl chloride (92 mg, 0.42 mmol) followed by NaHCO3 (40 mg) and satd. NaHCO3 (0.4 mL) and stirred at RT for 1 h. The reaction mixture was diluted with ethyl acetate (25 mL) and washed with water, brine and dried with Na2SO4 and concentrated to furnish crude product (240 mg). The crude product was purified by column chromatography using 1/1 ethyl acetate/hexane to provide 200 mg product (92% yield).

Step 2

{3-[(3-Amino-1H-indazole-5-sulfonyl)-isobutyl-amino]-1-benzyl-2-hydroxy-propyl}-carbamic acid hexahydro-furo[2,3-b]furan-3-yl ester {1-Benzyl-3-[(3-cyano-4-fluoro-benzenesulfonyl)-isobutyl-amino]-2-hydroxy-propyl}-carbamic acid hexahydro-furo[2,3-b]furan-3-yl ester (200 mg, 0.35 mmol) was dissolved in EtOH (6.0 mL) and CH2Cl2 (4.0 mL) Hydrazine was added (0.066 mL, 2.1 mmol) and the reaction heated at 50° C. for 12 h. The reaction mixture was concentrated and purified by prep TLC using MeOH/CHCl3 (1/9) to furnish the product (140 mg, 70% yield). R$_f$ 0.5 MeOH/CHCl3 (1/9). MS 588 (MH$^+$).

Method 6

The sulfonyl chloride was first reacted with (1-Benzyl-2-hydroxy-3-isobutylamino-propyl)-carbamic acid tert-butyl ester using the conditions of Method 1. The Boc group was then removed under acidic conditions and the resulting amine reacted with 2,5-dioxo-pyrrolidin-1-yl ester hexahydro-furo[2,3-b]furan-3-yl ester in the presence of a base such as diisopropylethylamine.

Step 1

{1-Benzyl-2-hydroxy-3-[isobutyl-(3-methyl-1H-indazole-5-sulfonyl)-amino]-propyl}-carbamic acid tert-butyl ester To (1-Benzyl-2-hydroxy-3-isobutylamino-propyl)-carbamic acid tert-butyl ester 15 (60 mg, 0.18 mmol) and 3-methyl-1H-indazole-5-sulfonyl chloride (50 mg, 0.22 mmol) in 2 mL dichloromethane was added a 70 ul solution of a saturated NaHCO3 and 30 mg NaHCO3 and stirred overnight. The product was purified by preparative TLC using 1:1 ethyl acetate: hexane to give 95 mg product (99% yield). MS 531 (MH+).

Step 2

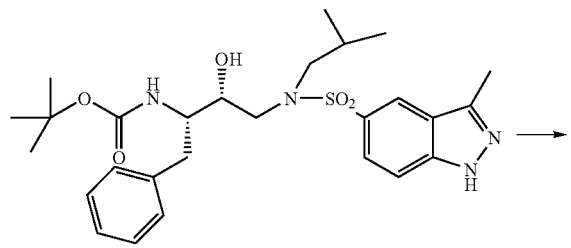

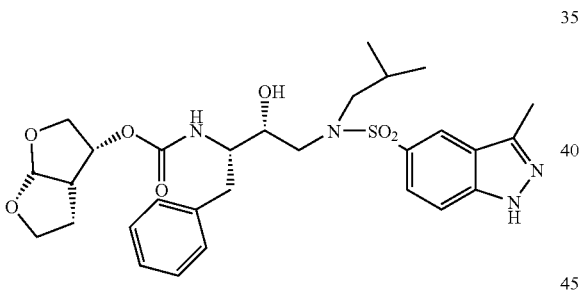

{1-Benzyl-2-hydroxy-3-[isobutyl-(3-methyl-1H-indazole-5-sulfonyl)-amino]-propyl}-carbamic acid hexahydro-furo[2,3-b]furan-3-yl ester {1-Benzyl-2-hydroxy-3-[isobutyl-(3-methyl-1H-indazole-5-sulfonyl)-amino]-propyl}-carbamic acid tert-butyl ester (25 mg, 0.047 mmol) was added to a solution of 4N HCl in dioxane (0.25 mL). Material precipitated out so 800 uL conc. HCl was added and the reaction heated at reflux for 2 h. The resulting solution was concentrated under vacuum and concentrated 2 additional times from 1 mL methylene chloride. This crude amine was dissolved in 0.5 mL methylene chloride and diisopropylethylamine (80 uL, 0.46 mmol) was then added. To this solution was added carbonic acid 2,5-dioxo-pyrrolidin-1-yl ester hexahydro-furo[2,3-b]furan-3-yl ester (16 mg, 0.055 mmol) and the reaction stirred overnight. The reaction was concentrated under vacuum and purified by preparative HPLC. MS 587 (MH+).

Method 7

Side chains with oxidizable groups such as sulfides were oxidized with a suitable reagent such as hydrogen peroxide. Side chains with reducible groups such as esters could be reduced with a reducing agent such as LAH.

(1-Benzyl-3-{[3-(butane-1-sulfinylmethyl)-benzofuran-5-sulfonyl]-isobutyl-amino}-2-hydroxy-propyl)-carbamic acid hexahydro-furo[2,3-b]furan-3-yl ester

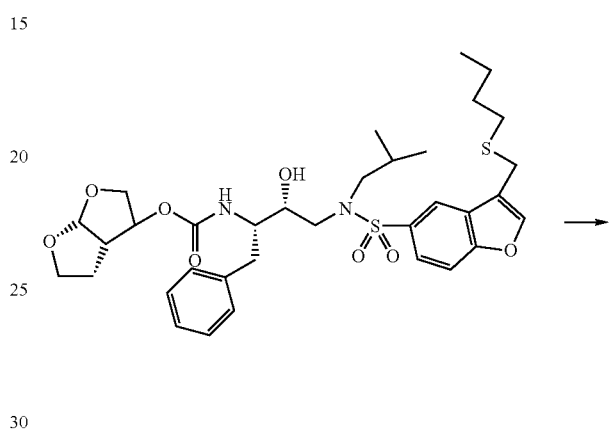

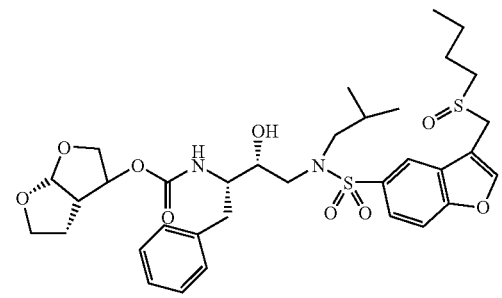

{1-Benzyl-3-[(3-butylsulfanylmethyl-benzofuran-5-sulfonyl)-isobutyl-amino]-2-hydroxy-propyl}-carbamic acid hexahydro-furo[2,3-b]furan-3-yl ester (10 mg, 14.8 umol) was dissolved in 0.5 mL THF and 150 uL of 50% hydrogen peroxide in water was added. The reaction was stirred at room temperature and the progress was monitored by HPLC analysis. After 3.5 hours there was no starting material left in the reaction mixture. The reaction was partitioned between 20 mL ethyl acetate and 20 mL 0.1 N sodium thiosulfate solution. The organic phase was separated, washed with 15 mL brine and dried over anhydrous sodium sulfate. Filtration followed by concentration under vacuum afforded 10 mg (97%) of the final HPLC pure product. MS 691 (MH+).

HPLC Conditions:
  Waters column YMC ODS-AQ S-3 120A 3.0×100 mm
  Mobile phase A—water, 0.1% TFA
  Mobile phase B—methanol, 0.1% TFA
  Flow 0.75 mL/min Gradient:
  0-3 min—20% B
  3-16 min—20-85% B
  16-20 min—85% B
  Detection by UV at 222 m

TABLE 1

Benzofuran Synthesis

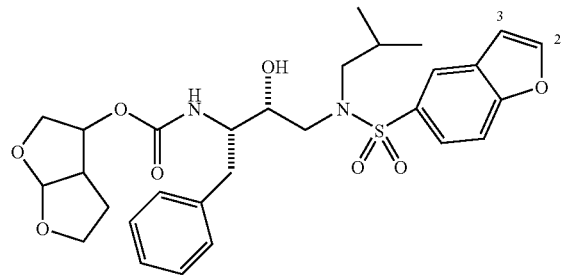

| Compound | 2- | 3- | Method | Reagents | Solvent | Temp ° C. | Time | Yield | MH+ | HPLC RT |
|---|---|---|---|---|---|---|---|---|---|---|
| 101 | H | H | 1 | Benzofuran-5-sulfonyl chloride | DCM | RT | 16 h | 99% | 573 | 13.9 min. |
| 102 | Me | H | 1 | 2-Methyl-benzofuran-5-sulfonyl chloride | DCM | RT | 16 h | 83% | 587 | 15.1 min. |
| 103 | H | Me | 1 | 3-Methyl-benzofuran-5-sulfonyl chloride | DCM | RT | 16 h | 87% | 587 | 14.9 min. |
| 104 | CH2Br | H | 1 | 2-bromomethyl-benzofuran-5-sulfonyl chloride | DCM | RT | 16 h | 79% | 663, 665 (M − H) | 14.8 min. |
| 105 | CH2NH2 | H | 2 | Ammonia in MeOH | MeOH | RT | 18 h | 99% | 602 | 10.6 min. |
| 106 | CH2NHCH(Me)CO2Et | H | 4 | Acetic anhydride | THF | RT | 16 h | 100% | 644 | 12.8 min. |
| 107 | H | CH2NHCOMe | 4 | Acetic anhydride | THF | RT | 2 h | 56% | 644 | 12.8 min. |
| 108 | H | CH2-4-morpholino | 3 | H2, Pd/C | THF | RT | 2 h | 67% | 672 | 12.8 min. |
| 109 | H | CH2-1-piperidino | 3 | H2, Pd/C | THF | RT | 1.5 h | 98% | 670 | 11.8 min. |
| 110 | H | CH2NHCH2CO2tBu | 3 | H2, Pd/C | THF | RT | 2 h | 68% | 716 | |
| 111 | H | CH2S(O)Bu | 7 | H2O2 | THF | RT | 3.5 h | 97% | 691 | 14.0 min. |
| 112 | H | CH2NHCO2Et | 4 | Ethyl chloroformate, Et3N | THF | RT | 16 h | 75% | 674 | 13.6 min. |
| 113 | H | CH2NHCOEt | 4 | Propionic acid, DCC, Et3N | THF | RT | 1 h | 73% | 658 | 13.0 min. |
| 114 | H | CH2NHCOPh | 4 | Benzoyl chloride, Et3N | THF | RT | 1 h | 51% | 706 | 13.5 min. |
| 115 | H | CH2NHSO2iPr | 4 | Isopropylsulfonyl chloride, NaHCO3 | DCM | RT | 24 h | 77% | 708 | 13.5 min. |
| 116 | H | CH2NHCOCH2NHCbz | 4 | Cbz-Gly-OH, TBTU, Et3N | THF + DMF | RT | 16 h | 49% | 793 | 14.6 min. |
| 117 | H | CH2NH(CH2)2-2-pyridinyl | 3 | H2, Pd/C | THF | RT | 3 h | 51% | 707 | 10.8 min. |
| 118 | H | CH2NHCO-3-pyridyl | 4 | Nicotinoyl chloride, Et3N | THF | RT | 16 h | 34% | 707 | 12.5 min. |
| 119 | H | CH2NHCOCH2SCH2Ph | 4 | HOCOCH2SCH2Ph, TBTU, Et3N | THF | RT | 16 h | 53% | 766 | 14.8 min. |
| 120 | H | CH2NHCOCH2S(O)CH2Ph | 7 | H2O2 | THF | RT | 24 h | 96% | 782 | 13.7 min. |
| 121 | CH2NHCO2Et | H | 4 | Ethyl chloroformate, Et3N | THF | RT | 18 h | 71% | 674 | 13.2 min. |

TABLE 1-continued

Benzofuran Synthesis

| Compound | 2- | 3- | Method | Reagents | Solvent | Temp °C. | Time | Yield | MH+ | HPLC RT |
|---|---|---|---|---|---|---|---|---|---|---|
| 122 | H | CH2OCOCH3 | 3 | H2, Pd/C | THF | RT | 4 h | 67% | 645 | 16.0 min. |
| 123 | H | CH2OCH3 | 3 | H2, Pd/C | THF | RT | 2.5 h | 75% | 617 | 15.7 min. |
| 124 | H | CH2OH | 3 | H2, Pd/C | THF | RT | 2.5 h | 62% | 603 | 14.6 min. |
| 125 | H | CH2NHCO-2-furanyl | 4 | 2-Furoic acid, TBTU, Et3N | THF + DMF | RT | 18 h | 50% | 696 | 15.3 min. |
| 126 | H | CH2N(CO2Et)CH2CH2OMe | 4 | Ethyl chloroformate, Et3N | THF | RT | 16 h | 84% | 732 | 11.8 min. |
| 127 | Br | CH2Br | 1 | 2-bromo-3-bromomethyl-benzofuran-5-sulfonyl chloride | DCM | RT | 16 h | 77% | 743, 745, 747 | 15.4 min. |
| 128 | Br | CH2NH2 | 2 | Ammonia in MeOH | DCM | RT | 16 h | 92% | 680, 682 | 11.6 min. |
| 129 | Br | CH2-4-morpholino | 2 | Morpholine | EtOH | RT | 16 h | 100% | 750, 752 | 11.6 min. |
| 130 | Br | CH2SBu | 2 | BuSH, Et3N | DCM | RT | 16 h | 100% | 753, 755 | 17.0 min. |
| 131 | Br | CH2NHEt | 2 | EtNH2 | DCM | RT | 16 h | 71% | 708, 710 | 11.8 min. |
| 132 | Br | CH2-1-piperidino | 2 | Piperidine | DCM | RT | 16 h | 72% | 748, 750 | 12.1 min. |
| 133 | Br | CH2NHCH2CO2tBu | 2 | Gly-OtBu, diisopropylethylamine | DCM | RT | 144 h | 83% | 794, 796 | 13.1 min. |
| 134 | Br | CH2NH(CH2)2-2-pyridinyl | 2 | 2-(2-aminoethyl)pyridine | DCM | RT | 16 h | 62% | | |
| 135 | Br | CH2NH(CH2)2SEt | 2 | 2-(ethylthio)ethylamine, Et3N | DCM | RT | 16 h | 84% | | 13.6 min. |
| 136 | Br | CH2NH(CH2)2OMe | 2 | 2-methoxyethylamine, Et3N | DCM | RT | 16 h | 74% | | 15.8 min. |
| 137 | Br | CH2OCOCH3 | 2 | NaOAc, NaI | Acetone | 60 | 16 h | 86% | | 17.1 min. |
| 138 | Br | CH2OCH3 | 2 | Et3N | MeOH | 65 | 10 h | 95% | 695, 697 | 17.0 min. |
| 139 | Br | CH2OH | 2 | KHCO3 | MeOH | 90 | 4 h | 30% | 683, 685 | 16.0 min. |
| 140 | CH2NEt2 | H | 2 | Et2NH | DCM | RT | 16 h | 85% | 658 | 11.5 min. |
| 141 | CH2NHEt | H | 2 | EtNH2 | DCM + MeOH | RT | 4 h | 84% | 630 | 11.0 min. |
| 142 | CH2-1-piperidino | H | 2 | Piperidine | DCM | RT | 4 h | 93% | 670 | 11.6 min. |
| 143 | CH2-4-morpholino | H | 2 | Morpholine | DCM | RT | 4 h | 98% | 672 | 11.0 min. |
| 144 | CH2NMeEt | H | 2 | Methylethylamine | DCM | RT | 3.5 h | 87% | 644 | 11.3 min. |
| 145 | CH2NHCH2Ph | H | 2 | Benzylamine | DCM | RT | 16 h | 77% | 692 | 11.9 min. |
| 146 | CH2SBu | H | 2 | BuSH, Et3N | DCM | RT | 16 h | 49% | 675 | 16.3 min. |
| 147 | H | CH2NH2 | 3 | H2, Pd/C | THF | RT | 2 h | 85% | 602 | 10.9 min. |
| 148 | H | CH2SBu | 3 | H2, Pd/C | THF | RT | 2 h | 91% | 675 | 16.1 min. |

TABLE 1-continued

Benzofuran Synthesis

| Compound | 2- | 3- | Method | Reagents | Solvent | Temp °C. | Time | Yield | MH+ | HPLC RT |
|---|---|---|---|---|---|---|---|---|---|---|
| 149 | H | CH2NHEt | 3 | H2, Pd/C | THF | RT | 1 h | 44% | 630 | 10.8 min. |
| 150 | H | CH2NH(CH2)2SEt | 3 | H2, Pd/C | THF | RT | 11 h | 60% | 690 | 13.7 min. |
| 151 | H | CH2NH(CH2)2OMe | 3 | H2, Pd/C | THF | RT | 1 h | 92% | 660 | 13.2 min. |
| 152 | H | CH2NHCOCH2-3-pyridyl | 4 | 3-Pyridylacetic acid, TBTU, Et3N | THF | RT | 16 h | 56% | 721 | 11.7 min. |
| 153 | H | CH2NEtCO2Et | 4 | Ethyl chloroformate, Et3N | THF | RT | 5 h | 62% | 702 | 16.8 min. |
| 154 | H | CH4NHCONHCH2CH3 | 4 | CCl2O, Et3N EtNH2 | DCM | 4 then RT | 16 h | 45% | 673 | 14.8 min. |
| 155 | CH2S(O)Bu | H | 7 | H2O2 | THF | RT | 24 h | 62% | 691 | 13.7 min. |

TABLE 2

Benzisoxazole Synthesis

| Compound | 3- | Method | Reagents | Solvent | Temp °C | Time | Yield | MH+ |
|---|---|---|---|---|---|---|---|---|
| 201 | Me | 1 | 3-Methylbenzisoxazole-5-sulfonyl chloride, NaHCO3 | CH2Cl2 | RT | 4 hr | 65 | 588 |
| 202 | CH2NHiPr | 2 | Isopropylamine | Neat | RT | 30 min | 80 | 645 |
| 203 | CH2NH2 | 2 | NH3/1,4-dioxane | THF | 50 | 2 hr | 70 | 603 |
| 204 | CH2NHSO2iPr | 4 | 2-propanesulfonyl chloride, NaHCO3 | CH2Cl2 | RT | 12 hr | 90 | 709 |
| 205 | CH2OAc | 2 | NaOAc, NaI | Acetone | 60 | 48 hr | 25 | 646 |
| 206 | CH2CH(Me)CO2Et | 4 | Ethyl pyruvate, NaBH3CN | AcOH/EtOH | RT | 1 hr | 52 | 703 |
| 207 | CH2NHSO2Me | 4 | Methanesulfonyl chloride, NaHCO3 | CH2Cl2 | RT | 12 hr | 100 | 681 |
| 208 | CH2S(O)Bu | 7 | H2O2 | THF | RT | 48 hr | 86 | 714 (Na) |
| 209 | CH2S-iPr | 2 | 2-Propanethiol | DMF | RT | 12 hr | 80 | 662 |
| 210 | CH2NMeSO2Me | 4 | Methanesulfonyl chloride, NaHCO3 | CH2Cl2 | RT | 12 hr | 68 | 695 |
| 211 | CH2NMeTs | 4 | p-Toluenesulfonyl chloride, NaHCO3 | CH2Cl2 | RT | 12 hr | 76 | 771 |
| 212 | CH2NHCO2iPr | 4 | isopropyl succinimido carbonate, NaHCO3 | CH2Cl2 | RT | 12 hr | 81 | 689 |

TABLE 2-continued

Benzisoxazole Synthesis

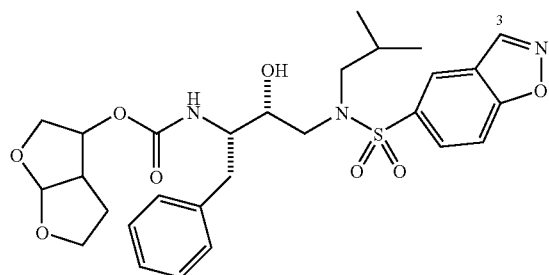

| Compound | 3- | Method | Reagents | Solvent | Temp ° C. | Time | Yield | MH+ |
|---|---|---|---|---|---|---|---|---|
| 213 | CH2OH | 2 | Sodium acetate, NaI | Acetone | 55 | 12 hr | 18 | 604 |
| 214 | CH2NHCOMe | 4 | Acetic anhydride, NaHCO3 | CH2Cl2 | RT | 12 hr | 90 | 646 |
| 215 | CH2OCOiPr | 2 | Isobutyric acid, NaI, NaOH | Acetone | reflux | 10 hr | 30 | 675 |
| 216 | CH2-1-imidazole | 2 | Imidazole | THF | RT | 12 hr | 98 | 654 |
| 217 | CH2NHCO2Et | 4 | Ethyl chloroformate, NaHCO3 | CH2Cl2 | RT | 12 hr | 93 | 676 |
| 218 | CH2OCOtBu | 2 | Trimethylacetic acid, NaI, NaOH | Acetone | reflux | 12 hr | 100 | 688 |
| 219 | CH2NHCH2CH2OMe | 2 | Methoxyethylamine | THF | RT | 5 hr | 88 | 661 |
| 220 | CH2NHCOiPr | 4 | Isobutyric acid, TBTU, Et3N | THF | RT | 4 hr | 80 | 673 |
| 221 | CH2NHCOPh | 4 | Benzoyl chloride, Et3N | THF | RT | 48 hr | 70 | 707 |
| 222 | CH2NHCO2Pr | 4 | Propyl chloroformate, NaHCO3 | CH2Cl2 | RT | 2 hr | 80 | 690 |
| 223 | CH2NHSO2Et | 4 | Ethanesulfonyl chloride, NaHCO3 | CH2Cl2 | RT | 12 hr | 80 | 695 |
| 224 | CH2NH(CH2)2-2-pyridinyl | 2 | 2-(2-Aminoethyl)pyridine | THF | RT | 12 hr | 70 | 708 |
| 225 | CH2N((CH2)2OMe)CO2Et | 4 | Ethyl Chloroformate, NaHCO3 | CH2Cl2 | RT | 12 hr | 80 | 733 |
| 226 | CH2NHCH2CH2SEt | 2 | 2-(Ethylthio)ethylamine | THF | 55 | 12 hr | 40 | 691 |
| 227 | CH2N((CH2)2OMe)SO2Et | 4 | Ethanesulfonyl chloride, NaHCO3 | CH2Cl2 | RT | 48 hr | 70 | 754 |
| 228 | CH2NHCH2CF2CF3 | 2 | 2,2,3,3,3-Pentafluoropropyl amine | THF | 55 | 12 hr | 60 | 735 |
| 229 | CH2NHCH2CF3 | 2 | 2,2,2-Trifluoroethylamine | THF | 55 | 12 hr | 70 | 685 |
| 230 | CH2NHCH2CH2OPh | 2 | 2-Phenoxyethylamine, Et3N | THF | RT | 12 hr | 80 | 724 |
| 231 | CH2NHBu | 2 | n-Butylamine | THF | RT | 12 hr | 80 | 658 (M − 1) |
| 232 | CH2NHCH2Ph | 2 | Benzyl amine | THF | RT | 12 hr | 80 | 693 |
| 233 | CH2SCH2CF3 | 2 | 2,2,2-Trifluoroethanethiol, NaHCO3 | DMF | RT | 12 hr | 60 | 702 |
| 234 | CH2NHCOCF3 | 4 | Trifluoroacetic anhydride, Et3N | CH2Cl2 | RT | 48 hr | 70 | 699 |
| 235 | CH2NHcyclopentyl | 2 | Cyclopentylamine | THF | RT | 12 hr | 80 | 716 formate |
| 236 | CH2NHCH2CH2NHBoc | 2 | N-Boc-ethylenediamine | THF | RT | 12 hr | 73 | 746 |
| 237 | CH2NH(CH2)3-1-pyrollidinone | 2 | 1-(3-aminopropyl)-2-pyrolidinone | THF | RT | 24 hr | 47 | 728 |
| 238 | CH2NHCH2cyclohexyl | 2 | Cyclohexane methylamine | THF | RT | 5 hr | 80 | 698 (M − 1) |
| 239 | CH2-4-morpholino | 2 | Morpholine | THF | RT | 1 hr | 61 | 673 |
| 240 | CH2NHCO-2-furanyl | 4 | 2-Furoyl chloride, Et3N, DMAP | CH2Cl2 | RT | 2 hr | 87 | 697 |
| 241 | CH2NHCH2-2-pyridinyl | 2 | 2-(aminomethyl)pyridine | THF | RT | 12 hr | 45 | 694 |
| 242 | CH2NHCH2-4-(2-methylthiazole) | 2 | 4-aminomethyl-2-methylthiazole, Et3N | THF | RT | 12 hr | 47 | 714 |
| 243 | CH2SO2Me | 2 | Sodium methanesulfinate | EtOH | 60 | 2 hr | 43 | 666 |
| 244 | CH2OCH3 | 2 | Succinimide sodium salt | MeOH | RT | 12 hr | 48 | 618 |

TABLE 2-continued

Benzisoxazole Synthesis

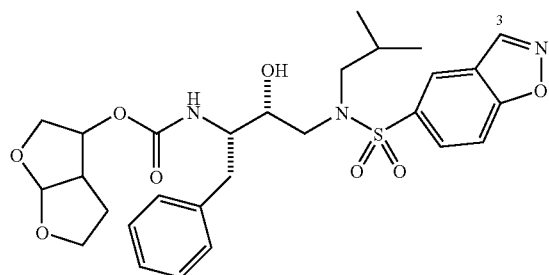

| Compound | 3- | Method | Reagents | Solvent | Temp °C. | Time | Yield | MH+ |
|---|---|---|---|---|---|---|---|---|
| 245 | CH2NHCOCF2CF3 | 4 | CF3CF2CO2H/(COCl)2, Et3N, DMAP | CH2Cl2 | RT | 4 hr | 42 | 749 |
| 246 | CH2OCH2CF3 | 2 | CF3CH2OH, KHCO3 | DMF | 60 | 1 hr | 50 | 686 |
| 247 | CH2N(Ac)CH2CF3 | 4 | CH3COCl, Et3N, DMAP | CH2Cl2 | RT | 2 hr | 50 | 727 |
| 248 | CH2NHCH2-5-benzofuranyl | 2 | 1-Benzofuran-5-ylmethylamine | THF | RT | 12 hr | 80 | 733 |
| 249 | OH | 1 | 3-chlorobenzisoxazole-5-sulfonyl chloride, NaHCO3 | CH2Cl2 | RT | 12 hr | 25 | 590 |
| 250 | CH2Br | 1 | 3-Bromomethylbenz-isoxazole-5-sulfonyl chloride, NaHCO3 | CH2Cl2 | RT | 2 hr | 24 | 666, 668 |
| 251 | CH2CO2Me | 1 | 3-Methoxycarbonyl methylbenzisoxazole-5-sulfonyl chloride, NaHCO3 | CH2Cl2 | RT | 1.5 hr | 20 | 646 |
| 252 | CH2NHMe | 2 | MeNH2 | EtOH | RT | 30 min | 98 | 617 |
| 253 | CH2NMe2 | 2 | Me2NH•HCl | Diisopropyl ethylamine | RT | 48 hr | 80 | 631 |
| 254 | CH2CN | 2 | NaCN | THF | 50 | 12 hr | 40 | 613 |
| 255 | CH2SCH2Ph | 2 | Benzyl mercaptan, K2CO3 | DMF | RT | 12 hr | 50 | 710 |
| 256 | CH2SPh | 2 | Benzenethiol | Acetone | RT | 12 hr | 70 | 696 |
| 257 | CH2N(CH2-2-pyridinyl)2 | 2 | 2-(aminomethyl)pyridine | THF | RT | 24 hr | 40 | 786 |
| 258 | CH2SCN | 2 | KSCN | ETOH/THF | 50 | 12 hr | 100 | 645 |
| 259 | CH2N(Et)CH2CH2CN | 2 | 3-(Ethylamino)pro-pionitrile, Et3N | THF | 40 | 12 hr | 70 | 684 |
| 260 | CH2SC(NH)NH2 | 2 | Thiourea | DMF | RT | 12 hr | 70 | 662 |
| 261 | CH2-1-pyrrolidine | 2 | Pyrrolidine | THF | RT | 1 hr | 56 | 657 |
| 262 | CH2-4-tosyl | 2 | p-Toluenesulfinic acid sodium salt | EtOH | 60 | 2 hr | 72 | 742 |
| 263 | CH2-1-succinimido | 2 | Succinimide, NaH | THF | RT | 10 hr | 60 | 685 |
| 264 | CH2I | 2 | NaI | DMF | 70 | 6 hr | 45 | 736 (Na) |
| 265 | NHAc | 4 | Acetic anhydride | CH2Cl2 | RT | 12 hr | 53 | 631 |
| 266 | NHCO2Et | 4 | Ethylchloroformate, NaOH, Benzyltriethyl ammonium chloride | Cl(CH2)2Cl | RT | 45 min | 36 | 661 |
| 267 | NHCHO | 4 | Formic acetic anhydride, DMAP | CH2Cl2 | RT | 5 hr | 35 | 617 |
| 268 | CH2NH(CH2CO2Et)2 | 4 | Ethyl bromoacetate, NaI | Acetone | 55 | 12 hr | 70 | 776 |
| 269 | CH2NH(CH2CO2iPr)2 | 4 | Isopropyl bromoacetate, NaI | Acetone | 55 | 12 hr | 67 | 804 |
| 270 | CH2NHCH2CO2Et | 4 | Ethyl glyoxalate, NaBH3CN | AcOH | RT | 1.5 hr | 30 | 689 |
| 271 | CH2NHCO(CH2)5CH3 | 4 | Heptanoyl chloride | THF | RT | 12 hr | 50 | 716 |
| 272 | CH2NHTosyl | 4 | p-Toluenesulfonyl chloride, NaHCO3 | CH2Cl2 | RT | 12 hr | 100 | 757 |
| 273 | CH2NMeSO2iPr | 4 | 2-propanesulfonyl chloride, NaHCO3 | CH2Cl2 | RT | 48 hr | 47 | 723 |
| 274 | CH2NHCHO | 4 | Formic acetic anhydride, NaHCO3 | CH2Cl2 | RT | 12 hr | 80 | 632 |
| 275 | CH2N(CH2Ph)2 | 4 | Benzaldehyde, NaBH3CN, AcOH | MeOH | RT | 45 min | 80 | 784 |
| 276 | CH2NHBoc | 4 | Di-tert-butyl dicarbonate, Et3N | CH2Cl2 | RT | 1.5 hr | 40 | 702 (M − 1) |
| 277 | CH2NHCO-4-morpholino | 4 | 4-Morpholinecarbonyl chloride, Et3N, DMAP | CH2Cl2 | RT | 3 hr | 42 | 716 |

TABLE 2-continued

Benzisoxazole Synthesis

| Compound | 3- | Method | Reagents | Solvent | Temp ° C. | Time | Yield | MH+ |
|---|---|---|---|---|---|---|---|---|
| 278 | CH2N(COPh)(CH2)3CH3 | 4 | PhCOCl, Et3N, DMAP | CH2Cl2 | RT | 2 hr | 72 | 763 |
| 279 | CH2N(CO2Et)CH2CF3 | 4 | Ethyl chloroformate, Et3N, DMAP | CH2Cl2 | RT | 2 hr | 45 | 757 |
| 280 | CH2N(CO-2-furyl)(CH2)3CH3 | 4 | 2-Furoyl chloride, Et3N, DMAP | CH2Cl2 | RT | 4 hr | 50 | 753 |
| 281 | CH2NHPh | 2 and 6 | Aniline | — | RT | 72 hr | 40 | 679 |
| 282 | CH2SBu | 2 and 6 | BuSH, K2CO3, DMF | CH2Cl2 | RT | 2 hr | 20 | 676 |

TABLE 3

Indazole Synthesis

| Compound | 3- | Method | Reagents | Solvent | Temp ° C. | Time | Yield | MH+ |
|---|---|---|---|---|---|---|---|---|
| 301 | Me | 1 and 6 | 3-methylindazole-5-sulfonyl chloride, NaHCO3 | CH2Cl2 | RT | 12 hr | 50 | 587 |
| 302 | NH(2-Bu) | 4 | 2-Butanone, NaBH3CN, AcOH | MeOH | RT | 30 min. | 50 | 644 |
| 303 | NH(2-amyl) | 4 | 2-Pentanone, NaBH3CN, AcOH | MeOH | RT | 30 min. | 50 | 658 |
| 304 | NHcyclohexyl | 4 | Cyclohexanone, NaBH3CN, AcOH | MeOH | RT | 45 min | 50 | 670 |
| 305 | NHPr | 4 | Propionaldehyde, NaBH3CN, AcOH | MeOH | RT | 45 min | 56 | 630 |
| 306 | NHCH2Ph | 4 | Benzaldehyde, NaBH3CN, AcOH | MeOH | RT | 45 min. | 60 | 678 |
| 307 | NH-3-amyl | 4 | 3-Pentanone, NaBH3CN, AcOH | MeOH | RT | 45 min. | 60 | 658 |
| 308 | NHBu | 4 | Butyraldehyde, NaBH3CN, AcOH | MeOH | RT | 45 min. | 48 | 644 |
| 309 | NHCH2tBu | 4 | Trimethylacetaldehyde, NaBH3CN, AcOH | MeOH | RT | 45 min | 50 | 658 |
| 310 | NHCH2CO2Et | 4 | Ethyl bromoacetate, NaOAc | THF | 40 | 3 hr | 20 | |
| 311 | Cl | 1 and 6 | 3-chloroindazole-5-sulfonyl chloride, NaHCO3 | CH2Cl2 | RT | 12 hr | 37 | 607 |
| 312 | NH2 | 5 | Hydrazine | EtOH | 50 | 2 hr | 70 | 588 |

TABLE 3-continued

Indazole Synthesis

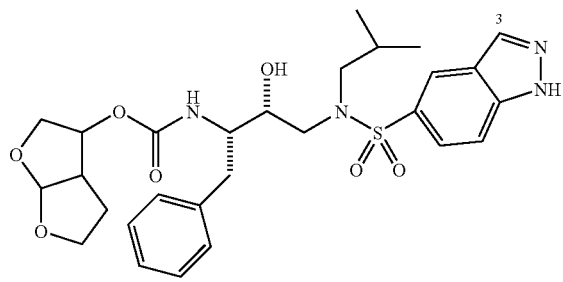

| Compound | 3- | Method | Reagents | Solvent | Temp ° C. | Time | Yield | MH+ |
|---|---|---|---|---|---|---|---|---|
| 313 | CH2Br | 1 | 3-bromomethylindazole-5-sulfonyl chloride, NaHCO3 | CH2Cl2 | RT | 6 hr | 75 | 663, 665 |
| 314 | NMe2 | 4 | Formaldehyde, NaBH3CN | Methanolic HCl | RT | 30 min. | 20 | 616 |
| 315 | N(C6H13)2 | 4 | Hexanal, NaBH3CN, AcOH | MeOH | RT | 45 min | 50 | 758 |
| 316 | NH2 (1-2-diethylaminoethyl) | 4 | 2-Bromo-N,N-diethylethylamine•HBr, K2CO3 | DMF | 60 | 45 min. | 60 | 687 |
| 317 | NHCO2Et | 4 | Ethylchloroformate, Et3N | ClCH2CH2Cl | RT | 12 hr | 35 | 660 |

TABLE 4

Synthesis of benzofuran related compounds

| Compound | Method | Reagents | Solvent | Temp ° C. | Time | Yield | MH+ | HPLC RT |
|---|---|---|---|---|---|---|---|---|
| 401 | 1 | NaHCO3 | DCM | RT | 16 h | 68% | NMR | 15.0 min |
| 402 | 1 | NaHCO3 | DCM | RT | 16 h | 85% | NMR | 15.4 min |

TABLE 4-continued

Synthesis of benzofuran related compounds

| Compound | Method | Reagents | Solvent | Temp °C. | Time | Yield | MH+ | HPLC RT |
|---|---|---|---|---|---|---|---|---|
| 403 | Reduction of ester | LiAlH4 | THF | RT | 16 h | 75% | | 13.5 min |
| 404 | 1 | NaHCO3 | DCM | RT | 16 h | 81% | 603 | 14.1 min |
| 405 | 1 | NaHCO3 | DCM | RT | 16 h | 70% | NMR | 15.6 min |
| 406 | 1 | NaHCO3 | DCM | RT | 16 h | 84% | | 15.0 min |

TABLE 5

Biological activity of Benzofurans

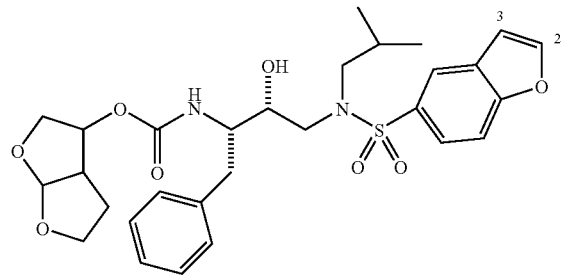

| Compound | 2- | 3- | Ki WT (nM) | Ki Mutant 8 (nM) | Ki Mutant 9 (nM) | IC50 WT (nM) | IC50 Mutant 8 (nM) | IC50 Mutant9 (nM) |
|---|---|---|---|---|---|---|---|---|
| 101 | H | H | <0.10 | <0.30 | 0.50 | 1.6 | 16 | 120 |
| 102 | Me | H | <0.10 | <0.30 | 0.96 | 3.7 | 90 | >400 |
| 103 | H | Me | <0.10 | <0.30 | 0.48 | 3.7 | 35 | 300 |
| 104 | CH2Br | H | <0.10 | <0.30 | 0.41 | 8.0 | 41 | 230 |
| 105 | CH2NH2 | H | <0.10 | <0.30 | 1.9 | 7.0 | 30 | 220 |
| 106 | CH2NHCH(Me)CO2Et | H | <0.10 | <0.30 | 1.8 | 30 | 30 | >400 |
| 107 | H | CH2NHCOMe | <0.10 | <0.30 | 0.26 | 15 | 28 | 42 |
| 108 | H | CH2-4-Morpholino | <0.10 | <0.30 | 1.5 | 1.5 | 38 | 420 |
| 109 | H | CH2-1-piperidino | <0.10 | <0.30 | 2.8 | 2.0 | 30 | >400 |
| 110 | H | CH2NHBoc | <0.10 | <0.30 | 0.32 | 3.4 | 33 | 62 |
| 111 | H | CH2S(O)Bu | <0.10 | <0.30 | 0.16 | 8.0 | 24 | 49 |
| 112 | H | CH2NHCO2Et | <0.10 | <0.30 | <0.10 | 1.8 | 11 | 29 |
| 113 | H | CH2NHCOEt | <0.10 | <0.30 | <0.10 | 7.0 | 20 | 50 |
| 114 | H | CH2NHCOPh | 0.10 | <0.30 | <0.10 | 4.0 | 23 | 30 |
| 115 | H | CH2NHSO2iPr | <0.10 | <0.30 | 0.27 | 6.0 | 18 | 64 |
| 116 | H | CH2NHCbz | <0.10 | <0.30 | 0.41 | 15 | 50 | 58 |
| 117 | H | CH2NH(CH2)2-2-pyridyl | <0.10 | <0.30 | <0.10 | 7.0 | 27 | 49 |
| 118 | H | CH2NHCO-3-pyridyl | <0.10 | <0.30 | 0.12 | 30 | 35 | 39 |
| 119 | H | CH2NHCOCH2SCH2Ph | 0.12 | <0.30 | 0.95 | 5.0 | 42 | 170 |
| 120 | H | CH2NHCOCH2S(O)CH2Ph | <0.10 | <0.30 | 0.22 | 20 | 31 | 150 |
| 121 | CH2NHCO2Et | H | <0.10 | <0.30 | 1.6 | 8.0 | 21 | >400 |
| 122 | H | CH2OAc | <0.10 | <0.30 | 0.27 | 5.9 | 11 | 110 |
| 123 | H | CH2OMe | 0.13 | <0.30 | 0.22 | 4.0 | 19 | 240 |
| 124 | H | CH2OH | <0.10 | <0.30 | 0.26 | 8.7 | 12 | 130 |
| 125 | H | CH2NHCO-2-furanyl | <0.10 | <0.30 | <0.10 | 5.0 | 9.0 | 31 |
| 126 | H | CH2N(CO2Et)CH2CH2OMe | <0.10 | <0.30 | 0.92 | 4.0 | 60 | 250 |

TABLE 6

Biological activity of Benzisoxazoles

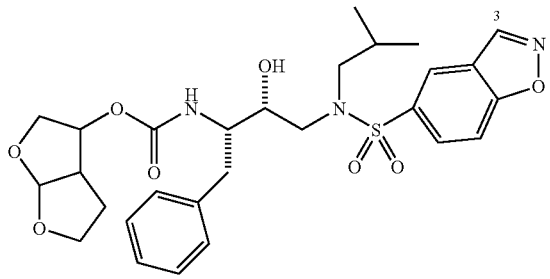

| Compound | 3- | Ki WT (nM) | Ki Mutant 8 (nM) | Ki Mutant 9 (nM) | IC50 WT (nM) | IC50 Mutant 8 (nM) | IC50 Mutant 9 (nM) |
|---|---|---|---|---|---|---|---|
| 201 | Me | <0.10 | <0.30 | <0.10 | 1.8 | 27 | 130 |
| 202 | CH2NHiPr | <0.10 | <0.30 | 3.5 | 3.2 | 38 | 210 |
| 203 | CH2NH2 | <0.10 | <0.30 | 0.71 | 22 | 70 | 120 |
| 204 | CH2NHSO2iPr | <0.10 | <0.30 | 0.14 | 6.5 | 31 | 83 |
| 205 | CH2OAc | <0.10 | <0.30 | 0.23 | 10 | 23 | 68 |
| 206 | CH2CH(Me)CO2Et | <0.10 | <0.30 | 0.33 | 5.0 | 30 | 160 |
| 207 | CH2NHSO2Me | <0.10 | <0.30 | 0.34 | 22 | 28 | 54 |

TABLE 6-continued

Biological activity of Benzisoxazoles

| Compound | 3- | Ki WT (nM) | Ki Mutant 8 (nM) | Ki Mutant 9 (nM) | IC50 WT (nM) | IC50 Mutant 8 (nM) | IC50 Mutant 9 (nM) |
|---|---|---|---|---|---|---|---|
| 208 | CH2S(O)Bu | <0.10 | <0.30 | <0.10 | 3.9 | 36 | 60 |
| 209 | CH2S-iPr | <0.10 | <0.30 | 2.3 | 3.5 | 50 | 210 |
| 210 | CH2NMeSO2Me | <0.10 | <0.30 | 1.3 | 3.0 | 51 | 300 |
| 211 | CH2NMeTs | <0.10 | <0.30 | 1.7 | 2.1 | 51 | 300 |
| 212 | CH2NHCO2iPr | <0.10 | <0.30 | 0.34 | 5.0 | 30 | >400 |
| 213 | CH2OH | <0.10 | <0.30 | 0.15 | 7.0 | 30 | 55 |
| 214 | CH2NHCOMe | <0.10 | <0.30 | <0.10 | 42 | 28 | 31 |
| 215 | CH2OCOiPr | <0.10 | <0.30 | 0.75 | 11 | 15 | 55 |
| 216 | CH2-1-imidazole | <0.10 | <0.30 | 1.7 | 20 | 32 | 250 |
| 217 | CH2NHCO2Et | <0.10 | <0.30 | <0.10 | 2.3 | 30 | 20 |
| 218 | CH2OCOtBu | <0.10 | <0.30 | 2.0 | 11 | 18 | 80 |
| 219 | CH2NHCH2CH2OMe | <0.10 | <0.30 | 0.37 | 4.0 | 9.0 | 40 |
| 220 | CH2NHCOiPr | <0.10 | <0.30 | 0.14 | 7.0 | 12 | 60 |
| 221 | CH2NHCOPh | <0.10 | <0.30 | <0.10 | 7.0 | 14 | 16 |
| 222 | CH2NHCO2Pr | <0.10 | <0.30 | 0.19 | 3.0 | 12 | 45 |
| 223 | CH2NHSO2Et | <0.10 | <0.30 | 0.26 | 9.0 | 11 | 60 |
| 224 | CH2NH(CH2)2-2-Pyr | <0.10 | <0.30 | 0.22 | 15 | 30 | 100 |
| 225 | CH2N((CH2)2OMe)CO2Et | <0.10 | <0.30 | 0.44 | 3.6 | 27 | 80 |
| 226 | CH2NHCH2CH2SEt | <0.10 | <0.30 | <0.10 | 5.5 | 16 | 38 |
| 227 | CH2N((CH2)2OMe)SO2Et | <0.10 | 0.41 | 2.6 | 3.6 | 27 | 80 |
| 228 | CH2NHCH2CF2CF3 | 0.12 | <0.30 | 0.20 | 4.5 | 9.5 | 26 |
| 229 | CH2NHCH2CF3 | <0.10 | <0.30 | 0.46 | 2.2 | 3.1 | 21 |
| 230 | CH2NHCH2CH2OPh | <0.10 | <0.30 | 0.14 | 4.8 | 20 | 57 |
| 231 | CH2NHBu | <0.10 | <0.30 | 0.29 | 4.3 | 23 | 60 |
| 232 | CH2NHCH2Ph | <0.10 | <0.30 | 0.11 | 7.0 | 55 | 80 |
| 233 | CH2SCH2CF3 | <0.10 | <0.30 | 3.4 | 4.0 | 36 | >400 |
| 234 | CH2NHCOCF3 | <0.10 | <0.30 | 0.36 | 16 | 23 | 85 |
| 235 | CH2NHcyclopentyl | <0.10 | <0.30 | 0.43 | 4.2 | 15 | 120 |
| 236 | CH2NHCH2CH2NHBoc | <0.10 | <0.30 | 0.34 | 6.0 | 18 | 160 |
| 237 | CH2NH(CH2)3-1-pyrrolidine-2-one | <0.10 | <0.30 | 0.27 | 31 | 41 | 85 |
| 238 | CH2NHCH2cyclohexyl | <0.10 | <0.30 | <0.10 | 7.5 | 35 | 55 |
| 239 | CH2-4-morpholino | <0.10 | <0.30 | 3.7 | 3.0 | 25 | >400 |
| 240 | CH2NHCO-2-furanyl | <0.10 | <0.30 | 0.26 | 6.5 | 11 | 20 |
| 241 | CH2NHCH2-2-pyridyl | 0.10 | <0.30 | 0.16 | 8.0 | 17 | 27 |
| 242 | CH2NHCH2-4-(2-methylthiazole) | <0.10 | <0.30 | 0.22 | 7.0 | 15 | 27 |
| 243 | CH2SO2Me | <0.10 | <0.30 | 0.96 | 8.2 | 24 | 120 |
| 244 | CH2OCH3 | <0.10 | <0.30 | 0.49 | 4.1 | 40 | 305 |
| 245 | CH2NHCOCF2CF3 | <0.10 | <0.30 | 0.63 | 8.4 | 30 | 190 |
| 246 | CH2OCH2CF3 | <0.10 | <0.30 | 1.1 | 2.7 | 6.8 | 105 |
| 247 | CH2N(Ac)CH2CF3 | <0.10 | <0.30 | 1.1 | 5.4 | 29 | >400 |
| 248 | CH2NHCH2-5-benzofuranyl | <0.10 | <0.30 | 0.33 | 7.9 | 24 | 54 |

TABLE 7
Biological activity of Indazoles
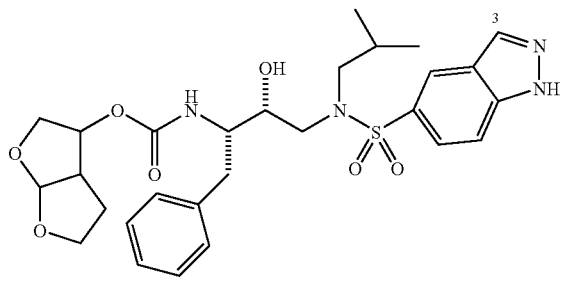
| Compound | 3- | Ki WT (nM) | Ki Mutant8 (nM) | Ki Mutant9 (nM) | IC50 WT (nM) | IC50 Mutant8 (nM) | IC50 Mutant9 (nM) |
|---|---|---|---|---|---|---|---|
| 201 | Me | <0.10 | <0.30 | 0.23 | 8.0 | 70 | 80 |
| 202 | NH(2-Bu) | <0.10 | <0.30 | 1.7 | 10 | 12 | 110 |
| 303 | NH(2-amyl) | <0.10 | <0.30 | 0.73 | 10 | 18 | 150 |
| 304 | NHcyclohexyl | <0.10 | <0.30 | 0.93 | 6.1 | 12 | 100 |
| 305 | NHPr | <0.10 | <0.30 | 0.66 | 16 | 30 | 180 |
| 306 | NHCH2Ph | 0.10 | <0.30 | 1.1 | 5.5 | 35 | 95 |
| 307 | NH-3-amyl | <0.10 | <0.30 | 0.55 | 7.5 | 24 | 110 |
| 308 | NHBu | <0.10 | <0.30 | 1.8 | 8.0 | 30 | 310 |
| 309 | NHCH2tBu | 0.13 | <0.30 | 3.5 | 4.0 | 25 | 250 |
| 310 | NHCH2CO2Et | <0.10 | <0.30 | 0.19 | 50 | 70 | 60 |
TABLE 8
Biological activity of Benzofuran related compounds
| Compound | Ki WT (nM) | Ki Mutant 8 (nM) | Ki Mutant 9 (nM) | IC50 WT (nM) | IC50 Mutant 8 (nM) | IC50 Mutant9 (nM) |
|---|---|---|---|---|---|---|
| 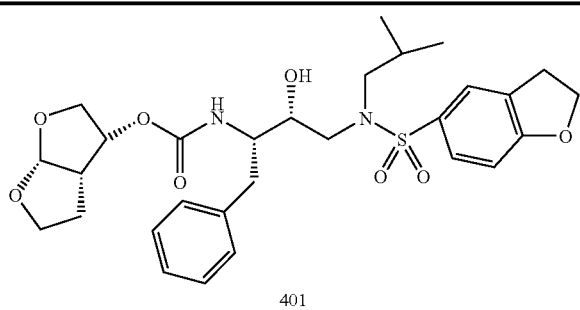 401 | <0.10 | <0.30 | 1.5 | 1.0 | 13 | 157 |
| 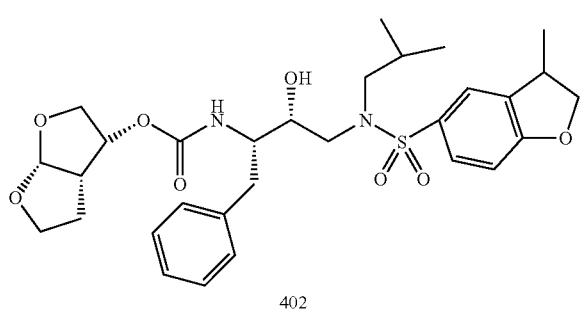 402 | <0.10 | 7.5 | 1.5 | 56 | 900 | |

TABLE 8-continued

Biological activity of Benzofuran related compounds

| Compound | Ki WT (nM) | Ki Mutant 8 (nM) | Ki Mutant 9 (nM) | IC50 WT (nM) | IC50 Mutant 8 (nM) | IC50 Mutant9 (nM) |
|---|---|---|---|---|---|---|
| 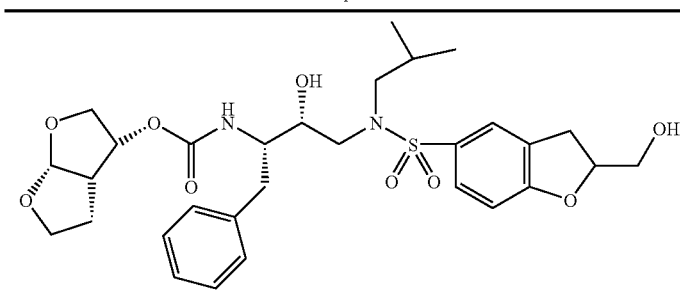 403 | <0.10 | 0.38 | 9.0 | 5.4 | 47 | 500 |
| 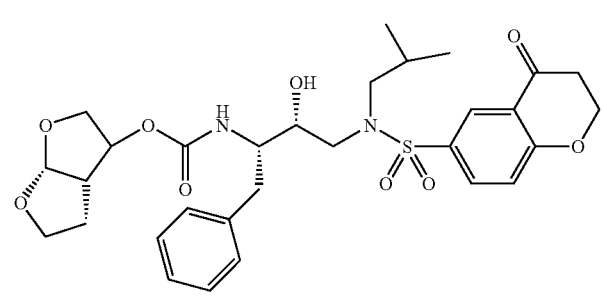 404 | <0.10 | 0.42 | 4.9 | 3.5 | 42 | 625 |

The following examples illustrate further the present invention but, of course, should not be construed in any way of limiting its scope.

EXAMPLES

Example 1

Preparation of Benzofuran-5-sulfonyl chlorides

Benzofuran-5-sulfonyl chlorides may be prepared by a bromination-dehydrobromination route as shown below:

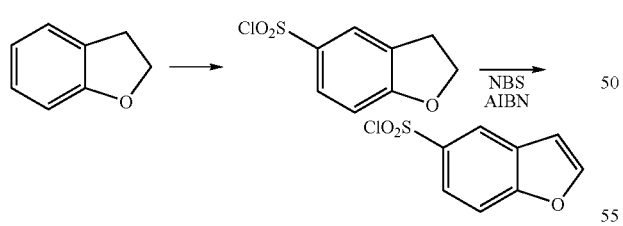

2,3-Dihydrobenzofuran-5-sulfonyl chloride was prepared from commercially available 2,3-dihydrobenzofuran as described in the patent EP 0583960A2.

Preparation of benzofuran-5-sulfonyl chloride 2,3-Dihydrobenzofuran-5-sulfonyl chloride 300 mg (1.37 mmol) was dissolved in 2 mL of benzene. N-bromosuccinimide 244 mg (1.37 mmol) and 3 mg AIBN were added to the solution and the reaction was heated at 80° C. for 1 hour. The reaction was allowed to come to room temperature, filtered and the filtrate was concentrated in vacuo. The residue was purified by chromatography on silica gel (30%CH2Cl2/hexanes) to afford 237 mg (80% yield) of the pure material.

3-Methyl-2,3-dihydrobenzofuran was synthesized as described in the literature starting from 2-iodophenol (Organic Synthesis, CV3, 418; L. W. Menapace and H. G. Kuivila, J. Amer. Chem. Soc., 86, 3047 (1964), and references cited therein).

3-Methyl-2,3-dihydrobenzofuran-5-sulfonyl chloride was prepared from 3-methyl-2,3-dihydrobenzofuran as described in the patent EP 0583960A2.

Preparation of 2-bromo-3-bromomethyl-benzofuran-5-sulfonyl chloride (5).

3-Methyl-2,3-dihydrobenzofuran-5-sulfonyl chloride (615 mg, 2.6 mmol) was dissolved in 15 mL of benzene.

N-bromosuccinimide (NBS) (471 mg, 2.6 mmol) and 10 mg AIBN were added to the solution and the reaction was heated at 80° C. for 1 hour. The reaction was allowed to come to room temperature, and then another equivalent of NBS and AIBN were added and the reaction was heated at 80° C. for another hour. A third equivalent of NBS and AIBN were added and the reaction was stirred at 80° C. 1 hour more. The reaction was allowed to come to room temperature, at which it was filtered and the solvent was removed from the filtrate in vacuo. The residue was purified by chromatography on silica gel (CH2Cl2-hexanes gradient 0-100%) to afford 147 mg (15% yield) of the final product.

After reaction of this material with the core the aliphatic bromine can be displaced by nucleophiles and the 2-bromine removed by hydrogenation.

Example 2

Preparation of Indazole-5-sulfonyl chlorides

Indazole-5-sulfonyl chlorides may be prepared by direct chlorosulfonylation of a protected indazole as shown below:

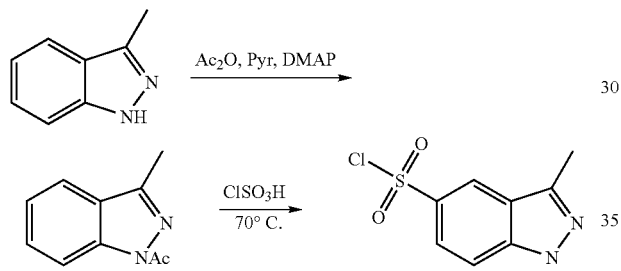

3-Methylindazole J. Med. Chem.; EN; 40; 17; 1997; 2706-2725

1-(3-methyl-indazol-1-yl)-ethanone

3-Methylindazole (1.00 g, 7.6 mmol) was dissolved in 10 ml THF and stirred at RT under a blanket of argon. Pyridine (0.64 ml, 7.9 mmol) was added followed by Ac$_2$O (0.79 ml, 8.3 mmol) and catalytic DMAP (90 mg, 0.7 mmol). The reaction proceeded for 2 h and was then partitioned between 1N HCl and dichloromethane. The organic phase was dried over MgSO4 and concentrated in vacuo to a tan solid (1.2 g, 91% yield).

Ref: Chem. Ber.; 53; 1920;1204

3-Methyl-1H-indazole-5-sulfonyl chloride (3)

To chlorosulfonic acid (0.38 ml, 5.7 mmol) under a blanket of argon in an ice bath was added 1-(3-methyl-indazol-1-yl)-ethanone (200 mg, 1.1 mmol). The reaction was allowed to warm to RT and then was heated at 70° C. for 45 min. The reaction was cooled to rt, slowly quenched over ice and extracted with dichloromethane. The organic phase was dried over MgSO4 and concentrated in vacuo to a tan solid (160 mg, 0.7 mmol, 61% yield).

Example 3

Preparation of Benzisoxazole-5-sulfonyl chlorides

Benzisoxazole-5-sulfonyl chlorides may be prepared by direct chlorosulfonylation of a suitable substituted benzisoxazole as shown below:

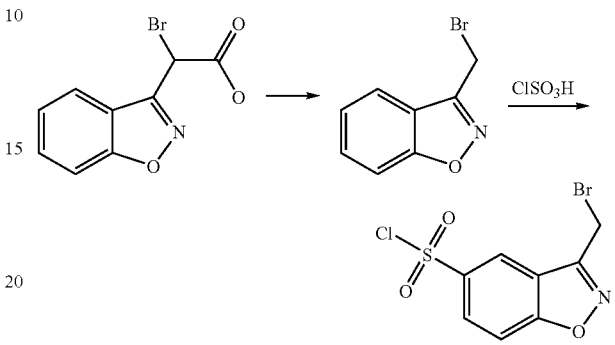

3-Bromomethyl-benzo[d]isoxazole

Benzo[d]isoxazol-3-yl-bromo-acetic acid (J. Med. Chem. 2003, 46; 5428-5436, Chem. Pharm. Bull.; EN; 26; 1978; 3498-3503) was slowly heated under argon with stirring to 130° C. and held there for 30 minutes. Copious gas evolution was observed during this time. The reaction was cooled to RT and the resulting brown crystals were filtered off and purified via column chromatography (hexanes), (2.3 g, 70% yield).

3-Bromomethyl-benzo[d]isoxazole-5-sulfonyl chloride

Chlorosulfonic acid (1.5 ml, 22 mmol) was slowly added to 3-Bromomethyl-benzo[d]isoxazole (1.0 g, 4.7 mmol) at RT under argon. The reaction was heated at 90° C. for 12 h and then left at RT for 6 h. The resulting viscous oil was quenched over ice, extracted with EtOAc, dried over MgSO4 and concentrated in vacuo to a brown oil (1.17 g, 80% yield).

After reaction of this material with the core the aliphatic bromine may be displaced by an appropriate nucleophile.

In Vitro Drug Sensitivity of HIV-1 Laboratory Isolates to PIs

The sensitivities of HIV-1 isolates against compounds of the invention were determined as previously described with minor modifications (Shiraska et al., *Proc. Natl. Acad. Sci. USA*, 92, 2398-2402 (1995)).

Any reference to any of the instant compounds also includes a reference to a pharmaceutically acceptable salts thereof.

Any reference to any of the instant compounds also includes a reference to a stereoisomer thereof.

Other substitutions, modifications, changes and omissions may be made in the design, operating conditions and arrangement of the preferred embodiments without departing from the spirit of the invention as expressed in the appended claims.

Additional advantages, features and modifications will readily occur to those skilled in the art. Therefore, the invention in its broader aspects is not limited to the specific details, and representative devices, shown and described herein.

Accordingly, various modifications may be made without departing from the spirit or scope of the general inventive concept as defined by the appended claims and their equivalents.

All of the references cited herein, including patents, patent applications, and publications, are hereby incorporated in their entireties by reference.

The claims below are not restricted to the particular embodiments described above.

What is claimed is:

1. A method of inhibiting metabolic degradation of a drug in a subject being treated with said drug, comprising administering to the subject a degradation-inhibiting amount of a compound represented by a formula:

X-A-B-A'-X' wherein:
X is tetrahydrofurotetrahydrofuranyl;
A is OCONH;

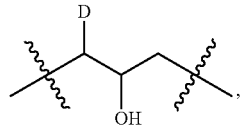

B is wherein D is aralkyl optionally substituted with one or more groups selected from alkyl, halo, nitro, cyano, $CF_3$, $C_3$-$C_7$ cycloalkyl, C5-C7 cycloalkenyl, R6, OR2, SR2, NHR2, OR3, SR3, NHR3, OR6, SR6, or NHR6;

A' is N(D')E', wherein D' is alkyl, optionally substituted by alkyl, halo, nitro, cyano, $CF_3$, O-alkyl, or S-alkyl, and E' is —CO— or —$SO_2$—;

X' is

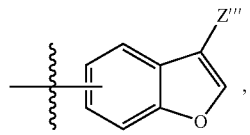

wherein Z''' is selected from the group consisting of H, R2, R3, R6, haloalkyl, $C(R2)_2OR$, $C(R2)_2COR$, $C(R2)_2OCOR$, $C(R2)_2CO_2R$, $C(R2)_2N(R)_2$, $C(R2)_2SOR$, and $C(R2)_2SO_2R$;

R is H or is selected from the group consisting of alkyl, aryl, alkenyl, alkynyl, cycloalkyl, cycloalkenyl, heterocyclo and heteroaryl; optionally substituted by halo, hydroxy, alkoxy, aryloxy, cycloalkoxy, heteroaryloxy, cyano, nitro, alkylthio, arylthio, cycloalkylthio, amino, or mono- or dialkylamino, mono- or diarylamino, mono- or di-cycloalkylamino, mono- or di-heteroarylamino, alkanoyl, cycloalkanoyl, aroyl, heteroaroyl, carboxamido, mono- or dialkylcarboxamido, mono- or diarylcarboxamido, sulfonamido, mono- or dialkylsulfonamido, mono- or diarylsulfonamido, alkylsulfinyl, alkylsulfonyl, arylsulfinyl, arylsulfonyl, cycloalkylsulfinyl, cycloalkylsulfonyl, heteroarylsulfinyl, heteroarylsulfonyl;

R2 is H or C1-C6 alkyl; optionally substituted by C2-C6 alkenyl, C2-C6 alkynyl, C3-C8 cycloalkyl, C5-C8 cycloalkenyl, heterocyclo; which groups may be optionally substituted with one or more substituents selected from the group consisting of halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, $NRS(O)_nR$, NRC[=N(R)]$N(R)_2$, $N(R)N(R)CO_nR$, $NRPO_nN(R)_2$, $NRPO_nOR$, oxo, =N—OR, =N—$N(R)_2$, =NR, =NNRC(O)$N(R)_2$, =NNRC$O_nR$, =NNRS(O)$_nN(R)_2$, or =NNRS(O)$_n$(R);

or R2 is $C_1$-$C_6$ alkyl; substituted by aryl or heteroaryl; which groups may be optionally substituted with one or more substituents selected from the group consisting of halo, OR, ROH, R-halo, $NO_2$, CN, $CO_nR$, $CON(R)_2$, C(S)R, $C(S)N(R)_2$, $SO_nN(R)_2$, $SO_nR$, $N(R)_2$, $N(R)CO_nR$, $NRS(O)_nR$, NRC[=N(R)]$N(R)_2$, $N(R)N(R)CO_nR$, $NRPO_nN(R)_2$ $NRPO_nOR$;

or R2 is C1-C6 alkyl; optionally substituted by halo, OR, ROH, R-halo, $NO_2$, CN, $CO_nR$, $CON(R)_2$, C(S)R, C(S)$N(R)_2$, $SO_nN(R)_2$, $SO_nR$, $N(R)_2$, $N(R)CO_nR$, $NRS(O)_nR$, NRC[=N(R)]$N(R)_2$, $N(R)N(R)CO_nR$, $NRPO_nN(R)_2$, $NRPO_nOR$, oxo, =N—OR, =N—$N(R)_2$, =NR, =NNRC(O)$N(R)_2$, =NNRCO$_nR$, =NNRS(O)$_nN(R)_2$, or =NNRS(O)$_n$(R);

R3 is C2-C6 alkenyl, C2-C6 alkynyl, C3-C8 cycloalkyl, C5-C8 cycloalkenyl, or heterocyclo; which groups may be optionally substituted with one or more substituents selected from the group consisting of halo, OR2, R2—OH, R2-halo, $NO_2$, CN, $CO_nR2$, $C(O)N(R2)_2$, $C(O)N(R2)N(R2)_2$, C(S)R2, $C(S)N(R2)_2$, $S(O)_nN(R2)_2$, SR2, $SO_nR2$, $N(R)_2$, $N(R2)CO_nR2$, $NR2S(O)_nR2$, NR2C[=N(R2)]$N(R2)_2$, $N(R2)N(R2)CO_nR2$, $NR2PO_nN(R2)_2$, $NR2PO_nOR2$, oxo, =N—OR2, =N—$N(R2)_2$, =NR2, =NNRC(O)$N(R2)_2$, =NNR2C(O)$_nR2$, =NNR2S(O)$_nN(R2)_2$, or =NNR2S(O)$_n$(R2);

R6 is aryl or heteroaryl, wherein said aryl or heteroaryl may be optionally substituted with one or more groups selected from aryl, heteroaryl, R2, R3, halo, OR2, R2OH, R2-halo, $NO_2$, CN, $CO_nR2$, $C(O)N(R2)_2$, $C(O)N(R2)N(R2)_2$, C(S)R2, $C(S)N(R2)_2$, $S(O)_nN(R2)_2$, $SO_nR2$, $N(R)_2$, $N(R2)CO_nR2$, $NR2S(O)_nR2$, NR2C[=N(R2)]$N(R2)_2$, $N(R2)N(R2)CO_nR2$, $NR2PO_nN(R2)_2$, $NR2PO_nOR2$, $OC(O)R2$, $OC(S)R2$, OC(O)$N(R2)_2$, OC(S)$N(R2)_2$, and $OPO_n(R2)_2$; and each n is independently 1 or 2.

2. The method according to claim 1, wherein Z''' is R2.

3. The method according to claim 2, wherein R2 is H or $C_{1-6}$ alkyl optionally substituted by halo.

4. The method according to claim 3, wherein R2 is H.

5. The method according to claim 1, wherein D is benzyl.

6. The method according to claim 1 wherein D' is isobutyl.

7. The method according to claim 1 wherein E' is —$SO_2$—.

8. The method according to claim 1 wherein R2 is H, D is benzyl, D' is isobutyl, and E' is —$SO_2$—.

9. The method according to claim 1, wherein Z''' is selected from the group consisting of H, Me, CH2OH, CH2OAc, CH2OMe, CH2NHiPr, CH2NH2, CH2S(O)Bu, CH2S-iPr, CH2OCOtBu, CH2NHCH2CH2OMe, CH2NHCOiPr, CH2NHCOPh, CH2NHCO2Pr, CH2NHCOMe, CH2-4-Morpholino, CH2-1-piperidino, CH2NHBoc, CH2NHCO2Et, CH2NHCOEt, CH2NHSO2iPr, CH2NHCbz, CH2NH(CH2)2-2-pyridyl, CH2NHCO-3-pyridyl, CH2NHCOCH2SCH2Ph, CH2NHCOCH2S(O)CH2Ph, CH2NHCO-2-furanyl, CH2N(CO2Et)CH2CH2OMe, NHCH(Me)CO2Et, CH2NHSO2Et, CH2NHSO2Me, CH2NMeSO2Me, CH2NMeTs, CH2NHCO2iPr, CH2OCOiPr, CH2-1-imidazole, CH2NHCH2CH2SEt, CH2N((CH2)2OMe)SO2Et, CH2NHCH2CF2CF3, CH2NHCH2CF3, CH2NHCH2CH2OPh, CH2NHBu, CH2NHCH2Ph, CH2SCH2CF3, CH2NHCOCF3, CH2NHcyclopentyl, CH2NHCH2CH2NHBoc, CH2NH(CH2)3-1-pyrrolidine-2-one, CH2NHCH2cyclohexyl, CH2NHCH2-2-pyridyl, CH2NHCH2-4-(2-methylthiazole), CH2SO2Me, CH2NHCOCF2CF3, CH2OCH2CF3, CH2N(Ac)CH2CF3, and CH2NHCH2-5-benzofuranyl.

10. The method according to claim 8, wherein Z'" is selected from the group consisting of H, Me, CH2OH, CH2OAc, CH2OMe, CH2NHiPr, CH2NH2, CH2S(O)Bu, CH2S-iPr, CH2OCOtBu, CH2NHCH2CH2OMe, CH2NHCOiPr, CH2NHCOPh, CH2NHCO2Pr, CH2NHCOMe, CH2-4-Morpholino, CH2-1-piperidino, CH2NHBoc, CH2NHCO2Et, CH2NHCOEt, CH2NHSO2iPr, CH2NHCbz, CH2NH(CH2)2-2-pyridyl, CH2NHCO-3-pyridyl, CH2NHCOCH2SCH2Ph, CH2NHCOCH2S(O)CH2Ph, CH2NHCO-2-furanyl, CH2N(CO2Et)CH2CH2OMe, NHCH(Me)CO2Et, CH2NHSO2Et, CH2NHSO2Me, CH2NMeSO2Me, CH2NMeTs, CH2NHCO2iPr, CH2OCOiPr, CH2-1-imidazole, CH2NHCH2CH2SEt, CH2N((CH2)2OMe)SO2Et, CH2NHCH2CF2CF3, CH2NHCH2CF3, CH2NHCH2CH2OPh, CH2NHBu, CH2NHCH2Ph, CH2SCH2CF3, CH2NHCOCF3, CH2NHcyclopentyl, CH2NHCH2CH2NHBoc, CH2NH(CH2)3-1-pyrrolidine-2-one, CH2NHCH2cyclohexyl, CH2NHCH2-2-pyridyl, CH2NHCH2-4-(2-methylthiazole), CH2SO2Me, CH2NHCOCF2CF3, CH2OCH2CF3, CH2N(Ac)CH2CF3, and CH2NHCH2-5-benzofuranyl.

11. The method of claim 1, wherein said compound is administered substantially contemporaneously with said drug.

12. The method of claim 1, wherein said compound is administered prior to administration of said drug.

13. The method of claim 1 wherein said drug and said compound are administered as a single composition.

* * * * *